United States Patent [19]
Komoriya et al.

[11] Patent Number: 6,037,137
[45] Date of Patent: *Mar. 14, 2000

[54] FLUOROGENIC PEPTIDES FOR THE DETECTION OF PROTEASE ACTIVITY

[75] Inventors: Akira Komoriya; Beverly S. Packard, both of Rockville, Md.

[73] Assignee: Oncoimmunin, Inc., Gaithersburg, Md.

[*] Notice: This patent is subject to a terminal disclaimer.

[21] Appl. No.: 08/802,981

[22] Filed: Feb. 20, 1997

[51] Int. Cl.[7] .................... C12Q 1/37; G01N 21/00; G01N 21/76; A61K 38/00
[52] U.S. Cl. ................ 435/23; 435/24; 435/7.72; 436/164; 436/172; 530/300; 530/350
[58] Field of Search .................... 435/4, 23, 24, 435/968, 7.6, 7.72, 7.9, 7.1; 436/164, 172; 530/300, 350

[56] References Cited

U.S. PATENT DOCUMENTS

| | | |
|---|---|---|
| 4,557,862 | 12/1985 | Mangel et al. . |
| 4,648,893 | 3/1987 | Roux . |
| 4,708,929 | 11/1987 | Henderson ............... 435/7.1 |
| 4,780,421 | 10/1988 | Kameda et al. ............ 436/51 |
| 4,897,444 | 1/1990 | Byrnes et al. . |
| 5,212,298 | 5/1993 | Rademacher et al. . |
| 5,605,809 | 2/1997 | Komoriya et al. ......... 435/23 |
| 5,714,392 | 2/1998 | Komoriya et al. ......... 435/23 |

FOREIGN PATENT DOCUMENTS

WO 96/13607  5/1996  WIPO .

OTHER PUBLICATIONS

FEBS Letters, vol. 30, No. 1, issued Feb. 1973, Carmel et al., "Use of Substrates With Fluorescent Donor and Acceptor Chromophores for the Kinetic Assay of Hydrolases", pp. 11–14.
FEBS Letters, vol. 296, No. 3, issued Jan. 1992, Knight et al., "A novel coumarin–labelled peptide for sensitive continuous assays of the matrix metalloproteinases", pp. 263–266.
Latt, S.A. et al. *Analytical Biochemistry* 50:56 (1972).
Matayoshi, E.D. et al. *Science*, 247: (1990).
Nagase, H. et al. *The Journal of Biological Chemisty* 269:20952 (1994).
Wang, G.T. et al. *Tetrahedron Letters* 31:6493 (1990).
Wu, P. et al. *Analytical Biochemistry* 218:1 (1994).
Keller, R.C. et al. *Biochemistry* 35:3063 (1996).
Isaac, V.e. et al. *Biochemistry* 34:15276 (1995).
Matsuzaki, K. et al. *Biochemistry* 34:6521 (1995).
Parkhurst, K.M. et al. *Biochemistry* 34:285 (1995).
Parkhurst, K.M. et al. 34:293 (1995).
Yang, M. et al. *Biochemistry* 35:7959 (1996).

*Primary Examiner*—Keith D. MacMillan
*Assistant Examiner*—Joseph W. Ricigliano
*Attorney, Agent, or Firm*—Majestic, Parsons, Siebert & Hsue

[57] ABSTRACT

The present invention provides for novel reagents whose fluorescence increases in the presence of particular proteases. The reagents comprise a characteristically folded peptide backbone each end of which is conjugated to a fluorophore. When the folded peptide is cleaved, as by digestion with a protease, the fluorophores provide a high intensity fluorescent signal at a visible wavelength. Because of their high fluorescence signal in the visible wavelengths, these protease indicators are particularly well suited for detection of protease activity in biological samples, in particular in frozen tissue sections. Thus this invention also provides for methods of detecting protease activity in situ in frozen sections.

38 Claims, 6 Drawing Sheets

D-NorFES + A-NorFES + Elastase

D-NorFES-A + Elastase

SEQUENCE LISTING (1) GENERAL INFORMATION:

(iii) NUMBER OF SEQUENCES: 231

(2) INFORMATION FOR SEQ ID NO:1:

(i) SEQUENCE CHARACTERISTICS:
      (A) LENGTH: 9 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Modified-site
      (B) LOCATION: 1
      (D) OTHER INFORMATION: /product= "OTHER"
          /note= "Xaa = donor fluorophore
            5'-carboxytetramethylrhodamine (C2211) linked
            to the alpha-amino group of Asp"

(ix) FEATURE:
      (A) NAME/KEY: Modified-site
      (B) LOCATION: 5
      (D) OTHER INFORMATION: /product= "Nle"

(ix) FEATURE:
      (A) NAME/KEY: Modified-site
      (B) LOCATION: 9
      (D) OTHER INFORMATION: /product= "OTHER"
          /note= "Xaa = acceptor fluorophore rhodamine X acetamide
            (R492) linked to the sulfhydryl group of Cys"

(xi) SEQUENCE DESCRIPTION: SEQ ID NO:1:

Xaa Ala Ile Pro Xaa Ser Ile Pro Xaa
1               5

```
(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Asp Glu Val Asp
1

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Asp Glu Val Asn
1

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Ile Pro Met Ser Ile
1               5

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Pro Met Ser Ile
1

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "Nle"
```

(xi) SEQUENCE DESCRIPTION: SEQ ID NO:6:

Pro Xaa Ser Ile
1

(2) INFORMATION FOR SEQ ID NO:7:

(i) SEQUENCE CHARACTERISTICS:
          (A) LENGTH: 9 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 5
          (D) OTHER INFORMATION: /product= "OTHER"
               /note= "Xaa = Met or Nle"

(ix) FEATURE:
          (A) NAME/KEY: Modified-site
          (B) LOCATION: 8
          (D) OTHER INFORMATION: /product= "OTHER"
               /note= "Xaa = Pro or Aib"

(ix) FEATURE:
          (A) NAME/KEY: Modified-site
          (B) LOCATION: 9
          (D) OTHER INFORMATION: /product= "OTHER"
               /note= "Xaa = Cys or Lys"

(xi) SEQUENCE DESCRIPTION: SEQ ID NO:7:

Asp Ala Ile Pro Xaa Ser Ile Xaa Xaa
1               5

(2) INFORMATION FOR SEQ ID NO:8:

(i) SEQUENCE CHARACTERISTICS:
          (A) LENGTH: 9 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 2
          (D) OTHER INFORMATION: /product= "OTHER"
               /note= "Xaa = Met, Aib or Pro"

(ix) FEATURE:
          (A) NAME/KEY: Modified-site
          (B) LOCATION: 3
          (D) OTHER INFORMATION: /product= "OTHER"
               /note= "Xaa = Thr, Aib or Pro"

(ix) FEATURE:
          (A) NAME/KEY: Modified-site
          (B) LOCATION: 8
          (D) OTHER INFORMATION: /product= "OTHER"
               /note= "Xaa = Pro or Aib"

(ix) FEATURE:
          (A) NAME/KEY: Modified-site
          (B) LOCATION: 9
          (D) OTHER INFORMATION: /product= "OTHER"
               /note= "Xaa = Cys or Lys"

```
        (xi) SEQUENCE DESCRIPTION: SEQ ID NO:8:

Asp Xaa Xaa Gly Arg Thr Gly Xaa Xaa
1               5

(2) INFORMATION FOR SEQ ID NO:9:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = Ala or Aib"

(ix) FEATURE:
         (A) NAME/KEY: Modified-site
         (B) LOCATION: 3
         (D) OTHER INFORMATION: /product= "OTHER"
             /note= "Xaa = Thr, Aib or Pro"

(ix) FEATURE:
         (A) NAME/KEY: Modified-site
         (B) LOCATION: 6
         (D) OTHER INFORMATION: /product= "OTHER"
             /note= "Xaa = Met or Nle"

(ix) FEATURE:
         (A) NAME/KEY: Modified-site
         (B) LOCATION: 8
         (D) OTHER INFORMATION: /product= "OTHER"
             /note= "Xaa = Pro or Aib"

(ix) FEATURE:
         (A) NAME/KEY: Modified-site
         (B) LOCATION: 9
         (D) OTHER INFORMATION: /product= "OTHER"
             /note= "Xaa = Cys or Lys"

(xi) SEQUENCE DESCRIPTION: SEQ ID NO:9:

Asp Xaa Xaa Phe Cys Xaa Leu Xaa Xaa
1               5

(2) INFORMATION FOR SEQ ID NO:10:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "Aib"

(ix) FEATURE:
         (A) NAME/KEY: Modified-site
         (B) LOCATION: 3
         (D) OTHER INFORMATION: /product= "OTHER"
             /note= "Xaa = Ser, Aib or Pro"

(ix) FEATURE:
         (A) NAME/KEY: Modified-site
         (B) LOCATION: 5
         (D) OTHER INFORMATION: /product= "OTHER"
             /note= "Xaa = Met or Nle"
```

```
    (ix) FEATURE:
          (A) NAME/KEY: Modified-site
          (B) LOCATION: 8
          (D) OTHER INFORMATION: /product= "OTHER"
              /note= "Xaa = Pro or Aib"

(ix) FEATURE:
          (A) NAME/KEY: Modified-site
          (B) LOCATION: 9
          (D) OTHER INFORMATION: /product= "OTHER"
              /note= "Xaa = Cys or Lys"

(xi) SEQUENCE DESCRIPTION: SEQ ID NO:10:

Asp Xaa Xaa Arg Xaa Ser Leu Xaa Xaa
1               5

(2) INFORMATION FOR SEQ ID NO:11:

(i) SEQUENCE CHARACTERISTICS:
          (A) LENGTH: 9 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 2
          (D) OTHER INFORMATION: /product= "OTHER"
              /note= "Xaa = Ile or Aib"

(ix) FEATURE:
          (A) NAME/KEY: Modified-site
          (B) LOCATION: 3
          (D) OTHER INFORMATION: /product= "OTHER"
              /note= "Xaa = Ala, Aib or Pro"

(ix) FEATURE:
          (A) NAME/KEY: Modified-site
          (B) LOCATION: 8
          (D) OTHER INFORMATION: /product= "OTHER"
              /note= "Xaa = Pro or Aib"

(ix) FEATURE:
          (A) NAME/KEY: Modified-site
          (B) LOCATION: 9
          (D) OTHER INFORMATION: /product= "OTHER"
              /note= "Xaa = Cys or Lys"

(xi) SEQUENCE DESCRIPTION: SEQ ID NO:11:

Asp Xaa Xaa Gly Arg Ser Leu Xaa Xaa
1               5

(2) INFORMATION FOR SEQ ID NO:12:

(i) SEQUENCE CHARACTERISTICS:
          (A) LENGTH: 9 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 2
          (D) OTHER INFORMATION: /product= "Aib"

(ix) FEATURE:
          (A) NAME/KEY: Modified-site
          (B) LOCATION: 3
          (D) OTHER INFORMATION: /product= "OTHER"
              /note= "Xaa = Thr, Aib or Pro"
```

-continued

```
    (ix) FEATURE:
         (A) NAME/KEY: Modified-site
         (B) LOCATION: 8
         (D) OTHER INFORMATION: /product= "OTHER"
              /note= "Xaa = Pro or Aib"

(ix) FEATURE:
         (A) NAME/KEY: Modified-site
         (B) LOCATION: 9
         (D) OTHER INFORMATION: /product= "OTHER"
              /note= "Xaa = Cys or Lys"

(xi) SEQUENCE DESCRIPTION: SEQ ID NO:12:

Asp Xaa Xaa Leu Leu Ser Leu Xaa Xaa
1               5

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
              /note= "Xaa = Gly or Aib"

(ix) FEATURE:
         (A) NAME/KEY: Modified-site
         (B) LOCATION: 3
         (D) OTHER INFORMATION: /product= "OTHER"
              /note= "Xaa = Pro or Aib"

(ix) FEATURE:
         (A) NAME/KEY: Modified-site
         (B) LOCATION: 8
         (D) OTHER INFORMATION: /product= "OTHER"
              /note= "Xaa = Pro or Aib"

(ix) FEATURE:
         (A) NAME/KEY: Modified-site
         (B) LOCATION: 9
         (D) OTHER INFORMATION: /product= "OTHER"
              /note= "Xaa = Cys or Lys"

(xi) SEQUENCE DESCRIPTION: SEQ ID NO:13:

Asp Xaa Xaa Leu Gly Ile Ala Xaa Xaa
1               5

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
              /note= "Xaa = Gly, Aib or Pro"
```

```
    (ix) FEATURE:
         (A) NAME/KEY: Modified-site
         (B) LOCATION: 3
         (D) OTHER INFORMATION: /product= "OTHER"
             /note= "Xaa = Pro or Aib"

(ix) FEATURE:
         (A) NAME/KEY: Modified-site
         (B) LOCATION: 8
         (D) OTHER INFORMATION: /product= "OTHER"
             /note= "Xaa = Pro or Aib"

(ix) FEATURE:
         (A) NAME/KEY: Modified-site
         (B) LOCATION: 9
         (D) OTHER INFORMATION: /product= "OTHER"
             /note= "Xaa = Cys or Lys"

(xi) SEQUENCE DESCRIPTION: SEQ ID NO:14:

Asp Xaa Xaa Gln Gly Ile Leu Xaa Xaa
1               5

(2) INFORMATION FOR SEQ ID NO:15:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = Gly, Aib or Pro"

(ix) FEATURE:
         (A) NAME/KEY: Modified-site
         (B) LOCATION: 3
         (D) OTHER INFORMATION: /product= "OTHER"
             /note= "Xaa = Pro or Aib"

(ix) FEATURE:
         (A) NAME/KEY: Modified-site
         (B) LOCATION: 8
         (D) OTHER INFORMATION: /product= "OTHER"
             /note= "Xaa = Pro or Aib"

(ix) FEATURE:
         (A) NAME/KEY: Modified-site
         (B) LOCATION: 9
         (D) OTHER INFORMATION: /product= "OTHER"
             /note= "Xaa = Cys or Lys"

(xi) SEQUENCE DESCRIPTION: SEQ ID NO:15:

Asp Xaa Xaa Gln Gly Leu Leu Xaa Xaa
1               5

(2) INFORMATION FOR SEQ ID NO:16:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide
```

```
    (ix) FEATURE:
         (A) NAME/KEY: Modified-site
         (B) LOCATION: 2
         (D) OTHER INFORMATION: /product= "OTHER"
             /note= "Xaa = Gly, Aib or Pro"

(ix) FEATURE:
         (A) NAME/KEY: Modified-site
         (B) LOCATION: 3
         (D) OTHER INFORMATION: /product= "OTHER"
             /note= "Xaa = Pro or Aib"

(ix) FEATURE:
         (A) NAME/KEY: Modified-site
         (B) LOCATION: 8
         (D) OTHER INFORMATION: /product= "OTHER"
             /note= "Xaa = Pro or Aib"

(ix) FEATURE:
         (A) NAME/KEY: Modified-site
         (B) LOCATION: 9
         (D) OTHER INFORMATION: /product= "OTHER"
             /note= "Xaa = Cys or Lys"

(xi) SEQUENCE DESCRIPTION: SEQ ID NO:16:

Asp Xaa Xaa Gln Gly Ile Ala Xaa Xaa
1               5

(2) INFORMATION FOR SEQ ID NO:17:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = Gly, Aib or Pro"

(ix) FEATURE:
         (A) NAME/KEY: Modified-site
         (B) LOCATION: 3
         (D) OTHER INFORMATION: /product= "OTHER"
             /note= "Xaa = Pro or Aib"

(ix) FEATURE:
         (A) NAME/KEY: Modified-site
         (B) LOCATION: 8
         (D) OTHER INFORMATION: /product= "OTHER"
             /note= "Xaa = Pro or Aib"

(ix) FEATURE:
         (A) NAME/KEY: Modified-site
         (B) LOCATION: 9
         (D) OTHER INFORMATION: /product= "OTHER"
             /note= "Xaa = Cys or Lys"

(xi) SEQUENCE DESCRIPTION: SEQ ID NO:17:

Asp Xaa Xaa Gln Ala Ile Ala Xaa Xaa
1               5

(2) INFORMATION FOR SEQ ID NO:18:

(i) SEQUENCE CHARACTERISTICS:
        (A) LENGTH: 9 amino acids
        (B) TYPE: amino acid
        (C) STRANDEDNESS:
        (D) TOPOLOGY: linear
```

```
        (ii) MOLECULE TYPE: peptide (ix) FEATURE:
             (A) NAME/KEY: Modified-site
             (B) LOCATION: 2
             (D) OTHER INFORMATION: /product= "OTHER"
                 /note= "Xaa = Gky, Aib or Pro"

(ix) FEATURE:
             (A) NAME/KEY: Modified-site
             (B) LOCATION: 3
             (D) OTHER INFORMATION: /product= "OTHER"
                 /note= "Xaa = Pro or Aib"

(ix) FEATURE:
             (A) NAME/KEY: Modified-site
             (B) LOCATION: 8
             (D) OTHER INFORMATION: /product= "OTHER"
                 /note= "Xaa = Pro or Aib"

(ix) FEATURE:
             (A) NAME/KEY: Modified-site
             (B) LOCATION: 9
             (D) OTHER INFORMATION: /product= "OTHER"
                 /note= "Xaa = Cys or Lys"

(xi) SEQUENCE DESCRIPTION: SEQ ID NO:18:

Asp Xaa Xaa Gln Gly Ile Ala Xaa Xaa
1               5

(2) INFORMATION FOR SEQ ID NO:19:

(i) SEQUENCE CHARACTERISTICS:
             (A) LENGTH: 9 amino acids
             (B) TYPE: amino acid
             (C) STRANDEDNESS:
             (D) TOPOLOGY: linear (ii) MOLECULE TYPE: peptide (ix) FEATURE:
             (A) NAME/KEY: Modified-site
             (B) LOCATION: 2
             (D) OTHER INFORMATION: /product= "OTHER"
                 /note= "Xaa = Gly, Aib or Pro"

(ix) FEATURE:
             (A) NAME/KEY: Modified-site
             (B) LOCATION: 3
             (D) OTHER INFORMATION: /product= "OTHER"
                 /note= "Xaa = Pro or Aib"

(ix) FEATURE:
             (A) NAME/KEY: Modified-site
             (B) LOCATION: 8
             (D) OTHER INFORMATION: /product= "OTHER"
                 /note= "Xaa = Pro or Aib"

(ix) FEATURE:
             (A) NAME/KEY: Modified-site
             (B) LOCATION: 9
             (D) OTHER INFORMATION: /product= "OTHER"
                 /note= "Xaa = Cys or Lys"

(xi) SEQUENCE DESCRIPTION: SEQ ID NO:19:

Asp Xaa Xaa Glu Gly Leu Arg Xaa Xaa
1               5

(2) INFORMATION FOR SEQ ID NO:20:

(i) SEQUENCE CHARACTERISTICS:
             (A) LENGTH: 9 amino acids
             (B) TYPE: amino acid
             (C) STRANDEDNESS:
             (D) TOPOLOGY: linear
```

```
    (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = Asp, Aib or Pro"

(ix) FEATURE:
         (A) NAME/KEY: Modified-site
         (B) LOCATION: 3
         (D) OTHER INFORMATION: /product= "OTHER"
             /note= "Xaa = Val, Aib or Pro"

(ix) FEATURE:
         (A) NAME/KEY: Modified-site
         (B) LOCATION: 8
         (D) OTHER INFORMATION: /product= "OTHER"
             /note= "Xaa = Pro or Aib"

(ix) FEATURE:
         (A) NAME/KEY: Modified-site
         (B) LOCATION: 9
         (D) OTHER INFORMATION: /product= "OTHER"
             /note= "Xaa = Cys or Lys"

(xi) SEQUENCE DESCRIPTION: SEQ ID NO:20:

Asp Xaa Xaa Gly His Phe Arg Xaa Xaa
1               5

(2) INFORMATION FOR SEQ ID NO:21:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = Asp, Aib or Pro"

(ix) FEATURE:
         (A) NAME/KEY: Modified-site
         (B) LOCATION: 3
         (D) OTHER INFORMATION: /product= "OTHER"
             /note= "Xaa = Thr, Aib or Pro"

(ix) FEATURE:
         (A) NAME/KEY: Modified-site
         (B) LOCATION: 7
         (D) OTHER INFORMATION: /product= "OTHER"
             /note= "Xaa = Met or Nle"

(ix) FEATURE:
         (A) NAME/KEY: Modified-site
         (B) LOCATION: 8
         (D) OTHER INFORMATION: /product= "OTHER"
             /note= "Xaa = Pro or Aib"

(ix) FEATURE:
         (A) NAME/KEY: Modified-site
         (B) LOCATION: 9
         (D) OTHER INFORMATION: /product= "OTHER"
             /note= "Xaa = Cys or Lys"

(xi) SEQUENCE DESCRIPTION: SEQ ID NO:21:

Asp Xaa Xaa Leu Glu Val Xaa Xaa Xaa
1               5
```

(2) INFORMATION FOR SEQ ID NO:22:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
           /note= "Xaa = Arg, Aib or Pro"

(ix) FEATURE:
        (A) NAME/KEY: Modified-site
        (B) LOCATION: 3
        (D) OTHER INFORMATION: /product= "OTHER"
           /note= "Xaa = Ala, Aib or Pro"

(ix) FEATURE:
        (A) NAME/KEY: Modified-site
        (B) LOCATION: 8
        (D) OTHER INFORMATION: /product= "OTHER"
           /note= "Xaa = Pro or Aib"

(ix) FEATURE:
        (A) NAME/KEY: Modified-site
        (B) LOCATION: 9
        (D) OTHER INFORMATION: /product= "OTHER"
           /note= "Xaa = Cys or Lys"

(xi) SEQUENCE DESCRIPTION: SEQ ID NO:22:

Asp Xaa Xaa Ile His Ile Gln Xaa Xaa
1               5

(2) INFORMATION FOR SEQ ID NO:23:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
           /note= "Xaa = Asp, Aib or Pro"

(ix) FEATURE:
        (A) NAME/KEY: Modified-site
        (B) LOCATION: 3
        (D) OTHER INFORMATION: /product= "OTHER"
           /note= "Xaa = Val, Aib or Pro"

(ix) FEATURE:
        (A) NAME/KEY: Modified-site
        (B) LOCATION: 8
        (D) OTHER INFORMATION: /product= "OTHER"
           /note= "Xaa = Pro or Aib"

(ix) FEATURE:
        (A) NAME/KEY: Modified-site
        (B) LOCATION: 9
        (D) OTHER INFORMATION: /product= "OTHER"
           /note= "Xaa = Cys or Lys"

(xi) SEQUENCE DESCRIPTION: SEQ ID NO:23:

Asp Xaa Xaa Ala Asn Tyr Asn Xaa Xaa
1               5

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = Gly, Aib or Pro"

(ix) FEATURE:
        (A) NAME/KEY: Modified-site
        (B) LOCATION: 3
        (D) OTHER INFORMATION: /product= "OTHER"
            /note= "Xaa = Pro or Aib"

(ix) FEATURE:
        (A) NAME/KEY: Modified-site
        (B) LOCATION: 8
        (D) OTHER INFORMATION: /product= "OTHER"
            /note= "Xaa = Pro or Aib"

(ix) FEATURE:
        (A) NAME/KEY: Modified-site
        (B) LOCATION: 9
        (D) OTHER INFORMATION: /product= "OTHER"
            /note= "Xaa = Cys or Lys"

(xi) SEQUENCE DESCRIPTION: SEQ ID NO:24:

Asp Xaa Xaa Ala Gly Glu Arg Xaa Xaa
1             5

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = Gly, Aib or Pro"

(ix) FEATURE:
        (A) NAME/KEY: Modified-site
        (B) LOCATION: 3
        (D) OTHER INFORMATION: /product= "OTHER"
            /note= "Xaa = Pro or Aib"

(ix) FEATURE:
        (A) NAME/KEY: Modified-site
        (B) LOCATION: 8
        (D) OTHER INFORMATION: /product= "OTHER"
            /note= "Xaa = Pro or Aib"

(ix) FEATURE:
        (A) NAME/KEY: Modified-site
        (B) LOCATION: 9
        (D) OTHER INFORMATION: /product= "OTHER"
            /note= "Xaa = Cys or Lys"

(xi) SEQUENCE DESCRIPTION: SEQ ID NO:25:

Asp Xaa Xaa Ala Gly Phe Ala Xaa Xaa
1             5

(2) INFORMATION FOR SEQ ID NO:26:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = Gly, Aib or Pro"

(ix) FEATURE:
        (A) NAME/KEY: Modified-site
        (B) LOCATION: 3
        (D) OTHER INFORMATION: /product= "OTHER"
            /note= "Xaa = Pro or Aib"

(ix) FEATURE:
        (A) NAME/KEY: Modified-site
        (B) LOCATION: 8
        (D) OTHER INFORMATION: /product= "OTHER"
            /note= "Xaa = Pro or Aib"

(ix) FEATURE:
        (A) NAME/KEY: Modified-site
        (B) LOCATION: 9
        (D) OTHER INFORMATION: /product= "OTHER"
            /note= "Xaa = Cys or Lys"

(xi) SEQUENCE DESCRIPTION: SEQ ID NO:26:

```
Asp Xaa Xaa Gln Gly Leu Ala Xaa Xaa
1               5
```

(2) INFORMATION FOR SEQ ID NO:27:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = Asp, Aib or Pro"

(ix) FEATURE:
        (A) NAME/KEY: Modified-site
        (B) LOCATION: 3
        (D) OTHER INFORMATION: /product= "OTHER"
            /note= "Xaa = Val, Aib or Pro"

(ix) FEATURE:
        (A) NAME/KEY: Modified-site
        (B) LOCATION: 8
        (D) OTHER INFORMATION: /product= "OTHER"
            /note= "Xaa = Pro or Aib"

(ix) FEATURE:
        (A) NAME/KEY: Modified-site
        (B) LOCATION: 9
        (D) OTHER INFORMATION: /product= "OTHER"
            /note= "Xaa = Cys or Lys"

```
        (xi) SEQUENCE DESCRIPTION: SEQ ID NO:27:

Asp Xaa Xaa Ala Gln Phe Val Xaa Xaa
1               5

(2) INFORMATION FOR SEQ ID NO:28:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = Asp, Aib or Pro"

(ix) FEATURE:
         (A) NAME/KEY: Modified-site
         (B) LOCATION: 3
         (D) OTHER INFORMATION: /product= "OTHER"
             /note= "Xaa = Gly, Pro or Aib"

(ix) FEATURE:
         (A) NAME/KEY: Modified-site
         (B) LOCATION: 8
         (D) OTHER INFORMATION: /product= "OTHER"
             /note= "Xaa = Pro or Aib"

(ix) FEATURE:
         (A) NAME/KEY: Modified-site
         (B) LOCATION: 9
         (D) OTHER INFORMATION: /product= "OTHER"
             /note= "Xaa = Cys or Lys"

(xi) SEQUENCE DESCRIPTION: SEQ ID NO:28:

Asp Xaa Xaa His Phe Leu Arg Xaa Xaa
1               5

(2) INFORMATION FOR SEQ ID NO:29:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = Thr, Aib or Pro"

(ix) FEATURE:
         (A) NAME/KEY: Modified-site
         (B) LOCATION: 3
         (D) OTHER INFORMATION: /product= "OTHER"
             /note= "Xaa = Thr, Pro or Aib"

(ix) FEATURE:
         (A) NAME/KEY: Modified-site
         (B) LOCATION: 8
         (D) OTHER INFORMATION: /product= "OTHER"
             /note= "Xaa = Pro or Aib"

(ix) FEATURE:
         (A) NAME/KEY: Modified-site
         (B) LOCATION: 9
         (D) OTHER INFORMATION: /product= "OTHER"
             /note= "Xaa = Cys or Lys"
```

(xi) SEQUENCE DESCRIPTION: SEQ ID NO:29:

Asp Xaa Xaa Glu Leu Phe Ser Xaa Xaa
1               5

(2) INFORMATION FOR SEQ ID NO:30:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = Lys, Aib or Pro"

(ix) FEATURE:
        (A) NAME/KEY: Modified-site
        (B) LOCATION: 3
        (D) OTHER INFORMATION: /product= "OTHER"
            /note= "Xaa = Phe, Pro or Aib"

(ix) FEATURE:
        (A) NAME/KEY: Modified-site
        (B) LOCATION: 8
        (D) OTHER INFORMATION: /product= "OTHER"
            /note= "Xaa = Pro or Aib"

(ix) FEATURE:
        (A) NAME/KEY: Modified-site
        (B) LOCATION: 9
        (D) OTHER INFORMATION: /product= "OTHER"
            /note= "Xaa = Cys or Lys"

(xi) SEQUENCE DESCRIPTION: SEQ ID NO:30:

Asp Xaa Xaa Leu Ala Phe Leu Xaa Xaa
1               5

(2) INFORMATION FOR SEQ ID NO:31:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = Phe, Aib or Pro"

(ix) FEATURE:
        (A) NAME/KEY: Modified-site
        (B) LOCATION: 3
        (D) OTHER INFORMATION: /product= "OTHER"
            /note= "Xaa = Ser, Pro or Aib"

(ix) FEATURE:
        (A) NAME/KEY: Modified-site
        (B) LOCATION: 8
        (D) OTHER INFORMATION: /product= "OTHER"
            /note= "Xaa = Pro or Aib"

```
    (ix) FEATURE:
         (A) NAME/KEY: Modified-site
         (B) LOCATION: 9
         (D) OTHER INFORMATION: /product= "OTHER"
             /note= "Xaa = Cys or Lys"

(xi) SEQUENCE DESCRIPTION: SEQ ID NO:31:

Asp Xaa Xaa His Phe Val Arg Xaa Xaa
1               5

(2) INFORMATION FOR SEQ ID NO:32:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = Gln, Aib or Pro"

(ix) FEATURE:
         (A) NAME/KEY: Modified-site
         (B) LOCATION: 3
         (D) OTHER INFORMATION: /product= "OTHER"
             /note= "Xaa = Gln, Pro or Aib"

(ix) FEATURE:
         (A) NAME/KEY: Modified-site
         (B) LOCATION: 8
         (D) OTHER INFORMATION: /product= "OTHER"
             /note= "Xaa = Pro or Aib"

(ix) FEATURE:
         (A) NAME/KEY: Modified-site
         (B) LOCATION: 9
         (D) OTHER INFORMATION: /product= "OTHER"
             /note= "Xaa = Cys or Lys"

(xi) SEQUENCE DESCRIPTION: SEQ ID NO:32:

Asp Xaa Xaa Leu Leu His Asn Xaa Xaa
1               5

(2) INFORMATION FOR SEQ ID NO:33:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = Gly, Aib or Pro"

(ix) FEATURE:
         (A) NAME/KEY: Modified-site
         (B) LOCATION: 3
         (D) OTHER INFORMATION: /product= "OTHER"
             /note= "Xaa = Ile, Pro or Aib"

(ix) FEATURE:
         (A) NAME/KEY: Modified-site
         (B) LOCATION: 8
         (D) OTHER INFORMATION: /product= "OTHER"
             /note= "Xaa = Pro or Aib"
```

```
    (ix) FEATURE:
         (A) NAME/KEY: Modified-site
         (B) LOCATION: 9
         (D) OTHER INFORMATION: /product= "OTHER"
             /note= "Xaa = Cys or Lys"

(xi) SEQUENCE DESCRIPTION: SEQ ID NO:33:

Asp Xaa Xaa Gln Tyr Thr Tyr Xaa Xaa
1               5

(2) INFORMATION FOR SEQ ID NO:34:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = Ser, Aib or Pro"

(ix) FEATURE:
         (A) NAME/KEY: Modified-site
         (B) LOCATION: 3
         (D) OTHER INFORMATION: /product= "OTHER"
             /note= "Xaa = Ser, Pro or Aib"

(ix) FEATURE:
         (A) NAME/KEY: Modified-site
         (B) LOCATION: 8
         (D) OTHER INFORMATION: /product= "OTHER"
             /note= "Xaa = Pro or Aib"

(ix) FEATURE:
         (A) NAME/KEY: Modified-site
         (B) LOCATION: 9
         (D) OTHER INFORMATION: /product= "OTHER"
             /note= "Xaa = Cys or Lys"

(xi) SEQUENCE DESCRIPTION: SEQ ID NO:34:

Asp Xaa Xaa Gln Tyr Ser Asn Xaa Xaa
1               5

(2) INFORMATION FOR SEQ ID NO:35:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = Ser, Aib or Pro"

(ix) FEATURE:
         (A) NAME/KEY: Modified-site
         (B) LOCATION: 3
         (D) OTHER INFORMATION: /product= "OTHER"
             /note= "Xaa = Ser, Pro or Aib"
```

```
        (ix) FEATURE:
              (A) NAME/KEY: Modified-site
              (B) LOCATION: 8
              (D) OTHER INFORMATION: /product= "OTHER"
                  /note= "Xaa = Pro or Aib"

(ix) FEATURE:
              (A) NAME/KEY: Modified-site
              (B) LOCATION: 9
              (D) OTHER INFORMATION: /product= "/OTHER"
                  /note= "Xaa = Cys or Lys"

(xi) SEQUENCE DESCRIPTION: SEQ ID NO:35:

Asp Xaa Xaa Ile Tyr Ser Gln Xaa Xaa
1               5

(2) INFORMATION FOR SEQ ID NO:36:

(i) SEQUENCE CHARACTERISTICS:
              (A) LENGTH: 9 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 2
              (D) OTHER INFORMATION: /product= "OTHER"
                  /note= "Xaa = Gly, Aib or Pro"

(ix) FEATURE:
              (A) NAME/KEY: Modified-site
              (B) LOCATION: 3
              (D) OTHER INFORMATION: /product= "OTHER"
                  /note= "Xaa = Pro or Aib"

(ix) FEATURE:
              (A) NAME/KEY: Modified-site
              (B) LOCATION: 8
              (D) OTHER INFORMATION: /product= "OTHER"
                  /note= "Xaa = Pro or Aib"

(ix) FEATURE:
              (A) NAME/KEY: Modified-site
              (B) LOCATION: 9
              (D) OTHER INFORMATION: /product= "OTHER"
                  /note= "Xaa = Cys or Lys"

(xi) SEQUENCE DESCRIPTION: SEQ ID NO:36:

Asp Xaa Xaa Ala Gly Val Gln Xaa Xaa
1               5

(2) INFORMATION FOR SEQ ID NO:37:

(i) SEQUENCE CHARACTERISTICS:
              (A) LENGTH: 4 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:37:

Gly Gly Gly Gly
        1

(2) INFORMATION FOR SEQ ID NO:38:

(i) SEQUENCE CHARACTERISTICS:
              (A) LENGTH: 12 amino acids
              (B) TYPE: amino acid
```

(C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(xi) SEQUENCE DESCRIPTION: SEQ ID NO:38:

Lys Asp Xaa Thr Gly Arg Thr Gly Pro Lys Gly Tyr
1               5                   10

(2) INFORMATION FOR SEQ ID NO:39:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:39:

Lys Asp Pro Pro Thr Gly Arg Thr Gly Pro Pro Lys Gly Tyr
    1               5                   10

(2) INFORMATION FOR SEQ ID NO:40:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(xi) SEQUENCE DESCRIPTION: SEQ ID NO:40:

Lys Asp Xaa Asp Glu Val Asp Gly Ile Asp Pro Lys Gly Tyr
1               5                   10

(2) INFORMATION FOR SEQ ID NO:41:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(xi) SEQUENCE DESCRIPTION: SEQ ID NO:41:

Lys Asp Xaa Asp Glu Val Asn Gly Ile Asp Pro Lys Gly Tyr
    1               5                   10

(2) INFORMATION FOR SEQ ID NO:42:

(i) SEQUENCE CHARACTERISTICS:
            (A) LENGTH: 13 amino acids
            (B) TYPE: amino acid (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:42:

Lys Asp Xaa Glu Val Asp Gly Ile Asp Pro Lys Gly Tyr
1               5                   10

(2) INFORMATION FOR SEQ ID NO:43:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "Aib"

(xi) SEQUENCE DESCRIPTION: SEQ ID NO:43:

Lys Asp Tyr Xaa Ala Asp Gly Ile Asp Pro Lys Gly Tyr
    1               5                   10

(2) INFORMATION FOR SEQ ID NO:44:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = 9-fluorenylmethoxycarbonyl (Fmoc) group
              attached to the alpha-amino group of Lys"

(ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:44:

Xaa Asp Xaa Asp Glu Val Asp Gly Ile Asp Pro Lys Gly Tyr
1               5                   10

(2) INFORMATION FOR SEQ ID NO:45:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide

```
        (ix) FEATURE:
             (A) NAME/KEY: Modified-site
             (B) LOCATION: 1
             (D) OTHER INFORMATION: /product= "OTHER"
                   /note= "Xaa = 9-fluorenylmethoxycarbonyl (Fmoc) group
                   attached to the alpha-amino group of Lys"

(ix) FEATURE:
             (A) NAME/KEY: Modified-site
             (B) LOCATION: 3
             (D) OTHER INFORMATION: /product= "Aib"

(xi) SEQUENCE DESCRIPTION: SEQ ID NO:45:

Xaa Asp Xaa Asp Glu Val Asn Gly Ile Asp Pro Lys Gly Tyr
1               5                   10

(2) INFORMATION FOR SEQ ID NO:46:

(i) SEQUENCE CHARACTERISTICS:
         (A) LENGTH: 13 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
               /note= "Xaa = 9-fluorenylmethoxycarbonyl (Fmoc) group attached
               to the alpha-amino group of Lys"

(ix) FEATURE:
         (A) NAME/KEY: Modified-site
         (B) LOCATION: 3
         (D) OTHER INFORMATION: /product= "Aib"

(xi) SEQUENCE DESCRIPTION: SEQ ID NO:46:

Xaa Asp Xaa Glu Val Asp Gly Ile Asp Pro Lys Gly Tyr
   1               5                   10

(2) INFORMATION FOR SEQ ID NO:47:

(i) SEQUENCE CHARACTERISTICS:
         (A) LENGTH: 12 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
               /note= "Xaa = 9-fluorenylmethoxycarbonyl (Fmoc) group
               attached to the alpha-amino group of Lys"

(xi) SEQUENCE DESCRIPTION: SEQ ID NO:47:

Xaa Asp Ala Ile Pro Met Ser Ile Pro Lys Gly Tyr
1               5                   10

(2) INFORMATION FOR SEQ ID NO:48:

(i) SEQUENCE CHARACTERISTICS:
         (A) LENGTH: 16 amino acids
         (B) TYPE: amino acid
         (C) STRANDEDNESS:
         (D) TOPOLOGY: linear (ii) MOLECULE TYPE: peptide
```

```
    (ix) FEATURE:
         (A) NAME/KEY: Modified-site
         (B) LOCATION: 1
         (D) OTHER INFORMATION: /product= "OTHER"
             /note= "Xaa = 9-fluorenylmethoxycarbonyl (Fmoc) group attached
             to the alpha-amino group of Lys"

(ix) FEATURE:
         (A) NAME/KEY: Modified-site
         (B) LOCATION: 3
         (D) OTHER INFORMATION: /product= "Aib"

(xi) SEQUENCE DESCRIPTION: SEQ ID NO:48:

Xaa Asp Xaa Gly Asp Glu Val Asp Gly Ile Asp Gly Pro Lys Gly Tyr
1               5                  10                 15

(2) INFORMATION FOR SEQ ID NO:49:

(i) SEQUENCE CHARACTERISTICS:
         (A) LENGTH: 18 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /note= "Xaa = 9-fluorenylmethoxycarbonyl (Fmoc) group attached
             to the alpha-amino group of Lys"

(ix) FEATURE:
         (A) NAME/KEY: Modified-site
         (B) LOCATION: 3
         (D) OTHER INFORMATION: /product= "Aib"

(ix) FEATURE:
         (A) NAME/KEY: Modified-site
         (B) LOCATION: 4
         (D) OTHER INFORMATION: /product= "Acp"

(ix) FEATURE:
         (A) NAME/KEY: Modified-site
         (B) LOCATION: 14
         (D) OTHER INFORMATION: /product= "Acp"

(xi) SEQUENCE DESCRIPTION: SEQ ID NO:49:

Xaa Asp Xaa Xaa Gly Asp Glu Val Asp Gly Ile Asp Gly Xaa Pro Lys
1               5                  10                 15

Gly Tyr (2) INFORMATION FOR SEQ ID NO:50:

(i) SEQUENCE CHARACTERISTICS:
         (A) LENGTH: 18 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /note= "Xaa = benzyloxycarbonyl (Z) group attached to the
             alpha-amino group of Lys"

(ix) FEATURE:
         (A) NAME/KEY: Modified-site
         (B) LOCATION: 3
         (D) OTHER INFORMATION: /product= "Aib"
```

```
        (ix) FEATURE:
              (A) NAME/KEY: Modified-site
              (B) LOCATION: 4
              (D) OTHER INFORMATION: /product= "Acp"

(ix) FEATURE:
              (A) NAME/KEY: Modified-site
              (B) LOCATION: 14
              (D) OTHER INFORMATION: /product= "Acp"

(xi) SEQUENCE DESCRIPTION: SEQ ID NO:50:

Xaa Asp Xaa Xaa Gly Asp Glu Val Asp Gly Ile Asp Gly Xaa Pro Lys
1               5                   10                  15

Gly Tyr (2) INFORMATION FOR SEQ ID NO:51:

(i) SEQUENCE CHARACTERISTICS:
              (A) LENGTH: 13 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /product= "OTHER"
                  /note= "Xaa = 9-fluorenylmethoxycarbonyl (Fmoc) group
                  attached to the alpha-amino group of Lys"

(ix) FEATURE:
              (A) NAME/KEY: Modified-site
              (B) LOCATION: 4
              (D) OTHER INFORMATION: /product= "Aib"

(xi) SEQUENCE DESCRIPTION: SEQ ID NO:51:

Xaa Asp Tyr Xaa Ala Asp Gly Ile Asp Pro Lys Gly Tyr
1               5                   10

(2) INFORMATION FOR SEQ ID NO:52:

(i) SEQUENCE CHARACTERISTICS:
              (A) LENGTH: 19 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 3
              (D) OTHER INFORMATION: /product= "Aib"

(ix) FEATURE:
              (A) NAME/KEY: Modified-site
              (B) LOCATION: 4
              (D) OTHER INFORMATION: /product= "Acp"

(ix) FEATURE:
              (A) NAME/KEY: Modified-site
              (B) LOCATION: 5
              (D) OTHER INFORMATION: /product= "Acp"

(ix) FEATURE:
              (A) NAME/KEY: Modified-site
              (B) LOCATION: 14
              (D) OTHER INFORMATION: /product= "Acp"
```

```
        (ix) FEATURE:
              (A) NAME/KEY: Modified-site
              (B) LOCATION: 15
              (D) OTHER INFORMATION: /product= "Acp"

(xi) SEQUENCE DESCRIPTION: SEQ ID NO:52:

Lys Asp Xaa Xaa Xaa Gly Asp Glu Val Asp Gly Ile Asp Xaa Xaa Pro
1               5                   10                  15

Lys Gly Tyr (2) INFORMATION FOR SEQ ID NO:53:

(i) SEQUENCE CHARACTERISTICS:
              (A) LENGTH: 18 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 3
              (D) OTHER INFORMATION: /product= "Aib"

(ix) FEATURE:
              (A) NAME/KEY: Modified-site
              (B) LOCATION: 4
              (D) OTHER INFORMATION: /product= "Acp"

(ix) FEATURE:
              (A) NAME/KEY: Modified-site
              (B) LOCATION: 14
              (D) OTHER INFORMATION: /product= "Acp"

(xi) SEQUENCE DESCRIPTION: SEQ ID NO:53:

Lys Asp Xaa Xaa Gly Asn Glu Val Asp Gly Ile Asp Gly Xaa Pro Lys
1               5                   10                  15

Gly Tyr (2) INFORMATION FOR SEQ ID NO:54:

(i) SEQUENCE CHARACTERISTICS:
              (A) LENGTH: 18 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 3
              (D) OTHER INFORMATION: /product= "Aib"

(ix) FEATURE:
              (A) NAME/KEY: Modified-site
              (B) LOCATION: 4
              (D) OTHER INFORMATION: /product= "Acp"

(ix) FEATURE:
              (A) NAME/KEY: Modified-site
              (B) LOCATION: 14
              (D) OTHER INFORMATION: /product= "Acp"

(xi) SEQUENCE DESCRIPTION: SEQ ID NO:54:

Lys Asp Xaa Xaa Gly Asp Glu Val Asp Gly Ile Asn Gly Xaa Pro Lys
1               5                   10                  15

Gly Tyr
```

(2) INFORMATION FOR SEQ ID NO:55:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 14
        (D) OTHER INFORMATION: /product= "Acp"

(xi) SEQUENCE DESCRIPTION: SEQ ID NO:55:

Lys Asp Xaa Xaa Gly Asn Glu Val Asp Gly Ile Asn Gly Xaa Pro Lys
1               5                   10                  15

Gly Tyr (2) INFORMATION FOR SEQ ID NO:56:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 14
        (D) OTHER INFORMATION: /product= "Acp"

(xi) SEQUENCE DESCRIPTION: SEQ ID NO:56:

Lys Asp Xaa Xaa Gly Asp Glu Val Asn Gly Ile Asn Gly Xaa Pro Lys
1               5                   10                  15

Gly Tyr (2) INFORMATION FOR SEQ ID NO:57:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3

```
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 14
            (D) OTHER INFORMATION: /product= "Acp"

(xi) SEQUENCE DESCRIPTION: SEQ ID NO:57:

Lys Asp Xaa Xaa Gly Asn Glu Val Asn Gly Ile Asn Gly Xaa Pro Lys
1               5                   10                  15

Gly Tyr (2) INFORMATION FOR SEQ ID NO:58:

(i) SEQUENCE CHARACTERISTICS:
            (A) LENGTH: 19 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 6
            (D) OTHER INFORMATION: /product= "OTHER"
                /note= "Xaa = tetrahydroisoquinoline-3-carboxylic acid"

(ix) FEATURE:
            (A) NAME/KEY: Modified-site
            (B) LOCATION: 15
            (D) OTHER INFORMATION: /product= "Acp"

(xi) SEQUENCE DESCRIPTION: SEQ ID NO:58:

Lys Asp Xaa Xaa Gly Xaa Asp Glu Val Asp Gly Ile Asp Gly Xaa Pro
1               5                   10                  15

Lys Gly Lys (2) INFORMATION FOR SEQ ID NO:59:

(i) SEQUENCE CHARACTERISTICS:
            (A) LENGTH: 19 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"
```

(ix) FEATURE:
        (A) NAME/KEY: Modified-site
        (B) LOCATION: 15
        (D) OTHER INFORMATION: /product= "Acp"

(xi) SEQUENCE DESCRIPTION: SEQ ID NO:59:

Lys Asp Xaa Xaa Gly Trp Asp Glu Val Asp Gly Ile Asp Gly Xaa Pro
1               5                   10                  15

Lys Gly Tyr (2) INFORMATION FOR SEQ ID NO:60:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:60:

Lys Asp Xaa Tyr Val Ala Asp Gly Ile Asp Pro Lys Gly Tyr
1               5                   10

(2) INFORMATION FOR SEQ ID NO:61:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:61:

Lys Asp Xaa Tyr Val Ala Asp Gly Ile Asn Pro Lys Gly Tyr
1               5                   10

(2) INFORMATION FOR SEQ ID NO:62:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:62:

Lys Asp Xaa Tyr Val Ala Asn Gly Ile Asn Pro Lys Gly Tyr
1               5                   10

(2) INFORMATION FOR SEQ ID NO:63:

(i) SEQUENCE CHARACTERISTICS:

(A) LENGTH: 16 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 3
    (D) OTHER INFORMATION: /product= "Aib"

(xi) SEQUENCE DESCRIPTION: SEQ ID NO:63:

Lys Asp Xaa Gly Tyr Val Ala Asp Gly Ile Asp Gly Pro Lys Gly Tyr
1               5                   10                  15

(2) INFORMATION FOR SEQ ID NO:64:

(i) SEQUENCE CHARACTERISTICS:
    (A) LENGTH: 16 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 3
    (D) OTHER INFORMATION: /product= "Aib"

(xi) SEQUENCE DESCRIPTION: SEQ ID NO:64:

Lys Asp Xaa Gly Tyr Val Ala Asp Gly Ile Asn Gly Pro Lys Gly Tyr
1               5                   10                  15

(2) INFORMATION FOR SEQ ID NO:65:

(i) SEQUENCE CHARACTERISTICS:
    (A) LENGTH: 16 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 3
    (D) OTHER INFORMATION: /product= "Aib"

(xi) SEQUENCE DESCRIPTION: SEQ ID NO:65:

Lys Asp Xaa Gly Tyr Val Ala Asn Gly Ile Asn Gly Pro Lys Gly Tyr
1               5                   10                  15

(2) INFORMATION FOR SEQ ID NO:66:

(i) SEQUENCE CHARACTERISTICS:
    (A) LENGTH: 18 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 3
    (D) OTHER INFORMATION: /product= "Aib"

(ix) FEATURE:
    (A) NAME/KEY: Modified-site
    (B) LOCATION: 4
    (D) OTHER INFORMATION: /product= "Acp"

(ix) FEATURE:
            (A) NAME/KEY: Modified-site
            (B) LOCATION: 14
            (D) OTHER INFORMATION: /product= "Acp"

(xi) SEQUENCE DESCRIPTION: SEQ ID NO:66:

Lys Asp Xaa Xaa Gly Tyr Val Ala Asp Gly Ile Asp Gly Xaa Pro Lys
1               5                   10                  15

Gly Tyr (2) INFORMATION FOR SEQ ID NO:67:

(i) SEQUENCE CHARACTERISTICS:
            (A) LENGTH: 18 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 14
            (D) OTHER INFORMATION: /product= "Acp"

(xi) SEQUENCE DESCRIPTION: SEQ ID NO:67:

Lys Asp Xaa Xaa Gly Tyr Val Ala Asn Gly Ile Asp Gly Xaa Pro Lys
1               5                   10                  15

Gly Tyr (2) INFORMATION FOR SEQ ID NO:68:

(i) SEQUENCE CHARACTERISTICS:
            (A) LENGTH: 18 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 14
            (D) OTHER INFORMATION: /product= "Acp"

(xi) SEQUENCE DESCRIPTION: SEQ ID NO:68:

Lys Asp Xaa Xaa Gly Tyr Val Ala Asn Gly Ile Asn Gly Xaa Pro Lys
1               5                   10                  15

Gly Tyr (2) INFORMATION FOR SEQ ID NO:69:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 14
        (D) OTHER INFORMATION: /product= "Acp"

(xi) SEQUENCE DESCRIPTION: SEQ ID NO:69:

Lys Asp Xaa Xaa Gly Tyr Val Ala Asp Gly Ile Asn Gly Xaa Pro Lys
1              5                   10               15

Gly Tyr (2) INFORMATION FOR SEQ ID NO:70:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:70:

Lys Asp Xaa Leu Val Glu Ile Asp Asn Gly Pro Lys Gly Tyr
1              5                   10

(2) INFORMATION FOR SEQ ID NO:71:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:71:

Lys Asp Xaa Gly Leu Val Glu Ile Asp Asn Gly Gly Pro Lys Gly Tyr
1              5                   10               15

(2) INFORMATION FOR SEQ ID NO:72:

(i) SEQUENCE CHARACTERISTICS:

```
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 14
        (D) OTHER INFORMATION: /product= "Acp"

(xi) SEQUENCE DESCRIPTION: SEQ ID NO:72:

Lys Asp Xaa Xaa Gly Leu Val Glu Ile Asp Asn Gly Gly Xaa Pro Lys
1               5                   10                  15

Gly Tyr (2) INFORMATION FOR SEQ ID NO:73:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 14
        (D) OTHER INFORMATION: /product= "Acp"

(xi) SEQUENCE DESCRIPTION: SEQ ID NO:73:

Lys Asp Xaa Xaa Gly Leu Val Glu Ile Asn Asn Gly Gly Xaa Pro Lys
1               5                   10                  15

Gly Tyr (2) INFORMATION FOR SEQ ID NO:74:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:74:
```

```
Lys Asp Xaa Gly Ile Glu Thr Asp Ser Gly Val Asp Asp Pro Lys Gly
1               5                  10                 15

Tyr
```

(2) INFORMATION FOR SEQ ID NO:75:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:75:

```
Lys Asp Xaa Gly Ile Glu Thr Asn Ser Gly Val Asp Asp Pro Lys Gly
1               5                  10                 15

Tyr
```

(2) INFORMATION FOR SEQ ID NO:76:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:76:

```
Lys Asp Xaa Gly Gly Ile Glu Thr Asp Ser Gly Val Asp Asp Gly Pro
1               5                  10                 15

Lys Gly Tyr
```

(2) INFORMATION FOR SEQ ID NO:77:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:77:

```
Lys Asp Xaa Gly Gly Ile Glu Thr Asn Ser Gly Val Gly Pro Lys Gly
1               5                  10                 15

Tyr
```

(2) INFORMATION FOR SEQ ID NO:78:

(i) SEQUENCE CHARACTERISTICS:

-continued

```
        (A) LENGTH: 17 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 13
        (D) OTHER INFORMATION: /product= "Acp"

(xi) SEQUENCE DESCRIPTION: SEQ ID NO:78:

Lys Asp Xaa Xaa Gly Ile Glu Thr Asp Ser Gly Val Xaa Pro Lys Gly
1               5                   10                  15

Tyr (2) INFORMATION FOR SEQ ID NO:79:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 13
        (D) OTHER INFORMATION: /product= "Acp"

(xi) SEQUENCE DESCRIPTION: SEQ ID NO:79:

Lys Asp Xaa Xaa Gly Ile Glu Thr Asn Ser Gly Val Xaa Pro Lys Gly
1               5                   10                  15

Tyr (2) INFORMATION FOR SEQ ID NO:80:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
```

(A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 15
        (D) OTHER INFORMATION: /product= "Acp"

(xi) SEQUENCE DESCRIPTION: SEQ ID NO:80:

Lys Asp Xaa Xaa Gly Gly Ile Glu Thr Asp Ser Gly Val Gly Xaa Pro
1               5                   10                  15

Lys Gly Tyr (2) INFORMATION FOR SEQ ID NO:81:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 15
        (D) OTHER INFORMATION: /product= "Acp"

(xi) SEQUENCE DESCRIPTION: SEQ ID NO:81:

Lys Asp Xaa Xaa Gly Gly Ile Glu Thr Asn Ser Gly Val Gly Xaa Pro
1               5                   10                  15

Lys Gly Tyr (2) INFORMATION FOR SEQ ID NO:82:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:82:

Lys Asp Xaa Gly Ser Glu Ser Met Asp Ser Gly Ile Ser Leu Asp Pro
1               5                   10                  15

Lys Gly Tyr (2) INFORMATION FOR SEQ ID NO:83:

(i) SEQUENCE CHARACTERISTICS:
        (A) LENGTH: 17 amino acids
        (B) TYPE: amino acid

```
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:83:

Lys Asp Xaa Gly Gly Ser Glu Ser Met Asp Ser Gly Gly Pro Lys Gly
    1               5                  10                  15

Tyr (2) INFORMATION FOR SEQ ID NO:84:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 15
        (D) OTHER INFORMATION: /product= "Acp"

(xi) SEQUENCE DESCRIPTION: SEQ ID NO:84:

Lys Asp Xaa Xaa Gly Gly Ser Glu Ser Met Asp Ser Gly Gly Xaa Pro
    1               5                  10                  15

Lys Gly Tyr (2) INFORMATION FOR SEQ ID NO:85:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 15
        (D) OTHER INFORMATION: /product= "Acp"
```

(xi) SEQUENCE DESCRIPTION: SEQ ID NO:85:

Lys Asp Xaa Xaa Gly Asp Val Val Cys Cys Ser Met Ser Gly Xaa Pro
1               5                   10                  15

Lys Gly Tyr (2) INFORMATION FOR SEQ ID NO:86:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 15
        (D) OTHER INFORMATION: /product= "Acp"

(xi) SEQUENCE DESCRIPTION: SEQ ID NO:86:

Lys Asp Xaa Xaa Gly Asp Val Val Cys Asp Ser Met Ser Gly Xaa Pro
1               5                   10                  15

Lys Gly Tyr (2) INFORMATION FOR SEQ ID NO:87:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 14
        (D) OTHER INFORMATION: /product= "Acp"

(xi) SEQUENCE DESCRIPTION: SEQ ID NO:87:

Lys Asp Xaa Xaa Gly Glu Asp Val Val Cys Cys Ser Gly Xaa Pro Lys
1               5                   10                  15

Gly Tyr (2) INFORMATION FOR SEQ ID NO:88:

(i) SEQUENCE CHARACTERISTICS:
        (A) LENGTH: 18 amino acids
        (B) TYPE: amino acid

```
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 14
        (D) OTHER INFORMATION: /product= "Acp"

(xi) SEQUENCE DESCRIPTION: SEQ ID NO:88:

Lys Asp Xaa Xaa Gly Glu Asp Val Val Cys Asp Ser Gly Xaa Pro Lys
1               5                  10                  15

Gly Tyr (2) INFORMATION FOR SEQ ID NO:89:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 14
        (D) OTHER INFORMATION: /product= "Acp"

(xi) SEQUENCE DESCRIPTION: SEQ ID NO:89:

Lys Asp Xaa Xaa Gly Asp Val Val Cys Cys Ser Met Gly Xaa Pro Lys
1               5                  10                  15

Gly Tyr (2) INFORMATION FOR SEQ ID NO:90:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"
```

```
    (ix) FEATURE:
         (A) NAME/KEY: Modified-site
         (B) LOCATION: 4
         (D) OTHER INFORMATION: /product= "Acp"

(ix) FEATURE:
         (A) NAME/KEY: Modified-site
         (B) LOCATION: 14
         (D) OTHER INFORMATION: /product= "Acp"

(xi) SEQUENCE DESCRIPTION: SEQ ID NO:90:

Lys Asp Xaa Xaa Gly Asp Val Val Cys Asp Ser Met Gly Xaa Pro Lys
1               5                   10                  15

Gly Tyr (2) INFORMATION FOR SEQ ID NO:91:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /product= "Aib"

(ix) FEATURE:
         (A) NAME/KEY: Modified-site
         (B) LOCATION: 4
         (D) OTHER INFORMATION: /product= "Acp"

(ix) FEATURE:
         (A) NAME/KEY: Modified-site
         (B) LOCATION: 12
         (D) OTHER INFORMATION: /product= "Acp"

(xi) SEQUENCE DESCRIPTION: SEQ ID NO:91:

Lys Asp Xaa Xaa Gly Val Cys Cys Ser Met Gly Xaa Pro Lys Gly Tyr
1               5                   10                  15

(2) INFORMATION FOR SEQ ID NO:92:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /product= "Aib"

(ix) FEATURE:
         (A) NAME/KEY: Modified-site
         (B) LOCATION: 4
         (D) OTHER INFORMATION: /product= "Acp"

(ix) FEATURE:
         (A) NAME/KEY: Modified-site
         (B) LOCATION: 12
         (D) OTHER INFORMATION: /product= "Acp"

(xi) SEQUENCE DESCRIPTION: SEQ ID NO:92:

Lys Asp Xaa Xaa Gly Val Cys Asp Ser Met Gly Xaa Pro Lys Gly Tyr
1               5                   10                  15
```

(2) INFORMATION FOR SEQ ID NO:93:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(xi) SEQUENCE DESCRIPTION: SEQ ID NO:93:

Lys Asp Xaa Xaa Gly Asp Glu Met Glu Glu Cys Ser Gln His Leu Pro
1               5                   10                  15

Lys Gly Tyr (2) INFORMATION FOR SEQ ID NO:94:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(xi) SEQUENCE DESCRIPTION: SEQ ID NO:94:

Lys Asp Xaa Xaa Gly Asp Glu Met Glu Glu Cys Pro Gln His Leu Pro
1               5                   10                  15

Lys Gly Tyr (2) INFORMATION FOR SEQ ID NO:95:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(xi) SEQUENCE DESCRIPTION: SEQ ID NO:95:

```
Lys Asp Xaa Xaa Gly Asp Glu Met Glu Glu Asp Ser Gln His Leu Pro
1               5                   10                  15

Lys Gly Tyr
```

(2) INFORMATION FOR SEQ ID NO:96:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(xi) SEQUENCE DESCRIPTION: SEQ ID NO:96:

```
Lys Asp Xaa Xaa Gly Glu Met Glu Glu Cys Ser Gln His Leu Pro Lys
1               5                   10                  15

Gly Tyr
```

(2) INFORMATION FOR SEQ ID NO:97:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(xi) SEQUENCE DESCRIPTION: SEQ ID NO:97:

```
Lys Asp Xaa Xaa Gly Glu Met Glu Glu Cys Pro Gln His Leu Pro Lys
1               5                   10                  15

Gly Tyr
```

(2) INFORMATION FOR SEQ ID NO:98:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
              (A) NAME/KEY: Modified-site
              (B) LOCATION: 4
              (D) OTHER INFORMATION: /product= "Acp"

(xi) SEQUENCE DESCRIPTION: SEQ ID NO:98:

Lys Asp Xaa Xaa Gly Glu Met Glu Glu Asp Ser Gln His Leu Pro Lys
1               5                  10                  15

Gly Tyr (2) INFORMATION FOR SEQ ID NO:99:

(i) SEQUENCE CHARACTERISTICS:
              (A) LENGTH: 19 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 3
              (D) OTHER INFORMATION: /product= "Aib"

(ix) FEATURE:
              (A) NAME/KEY: Modified-site
              (B) LOCATION: 4
              (D) OTHER INFORMATION: /product= "Acp"

(xi) SEQUENCE DESCRIPTION: SEQ ID NO:99:

Lys Asp Xaa Xaa Gly Glu Met Glu Glu Cys Ser Gln His Leu Gly Pro
1               5                  10                  15

Lys Gly Tyr (2) INFORMATION FOR SEQ ID NO:100:

(i) SEQUENCE CHARACTERISTICS:
              (A) LENGTH: 19 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 3
              (D) OTHER INFORMATION: /product= "Aib"

(ix) FEATURE:
              (A) NAME/KEY: Modified-site
              (B) LOCATION: 4
              (D) OTHER INFORMATION: /product= "Acp"

(xi) SEQUENCE DESCRIPTION: SEQ ID NO:100:

Lys Asp Xaa Xaa Gly Glu Met Glu Glu Cys Pro Gln His Leu Gly Pro
1               5                  10                  15

Lys Gly Tyr (2) INFORMATION FOR SEQ ID NO:101:

(i) SEQUENCE CHARACTERISTICS:
              (A) LENGTH: 19 amino acids
              (B) TYPE: amino acid
              (C) STRANDEDNESS:
              (D) TOPOLOGY: linear (ii) MOLECULE TYPE: peptide

```
    (ix) FEATURE:
         (A) NAME/KEY: Modified-site
         (B) LOCATION: 3
         (D) OTHER INFORMATION: /product= "Aib"

(ix) FEATURE:
         (A) NAME/KEY: Modified-site
         (B) LOCATION: 4
         (D) OTHER INFORMATION: /product= "Acp"

(xi) SEQUENCE DESCRIPTION: SEQ ID NO:101:

Lys Asp Xaa Xaa Gly Glu Met Glu Glu Asp Ser Gln His Leu Gly Pro
1               5                  10                  15

Lys Gly Tyr (2) INFORMATION FOR SEQ ID NO:102:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /product= "Aib"

(ix) FEATURE:
         (A) NAME/KEY: Modified-site
         (B) LOCATION: 4
         (D) OTHER INFORMATION: /product= "Acp"

(ix) FEATURE:
         (A) NAME/KEY: Modified-site
         (B) LOCATION: 16
         (D) OTHER INFORMATION: /product= "Acp"

(xi) SEQUENCE DESCRIPTION: SEQ ID NO:102:

Lys Asp Xaa Xaa Gly Glu Met Glu Glu Cys Ser Gln His Leu Gly Xaa
1               5                  10                  15

Pro Lys Gly Tyr
            20

(2) INFORMATION FOR SEQ ID NO:103:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /product= "Aib"

(ix) FEATURE:
         (A) NAME/KEY: Modified-site
         (B) LOCATION: 4
         (D) OTHER INFORMATION: /product= "Acp"

(ix) FEATURE:
         (A) NAME/KEY: Modified-site
         (B) LOCATION: 16
         (D) OTHER INFORMATION: /product= "Acp"
```

```
        (xi) SEQUENCE DESCRIPTION: SEQ ID NO:103:

Lys Asp Xaa Xaa Gly Glu Met Glu Glu Cys Pro Gln His Leu Gly Xaa
1               5                  10                  15

Pro Lys Gly Tyr
            20

(2) INFORMATION FOR SEQ ID NO:104:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 16
            (D) OTHER INFORMATION: /product= "Acp"

(xi) SEQUENCE DESCRIPTION: SEQ ID NO:104:

Lys Asp Xaa Xaa Gly Glu Met Glu Glu Asp Ser Gln His Leu Gly Xaa
1               5                  10                  15

Pro Lys Gly Tyr
            20

(2) INFORMATION FOR SEQ ID NO:105:

(i) SEQUENCE CHARACTERISTICS:
            (A) LENGTH: 17 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 13
            (D) OTHER INFORMATION: /product= "Acp"

(xi) SEQUENCE DESCRIPTION: SEQ ID NO:105:

Lys Asp Xaa Xaa Gly Val Met Thr Gly Arg Thr Gly Xaa Pro Lys Gly
1               5                  10                  15

Tyr (2) INFORMATION FOR SEQ ID NO:106:

(i) SEQUENCE CHARACTERISTICS:
```

(A) LENGTH: 17 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 13
            (D) OTHER INFORMATION: /product= "Acp"

(xi) SEQUENCE DESCRIPTION: SEQ ID NO:106:

Lys Asp Xaa Xaa Gly Val Met Thr Gly Arg Thr Gly Xaa Pro Lys Gly
1               5                   10                  15

Tyr (2) INFORMATION FOR SEQ ID NO:107:

(i) SEQUENCE CHARACTERISTICS:
            (A) LENGTH: 17 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 13
            (D) OTHER INFORMATION: /product= "Acp"

(xi) SEQUENCE DESCRIPTION: SEQ ID NO:107:

Lys Asp Xaa Xaa Gly Val Met Thr Gly Arg Thr Gly Xaa Pro Lys Gly
1               5                   10                  15

Tyr (2) INFORMATION FOR SEQ ID NO:108:

(i) SEQUENCE CHARACTERISTICS:
            (A) LENGTH: 16 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:

(A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 12
            (D) OTHER INFORMATION: /product= "Acp"

(xi) SEQUENCE DESCRIPTION: SEQ ID NO:108:

Lys Asp Xaa Xaa Gly Val Met Thr Gly Arg Gly Xaa Pro Lys Gly Tyr
1               5                   10                  15

(2) INFORMATION FOR SEQ ID NO:109:

(i) SEQUENCE CHARACTERISTICS:
            (A) LENGTH: 17 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 13
            (D) OTHER INFORMATION: /product= "Acp"

(xi) SEQUENCE DESCRIPTION: SEQ ID NO:109:

Lys Asp Xaa Xaa Gly Val Met Thr Gly Arg Gly Gly Xaa Pro Lys Gly
1               5                   10                  15

Tyr (2) INFORMATION FOR SEQ ID NO:110:

(i) SEQUENCE CHARACTERISTICS:
            (A) LENGTH: 17 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 13
            (D) OTHER INFORMATION: /product= "Acp"

(xi) SEQUENCE DESCRIPTION: SEQ ID NO:110:

Lys Asp Xaa Xaa Gly Val Met Thr Gly Arg Val Gly Xaa Pro Lys Gly
1               5                   10                  15

Tyr (2) INFORMATION FOR SEQ ID NO:111:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 13
        (D) OTHER INFORMATION: /product= "Acp"

(xi) SEQUENCE DESCRIPTION: SEQ ID NO:111:

```
Lys Asp Xaa Xaa Gly Val Met Thr Gly Arg Ala Gly Xaa Pro Lys Gly
1               5                   10                  15

Tyr
```

(2) INFORMATION FOR SEQ ID NO:112:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 16
        (D) OTHER INFORMATION: /product= "Acp"

(xi) SEQUENCE DESCRIPTION: SEQ ID NO:112:

```
Lys Asp Xaa Xaa Gly Ser Glu Val Asn Leu Asp Ala Glu Phe Gly Xaa
1               5                   10                  15

Pro Lys Asp Asp Tyr
                20
```

(2) INFORMATION FOR SEQ ID NO:113:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide

```
        (ix) FEATURE:
             (A) NAME/KEY: Modified-site
             (B) LOCATION: 3
             (D) OTHER INFORMATION: /product= "Aib"

(ix) FEATURE:
             (A) NAME/KEY: Modified-site
             (B) LOCATION: 4
             (D) OTHER INFORMATION: /product= "Acp"

(ix) FEATURE:
             (A) NAME/KEY: Modified-site
             (B) LOCATION: 16
             (D) OTHER INFORMATION: /product= "Acp"

(xi) SEQUENCE DESCRIPTION: SEQ ID NO:113:

Lys Asp Xaa Xaa Gly Ser Glu Val Lys Leu Asp Ala Glu Phe Gly Xaa
1               5                   10                  15

Pro Lys Asp Asp Tyr
                20

(2) INFORMATION FOR SEQ ID NO:114:

(i) SEQUENCE CHARACTERISTICS:
             (A) LENGTH: 21 amino acids
             (B) TYPE: amino acid
             (C) STRANDEDNESS:
             (D) TOPOLOGY: linear (ii) MOLECULE TYPE: peptide (ix) FEATURE:
             (A) NAME/KEY: Modified-site
             (B) LOCATION: 3
             (D) OTHER INFORMATION: /product= "Aib"

(ix) FEATURE:
             (A) NAME/KEY: Modified-site
             (B) LOCATION: 4
             (D) OTHER INFORMATION: /product= "Acp"

(ix) FEATURE:
             (A) NAME/KEY: Modified-site
             (B) LOCATION: 16
             (D) OTHER INFORMATION: /product= "Acp"

(xi) SEQUENCE DESCRIPTION: SEQ ID NO:114:

Lys Asp Xaa Xaa Gly Ser Glu Val Lys Met Asp Ala Glu Phe Gly Xaa
1               5                   10                  15

Pro Lys Asp Asp Tyr
                20

(2) INFORMATION FOR SEQ ID NO:115:

(i) SEQUENCE CHARACTERISTICS:
             (A) LENGTH: 21 amino acids
             (B) TYPE: amino acid
             (C) STRANDEDNESS:
             (D) TOPOLOGY: linear (ii) MOLECULE TYPE: peptide (ix) FEATURE:
             (A) NAME/KEY: Modified-site
             (B) LOCATION: 3
             (D) OTHER INFORMATION: /product= "Aib"

(ix) FEATURE:
             (A) NAME/KEY: Modified-site
             (B) LOCATION: 4
             (D) OTHER INFORMATION: /product= "Acp"

(ix) FEATURE:
```

(A) NAME/KEY: Modified-site
            (B) LOCATION: 16
            (D) OTHER INFORMATION: /product= "Acp"

(xi) SEQUENCE DESCRIPTION: SEQ ID NO:115:

Lys Asp Xaa Xaa Gly Ser Glu Val Lys Met Asp Glu Phe Gly Xaa
1               5                   10                  15

Pro Lys Asp Asp Tyr
            20

(2) INFORMATION FOR SEQ ID NO:116:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 16
        (D) OTHER INFORMATION: /product= "Acp"

(xi) SEQUENCE DESCRIPTION: SEQ ID NO:116:

Lys Asp Xaa Xaa Gly Ser Glu Val Asn Leu Asp Asp Glu Phe Gly Xaa
1               5                   10                  15

Pro Lys Asp Asp Tyr
            20

(2) INFORMATION FOR SEQ ID NO:117:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 18
        (D) OTHER INFORMATION: /product= "Acp"

(xi) SEQUENCE DESCRIPTION: SEQ ID NO:117:

Lys Asp Xaa Xaa Gly Gly Val Val Ile Ala Thr Val Ile Val Ile Thr
1               5                   10                  15

Gly Xaa Pro Lys Asp Asp Tyr
            20

(2) INFORMATION FOR SEQ ID NO:118:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 19
        (D) OTHER INFORMATION: /product= "Acp"

(xi) SEQUENCE DESCRIPTION: SEQ ID NO:118:

Lys Asp Xaa Xaa Gly Tyr Gly Val Val Ile Ala Thr Val Ile Val Ile
1               5                   10                  15
Thr Gly Xaa Pro Lys Asp Asp Tyr
                20

(2) INFORMATION FOR SEQ ID NO:119:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 13
        (D) OTHER INFORMATION: /product= "Acp"

(xi) SEQUENCE DESCRIPTION: SEQ ID NO:119:

Lys Asp Xaa Xaa Gly Val Ile Ala Thr Val Ile Gly Xaa Pro Lys Asp
1               5                   10                  15
Asp Tyr (2) INFORMATION FOR SEQ ID NO:120:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
    (A) NAME/KEY: Modified-site
    (B) LOCATION: 3
    (D) OTHER INFORMATION: /product= "Aib"

(ix) FEATURE:
    (A) NAME/KEY: Modified-site
    (B) LOCATION: 4
    (D) OTHER INFORMATION: /product= "Acp"

(ix) FEATURE:
    (A) NAME/KEY: Modified-site
    (B) LOCATION: 5
    (D) OTHER INFORMATION: /product= "Aib"

(ix) FEATURE:
    (A) NAME/KEY: Modified-site
    (B) LOCATION: 13
    (D) OTHER INFORMATION: /product= "Acp"

(xi) SEQUENCE DESCRIPTION: SEQ ID NO:120:

```
Lys Asp Xaa Xaa Xaa Tyr Gly Val Val Ile Ala Gly Xaa Pro Lys Asp
1               5                   10                  15

Asp Tyr
```

(2) INFORMATION FOR SEQ ID NO:121:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 5
        (D) OTHER INFORMATION: /product= "Acp"

(ix) FEATURE:
        (A) NAME/KEY: Modified-site
        (B) LOCATION: 12
        (D) OTHER INFORMATION: /product= "Acp"

(ix) FEATURE:
        (A) NAME/KEY: Modified-site
        (B) LOCATION: 13
        (D) OTHER INFORMATION: /product= "Acp"

(xi) SEQUENCE DESCRIPTION: SEQ ID NO:121:

```
Lys Asp Xaa Xaa Xaa Gln Gln Leu Leu His Asn Xaa Xaa Pro Lys
1               5                   10                  15
```

(2) INFORMATION FOR SEQ ID NO:122:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide

```
    (ix) FEATURE:
         (A) NAME/KEY: Modified-site
         (B) LOCATION: 3
         (D) OTHER INFORMATION: /product= "Aib"

(ix) FEATURE:
         (A) NAME/KEY: Modified-site
         (B) LOCATION: 4
         (D) OTHER INFORMATION: /product= "Acp"

(ix) FEATURE:
         (A) NAME/KEY: Modified-site
         (B) LOCATION: 13
         (D) OTHER INFORMATION: /product= "Acp"

(xi) SEQUENCE DESCRIPTION: SEQ ID NO:122:

Lys Asp Xaa Xaa Gly Gln Gln Leu Leu His Asn Gly Xaa Pro Lys
1               5                   10                  15

(2) INFORMATION FOR SEQ ID NO:123:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /product= "Aib"

(xi) SEQUENCE DESCRIPTION: SEQ ID NO:123:

Lys Asp Xaa Gly Gln Gln Leu Leu His Asn Gly Pro Lys
1               5                   10

(2) INFORMATION FOR SEQ ID NO:124:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /product= "Aib"

(xi) SEQUENCE DESCRIPTION: SEQ ID NO:124:

Lys Asp Xaa Gln Gln Leu Leu His Asn Pro Lys
1               5                   10

(2) INFORMATION FOR SEQ ID NO:125:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /product= "Aib"

(ix) FEATURE:
```

```
            (A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 5
            (D) OTHER INFORMATION: /product= "Acp"

(ix) FEATURE:
            (A) NAME/KEY: Modified-site
            (B) LOCATION: 12
            (D) OTHER INFORMATION: /product= "Acp"

(ix) FEATURE:
            (A) NAME/KEY: Modified-site
            (B) LOCATION: 13
            (D) OTHER INFORMATION: /product= "Acp"

(xi) SEQUENCE DESCRIPTION: SEQ ID NO:125:

Lys Asp Xaa Xaa Xaa Ser Ile Gln Tyr Thr Tyr Xaa Xaa Pro Lys
1               5                   10                  15

(2) INFORMATION FOR SEQ ID NO:126:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 13
            (D) OTHER INFORMATION: /product= "Acp"

(xi) SEQUENCE DESCRIPTION: SEQ ID NO:126:

Lys Asp Xaa Xaa Gly Ser Ile Gln Tyr Thr Tyr Gly Xaa Pro Lys
1               5                   10                  15

(2) INFORMATION FOR SEQ ID NO:127:

(i) SEQUENCE CHARACTERISTICS:
            (A) LENGTH: 13 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(xi) SEQUENCE DESCRIPTION: SEQ ID NO:127:

Lys Asp Xaa Gly Ser Ile Gln Tyr Thr Tyr Gly Pro Lys
1               5                   10

(2) INFORMATION FOR SEQ ID NO:128:
```

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:128:

Lys Asp Xaa Ser Ile Gln Tyr Thr Tyr Pro Lys
1               5                   10

(2) INFORMATION FOR SEQ ID NO:129:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 5
        (D) OTHER INFORMATION: /product= "Acp"

(ix) FEATURE:
        (A) NAME/KEY: Modified-site
        (B) LOCATION: 12
        (D) OTHER INFORMATION: /product= "Acp"

(ix) FEATURE:
        (A) NAME/KEY: Modified-site
        (B) LOCATION: 13
        (D) OTHER INFORMATION: /product= "Acp"

(xi) SEQUENCE DESCRIPTION: SEQ ID NO:129:

Lys Asp Xaa Xaa Xaa Ser Ser Gln Tyr Ser Asn Xaa Xaa Pro Lys
1               5                   10                  15

(2) INFORMATION FOR SEQ ID NO:130:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
         (A) NAME/KEY: Modified-site
         (B) LOCATION: 13
         (D) OTHER INFORMATION: /product= "Acp"

(xi) SEQUENCE DESCRIPTION: SEQ ID NO:130:

Lys Asp Xaa Xaa Gly Ser Ser Gln Tyr Ser Asn Gly Xaa Pro Lys
1               5                   10                  15

(2) INFORMATION FOR SEQ ID NO:131:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /product= "Aib"

(xi) SEQUENCE DESCRIPTION: SEQ ID NO:131:

Lys Asp Xaa Gly Ser Ser Gln Tyr Ser Asn Gly Pro Lys
1               5                   10

(2) INFORMATION FOR SEQ ID NO:132:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /product= "Aib"

(xi) SEQUENCE DESCRIPTION: SEQ ID NO:132:

Lys Asp Xaa Ser Ser Gln Tyr Ser Asn Pro Lys
1               5                   10

(2) INFORMATION FOR SEQ ID NO:133:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /product= "Aib"

(ix) FEATURE:
         (A) NAME/KEY: Modified-site
         (B) LOCATION: 4
         (D) OTHER INFORMATION: /product= "Acp"

(ix) FEATURE:
         (A) NAME/KEY: Modified-site
         (B) LOCATION: 5
         (D) OTHER INFORMATION: /product= "Acp"

(ix) FEATURE:
            (A) NAME/KEY: Modified-site
            (B) LOCATION: 12
            (D) OTHER INFORMATION: /product= "Acp"

(ix) FEATURE:
            (A) NAME/KEY: Modified-site
            (B) LOCATION: 13
            (D) OTHER INFORMATION: /product= "Acp"

(xi) SEQUENCE DESCRIPTION: SEQ ID NO:133:

Lys Asp Xaa Xaa Xaa Ser Ser Ile Tyr Ser Gln Xaa Xaa Pro Lys
1               5                   10                  15

(2) INFORMATION FOR SEQ ID NO:134:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"

(ix) FEATURE:
            (A) NAME/KEY: Modified-site
            (B) LOCATION: 13
            (D) OTHER INFORMATION: /product= "Acp"

(xi) SEQUENCE DESCRIPTION: SEQ ID NO:134:

Lys Asp Xaa Xaa Gly Ser Ser Ile Tyr Ser Gln Gly Xaa Pro Lys
1               5                   10                  15

(2) INFORMATION FOR SEQ ID NO:135:

(i) SEQUENCE CHARACTERISTICS:
            (A) LENGTH: 13 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(xi) SEQUENCE DESCRIPTION: SEQ ID NO:135:

Lys Asp Xaa Gly Ser Ser Ile Tyr Ser Gln Gly Pro Lys
1               5                   10

(2) INFORMATION FOR SEQ ID NO:136:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (ix) FEATURE:

(A) NAME/KEY: Modified-site
            (B) LOCATION: 3
            (D) OTHER INFORMATION: /product= "Aib"

(xi) SEQUENCE DESCRIPTION: SEQ ID NO:136:

Lys Asp Xaa Ser Ser Ile Tyr Ser Gln Pro Lys
1               5                   10

(2) INFORMATION FOR SEQ ID NO:137:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:137:

Asp Gly Ser Gly Gly Gly Glu Asp Glu Lys
1               5                   10

(2) INFORMATION FOR SEQ ID NO:138:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:138:

Lys Glu Asp Gly Gly Asp Lys
1               5

(2) INFORMATION FOR SEQ ID NO:139:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:139:

Asp Gly Ser Gly Glu Asp Glu Lys
    1               5

(2) INFORMATION FOR SEQ ID NO:140:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:140:

Lys Glu Asp Glu Gly Ser Gly Asp Lys
1               5

(2) INFORMATION FOR SEQ ID NO:141:

(i) SEQUENCE CHARACTERISTICS:
        (A) LENGTH: 8 amino acids
        (B) TYPE: amino acid (C) STRANDEDNESS:
        (D) TOPOLOGY: linear (ii) MOLECULE TYPE: peptide (xi) SEQUENCE DESCRIPTION: SEQ ID NO:141:

Asp Val Val Cys Cys Ser Met Ser
1               5

(2) INFORMATION FOR SEQ ID NO:142:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "Nle"

(xi) SEQUENCE DESCRIPTION: SEQ ID NO:142:

Asp Ala Ile Pro Xaa Ser Ile Pro Cys
1               5

(2) INFORMATION FOR SEQ ID NO:143:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:143:

Asp Ala Ile Pro Met Ser Ile Pro Cys
1               5

(2) INFORMATION FOR SEQ ID NO:144:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "Nle"

(xi) SEQUENCE DESCRIPTION: SEQ ID NO:144:

Asp Ala Ile Pro Xaa Ser Ile Pro Cys Gly Tyr
1               5                   10

(2) INFORMATION FOR SEQ ID NO:145:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide

```
        (ix) FEATURE:
              (A) NAME/KEY: Modified-site
              (B) LOCATION: 5
              (D) OTHER INFORMATION: /product= "Nle"

(xi) SEQUENCE DESCRIPTION: SEQ ID NO:145:

Asp Ala Ile Pro Xaa Ser Ile Pro Lys Gly Tyr
1               5                   10

(2) INFORMATION FOR SEQ ID NO:146:

(i) SEQUENCE CHARACTERISTICS:
              (A) LENGTH: 12 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 6
              (D) OTHER INFORMATION: /product= "Nle"

(xi) SEQUENCE DESCRIPTION: SEQ ID NO:146:

Lys Asp Ala Ile Pro Xaa Ser Ile Pro Lys Gly Tyr
1               5                   10

(2) INFORMATION FOR SEQ ID NO:147:

(i) SEQUENCE CHARACTERISTICS:
              (A) LENGTH: 11 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 2
              (D) OTHER INFORMATION: /product= "Aib"

(xi) SEQUENCE DESCRIPTION: SEQ ID NO:147:

Asp Xaa Thr Gly Arg Thr Gly Pro Lys Gly Tyr
1               5                   10

(2) INFORMATION FOR SEQ ID NO:148:

(i) SEQUENCE CHARACTERISTICS:
              (A) LENGTH: 12 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 3
              (D) OTHER INFORMATION: /product= "Aib"

(xi) SEQUENCE DESCRIPTION: SEQ ID NO:148:

Lys Asp Xaa Thr Gly Arg Thr Gly Pro Lys Gly Tyr
1               5                   10

(2) INFORMATION FOR SEQ ID NO:149:

(i) SEQUENCE CHARACTERISTICS:
              (A) LENGTH: 11 amino acids
              (B) TYPE: amino acid
```

(C) STRANDEDNESS:
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /product= "OTHER"
                        /note= "Xaa = a mixture of fluorophores 5- and
                        6-carboxytetramethylrhodamine (C1171) linked to the
                        alpha-amino group of Asp"

(ix) FEATURE:
                (A) NAME/KEY: Modified-site
                (B) LOCATION: 5
                (D) OTHER INFORMATION: /product= "Nle"

(ix) FEATURE:
                (A) NAME/KEY: Modified-site
                (B) LOCATION: 9
                (D) OTHER INFORMATION: /product= "OTHER"
                        /note= "Xaa = a mixture of fluorophores 5- and
                        6-carboxy-X-rhodamine (C1309) linked to the epsilon-amino
                        group of Lys"

(xi) SEQUENCE DESCRIPTION: SEQ ID NO:149:

Xaa Ala Ile Pro Xaa Ser Ile Pro Xaa Gly Tyr
1               5                   10

(2) INFORMATION FOR SEQ ID NO:150:

(i) SEQUENCE CHARACTERISTICS:
                (A) LENGTH: 11 amino acids
                (B) TYPE: amino acid
                (C) STRANDEDNESS:
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /product= "OTHER"
                        /note= "Xaa = a mixture of fluorophores 5- and
                        6-carboxy-X-rhodamine (C1309) linked to the alpha-amino
                        group of Asp"

(ix) FEATURE:
                (A) NAME/KEY: Modified-site
                (B) LOCATION: 5
                (D) OTHER INFORMATION: /product= "Nle"

(ix) FEATURE:
                (A) NAME/KEY: Modified-site
                (B) LOCATION: 9
                (D) OTHER INFORMATION: /product= "OTHER"
                        /note= "Xaa = a mixture of fluorophores 5- and
                        6-carboxytetramethylrhodamine (C1171) linked to the
                        epsilon-amino group of Lys"

(xi) SEQUENCE DESCRIPTION: SEQ ID NO:150:

Xaa Ala Ile Pro Xaa Ser Ile Pro Xaa Gly Tyr
1               5                   10

(2) INFORMATION FOR SEQ ID NO:151:

(i) SEQUENCE CHARACTERISTICS:
                (A) LENGTH: 11 amino acids
                (B) TYPE: amino acid
                (C) STRANDEDNESS:
                (D) TOPOLOGY: linear (ii) MOLECULE TYPE: peptide

```
        (ix) FEATURE:
             (A) NAME/KEY: Modified-site
             (B) LOCATION: 1
             (D) OTHER INFORMATION: /product= "OTHER"
                 /note= "Xaa = a mixture of fluorophores 5- and
                 6-carboxytetramethylrhodamine (C1171) linked to the
                 alpha-amino group of Asp"

(ix) FEATURE:
             (A) NAME/KEY: Modified-site
             (B) LOCATION: 5
             (D) OTHER INFORMATION: /product= "Nle"

(ix) FEATURE:
             (A) NAME/KEY: Modified-site
             (B) LOCATION: 9
             (D) OTHER INFORMATION: /product= "OTHER"
                 /note= "Xaa = a mixture of 5- and
                 6-carboxytetramethylrhodamine (C1171)
                 linked to the epsilon-amino group of Lys"

(xi) SEQUENCE DESCRIPTION: SEQ ID NO:151:

Xaa Ala Ile Pro Xaa Ser Ile Pro Xaa Gly Tyr
1               5                   10

(2) INFORMATION FOR SEQ ID NO:152:

(i) SEQUENCE CHARACTERISTICS:
             (A) LENGTH: 11 amino acids
             (B) TYPE: amino acid
             (C) STRANDEDNESS:
             (D) TOPOLOGY: linear (ii) MOLECULE TYPE: peptide (ix) FEATURE:
             (A) NAME/KEY: Modified-site
             (B) LOCATION: 5
             (D) OTHER INFORMATION: /product= "Nle"

(ix) FEATURE:
             (A) NAME/KEY: Modified-site
             (B) LOCATION: 9
             (D) OTHER INFORMATION: /product= "OTHER"
                 /note= "Xaa = a mixture of fluorophores 5- and
                 6-carboxy-X-rhodamine linked to the epsilon-amino group
                 of Lys"

(xi) SEQUENCE DESCRIPTION: SEQ ID NO:152:

Asp Ala Ile Pro Xaa Ser Ile Pro Xaa Gly Tyr
1               5                   10

(2) INFORMATION FOR SEQ ID NO:153:

(i) SEQUENCE CHARACTERISTICS:
             (A) LENGTH: 11 amino acids
             (B) TYPE: amino acid
             (C) STRANDEDNESS:
             (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /product= "OTHER"
                 /note= "Xaa = a mixture of fluorophores 5- and
                 6-carboxy-X-rhodamine linked to the alpha-amino group of
                 Asp"

(ix) FEATURE:
             (A) NAME/KEY: Modified-site
             (B) LOCATION: 5
             (D) OTHER INFORMATION: /product= "Nle"
```

-continued (xi) SEQUENCE DESCRIPTION: SEQ ID NO:153:

Xaa Ala Ile Pro Xaa Ser Ile Pro Lys Gly Tyr
1               5                   10

(2) INFORMATION FOR SEQ ID NO:154:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "Nle"

(ix) FEATURE:
        (A) NAME/KEY: Modified-site
        (B) LOCATION: 9
        (D) OTHER INFORMATION: /product= "OTHER"
            /note= "Xaa = a mixture of fluorophores 5- and
            6-carboxytetramethylrhodamine (C1171) linked to the
            epsilon-amino group of Lys"

(xi) SEQUENCE DESCRIPTION: SEQ ID NO:154:

Asp Ala Ile Pro Xaa Ser Ile Pro Xaa Gly Tyr
1               5                   10

(2) INFORMATION FOR SEQ ID NO:155:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = a mixture of fluorophores 5- and
            6-carboxytetramethylrhodamine (C1171) linked to the
            alpha-amino group of Asp"

(ix) FEATURE:
        (A) NAME/KEY: Modified-site
        (B) LOCATION: 5
        (D) OTHER INFORMATION: /product= "Nle"

(xi) SEQUENCE DESCRIPTION: SEQ ID NO:155:

Xaa Ala Ile Pro Xaa Ser Ile Pro Lys Gly Tyr
1               5                   10

(2) INFORMATION FOR SEQ ID NO:156:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide

```
    (ix) FEATURE:
          (A) NAME/KEY: Modified-site
          (B) LOCATION: 1
          (D) OTHER INFORMATION: /product= "OTHER"
                /note= "Xaa = fluorescein linked to the alpha-amino group
                 of Asp"

(ix) FEATURE:
          (A) NAME/KEY: Modified-site
          (B) LOCATION: 5
          (D) OTHER INFORMATION: /product= "Nle"

(ix) FEATURE:
          (A) NAME/KEY: Modified-site
          (B) LOCATION: 9
          (D) OTHER INFORMATION: /product= "OTHER"
                /note= "Xaa = fluorescien linked to the epsilon-amino
                 group of Lys"

(xi) SEQUENCE DESCRIPTION: SEQ ID NO:156:

Xaa Ala Ile Pro Xaa Ser Ile Pro Xaa Gly Tyr
1               5                   10

(2) INFORMATION FOR SEQ ID NO:157:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
                /note= "Xaa = a mixture of fluorophores 5- and
                 6-carboxy-X-rhodamine (C1309) linked to the alpha-amino
                 group of Asp"

(ix) FEATURE:
          (A) NAME/KEY: Modified-site
          (B) LOCATION: 5
          (D) OTHER INFORMATION: /product= "Nle"

(ix) FEATURE:
          (A) NAME/KEY: Modified-site
          (B) LOCATION: 9
          (D) OTHER INFORMATION: /product= "OTHER"
                /note= "Xaa = a mixture of fluorophores 5- and
                 6-carboxy-X-rhodamine (C1309) linked to the epsilon-amino
                 group of Lys"

(xi) SEQUENCE DESCRIPTION: SEQ ID NO:157:

Xaa Ala Ile Pro Xaa Ser Ile Pro Xaa Gly Tyr
1               5                   10

(2) INFORMATION FOR SEQ ID NO:158:

(i) SEQUENCE CHARACTERISTICS:
          (A) LENGTH: 12 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
                /note= "Xaa = a mixture of fluorophores 5- and
                 6-carboxytetramethylrhodamine (C1171) linked to the
                 epsilon-amino group of Lys"
```

```
        (ix) FEATURE:
              (A) NAME/KEY: Modified-site
              (B) LOCATION: 6
              (D) OTHER INFORMATION: /product= "Nle"

(ix) FEATURE:
              (A) NAME/KEY: Modified-site
              (B) LOCATION: 10
              (D) OTHER INFORMATION: /product= "OTHER"
                    /note= "Xaa = a mixture of 5- and 6-carboxy-X-rhodamine
                    linked to the epsilon-amino group of Lys"

(xi) SEQUENCE DESCRIPTION: SEQ ID NO:158:

Xaa Asp Ala Ile Pro Xaa Ser Ile Pro Xaa Gly Tyr
1               5                   10

(2) INFORMATION FOR SEQ ID NO:159:

(i) SEQUENCE CHARACTERISTICS:
              (A) LENGTH: 12 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /product= "OTHER"
                    /note= "Xaa = a mixture of fluorophores 5- and
                    6-carboxytetramethylrhodamine linked to the epsilon-amino
                    group of Lys"

(ix) FEATURE:
              (A) NAME/KEY: Modified-site
              (B) LOCATION: 6
              (D) OTHER INFORMATION: /product= "Nle"

(ix) FEATURE:
              (A) NAME/KEY: Modified-site
              (B) LOCATION: 10
              (D) OTHER INFORMATION: /product= "OTHER"
                    /note= "Xaa = a mixture of fluorophores 5- and
                    6-carboxytetramethylrhodamine linked to the epsilon-amino
                    group of Lys"

(xi) SEQUENCE DESCRIPTION: SEQ ID NO:159:

Xaa Asp Ala Ile Pro Xaa Ser Ile Pro Xaa Gly Tyr
1               5                   10

(2) INFORMATION FOR SEQ ID NO:160:

(i) SEQUENCE CHARACTERISTICS:
              (A) LENGTH: 12 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /product= "OTHER"
                    /note= "Xaa = fluorophore 1 linked to the alpha-amino
                    group of Asp"

(ix) FEATURE:
              (A) NAME/KEY: Modified-site
              (B) LOCATION: 6
              (D) OTHER INFORMATION: /product= "Nle"

(ix) FEATURE:
```

(A) NAME/KEY: Modified-site
            (B) LOCATION: 10
            (D) OTHER INFORMATION: /product= "OTHER"
                /note= "Xaa = fluorophore 2 linked to the epsilon-amino
                group of Lys"

(xi) SEQUENCE DESCRIPTION: SEQ ID NO:160:

Xaa Asp Ala Ile Pro Xaa Ser Ile Pro Xaa Gly Tyr
1               5                   10

(2) INFORMATION FOR SEQ ID NO:161:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
                /note= "Xaa = fluorophore 1 linked to the alpha-amino
                group of Asp"

(ix) FEATURE:
        (A) NAME/KEY: Modified-site
        (B) LOCATION: 9
        (D) OTHER INFORMATION: /product= "OTHER"
                /note= "Xaa = fluorophore 1 linked to the epsilon-amino
                group of Lys"

(xi) SEQUENCE DESCRIPTION: SEQ ID NO:161:

Xaa Glu Val Asp Gly Ile Asp Pro Xaa Gly Tyr
1               5                   10

(2) INFORMATION FOR SEQ ID NO:162:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
                /note= "Xaa = fluorphore 1 linked to the alpha-amino
                group of Pro"

(ix) FEATURE:
        (A) NAME/KEY: Modified-site
        (B) LOCATION: 10
        (D) OTHER INFORMATION: /product= "OTHER"
                /note= "Xaa = fluorophore 1 linked to the epsilon-amino
                group of Lys"

(xi) SEQUENCE DESCRIPTION: SEQ ID NO:162:

Xaa Asp Glu Val Asp Gly Ile Asp Pro Xaa Gly Tyr
1               5                   10

(2) INFORMATION FOR SEQ ID NO:163:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "Xaa = 9-fluorenylmethoxycarbonyl (Fmoc) group
                    attached to the epsilon-amino group and
                    5'-carboxytetramethylrhodamine attached to
                    the alpha-amino group of Lys"

(ix) FEATURE:
            (A) NAME/KEY: Modified-site
            (B) LOCATION: 6
            (D) OTHER INFORMATION: /product= "Nle"

(ix) FEATURE:
            (A) NAME/KEY: Modified-site
            (B) LOCATION: 10
            (D) OTHER INFORMATION: /product= "OTHER"
                /note= "Xaa = 5'-carboxytetramethylrhodamine attached to
                    the epsilon-amino group of Lys"

(xi) SEQUENCE DESCRIPTION: SEQ ID NO:163:

Xaa Asp Ala Ile Pro Xaa Ser Ile Pro Xaa Gly Tyr
1               5                   10

(2) INFORMATION FOR SEQ ID NO:164:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = 5'-carboxytetramethylrhodamine attached to
                the epsilon-amino group of Lys"

(ix) FEATURE:
        (A) NAME/KEY: Modified-site
        (B) LOCATION: 6
        (D) OTHER INFORMATION: /product= "Nle"

(ix) FEATURE:
        (A) NAME/KEY: Modified-site
        (B) LOCATION: 10
        (D) OTHER INFORMATION: /product= "OTHER"
            /note= "Xaa = 5'-carboxytetramethylrhodamine attached to
                the epsilon-amino group of Lys"

(xi) SEQUENCE DESCRIPTION: SEQ ID NO:164:

Xaa Asp Ala Ile Pro Xaa Ser Ile Pro Xaa Gly Tyr
1               5                   10

(2) INFORMATION FOR SEQ ID NO:165:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide

```
    (ix) FEATURE:
         (A) NAME/KEY: Modified-site
         (B) LOCATION: 1
         (D) OTHER INFORMATION: /product= "OTHER"
             /note= "Xaa - 9-fluoenylmethoxycarbonyl (Fmoc) group
             attached to the alpha-amino group of Asp"

(ix) FEATURE:
         (A) NAME/KEY: Modified-site
         (B) LOCATION: 5
         (D) OTHER INFORMATION: /product= "Nle"

(ix) FEATURE:
         (A) NAME/KEY: Modified-site
         (B) LOCATION: 9
         (D) OTHER INFORMATION: /product= "OTHER"
             /note= "Xaa = 5'-carboxytetramethylrhodamine attached to
             the epsilon-amino group of Lys"

(xi) SEQUENCE DESCRIPTION: SEQ ID NO:165:

Xaa Ala Ile Pro Xaa Ser Ile Pro Xaa Gly Tyr
1               5                   10

(2) INFORMATION FOR SEQ ID NO:166:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /note= "Xaa = 9-fluorenylmethoxycarbonyl (Fmoc) group
             attached to the alpha-amino group and
             5'-carboxytetramethylrhodamine attached to the
             epsilon-amino group of Lys"

(ix) FEATURE:
         (A) NAME/KEY: Modified-site
         (B) LOCATION: 3
         (D) OTHER INFORMATION: /product= "Aib"

(ix) FEATURE:
         (A) NAME/KEY: Modified-site
         (B) LOCATION: 12
         (D) OTHER INFORMATION: /product= "OTHER"
             /note= "Xaa = 5'-carboxytetramethylrhodamine attached to
             the epsilon-amino group of Lys"

(xi) SEQUENCE DESCRIPTION: SEQ ID NO:166:

Xaa Asp Xaa Asp Glu Val Asp Gly Ile Asp Pro Xaa Gly Tyr
1               5                   10

(2) INFORMATION FOR SEQ ID NO:167:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /note= "Xaa = 5'-carboxytetramethylrhodamine attached to
             the epsilon-amino group of Lys"
```

```
    (ix) FEATURE:
         (A) NAME/KEY: Modified-site
         (B) LOCATION: 3
         (D) OTHER INFORMATION: /product= "Aib"

(ix) FEATURE:
         (A) NAME/KEY: Modified-site
         (B) LOCATION: 12
         (D) OTHER INFORMATION: /product= "OTHER"
             /note= "Xaa = 5'-carboxytetramethylrhodamine attached to
             the epsilon-amino group of Lys"

(xi) SEQUENCE DESCRIPTION: SEQ ID NO:167:

Xaa Asp Xaa Asp Glu Val Asp Gly Ile Asp Pro Xaa Gly Tyr
1               5                   10

(2) INFORMATION FOR SEQ ID NO:168:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /note= "Xaa = 9-fluorenylmethoxycarbonyl (Fmoc) group
             attached to the alpha-amino group and
             5'-carboxytetramethylrhodamine attached to
             the epsilon-amino group of Lys"

(ix) FEATURE:
         (A) NAME/KEY: Modified-site
         (B) LOCATION: 3
         (D) OTHER INFORMATION: /product= "Aib"

(ix) FEATURE:
         (A) NAME/KEY: Modified-site
         (B) LOCATION: 12
         (D) OTHER INFORMATION: /product= "OTHER"
             /note= "Xaa = 5'-carboxytetramethylrhodamine attached to
             the epsilon-amino group of Lys"

(xi) SEQUENCE DESCRIPTION: SEQ ID NO:168:

Xaa Asp Xaa Asp Glu Val Asn Gly Ile Asp Pro Xaa Gly Tyr
1               5                   10

(2) INFORMATION FOR SEQ ID NO:169:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /note= "Xaa = 5'-carboxytetramethylrhodamine attached to
             the epsilon-amino group of Lys"

(ix) FEATURE:
         (A) NAME/KEY: Modified-site
         (B) LOCATION: 3
         (D) OTHER INFORMATION: /product= "Aib"
```

```
    (ix) FEATURE:
          (A) NAME/KEY: Modified-site
          (B) LOCATION: 12
          (D) OTHER INFORMATION: /product= "OTHER"
              /note= "Xaa = 5'-carboxytetramethylrhodamine attached to
              the epsilon-amino group of Lys"

(xi) SEQUENCE DESCRIPTION: SEQ ID NO:169:

Xaa Asp Xaa Asp Glu Val Asn Gly Ile Asp Pro Xaa Gly Tyr
1               5                   10

(2) INFORMATION FOR SEQ ID NO:170:

(i) SEQUENCE CHARACTERISTICS:
          (A) LENGTH: 13 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
              /note= "Xaa = 9-fluorenymethoxycarbonyl (Fmoc) group
              attached to the alpha-amino group and
              5'-carboxytetramethylrhodamine attached to the
              epsilon-amino group of Lys"

(ix) FEATURE:
          (A) NAME/KEY: Modified-site
          (B) LOCATION: 3
          (D) OTHER INFORMATION: /product= "Aib"

(ix) FEATURE:
          (A) NAME/KEY: Modified-site
          (B) LOCATION: 11
          (D) OTHER INFORMATION: /product= "OTHER"
              /note= "Xaa = 5'-carboxytetramethylrhodamine attached to
              the epsilon-amino group of Lys"

(xi) SEQUENCE DESCRIPTION: SEQ ID NO:170:

Xaa Asp Xaa Glu Val Asp Gly Ile Asp Pro Xaa Gly Tyr
1               5                   10

(2) INFORMATION FOR SEQ ID NO:171:

(i) SEQUENCE CHARACTERISTICS:
          (A) LENGTH: 13 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
              /note= "Xaa = 5'-carboxytetramethylrhodamine attached to
              the epsilon-amino group of Lys"

(ix) FEATURE:
          (A) NAME/KEY: Modified-site
          (B) LOCATION: 4
          (D) OTHER INFORMATION: /product= "Aib"

(ix) FEATURE:
          (A) NAME/KEY: Modified-site
          (B) LOCATION: 11
          (D) OTHER INFORMATION: /product= "OTHER"
              /note= "Xaa = 5'-carboxytetramethylrhodamine attached to
              the epsilon-amino group of Lys"
```

(xi) SEQUENCE DESCRIPTION: SEQ ID NO:171:

Xaa Asp Tyr Xaa Ala Asp Gly Ile Asp Pro Xaa Gly Tyr
1               5                   10

(2) INFORMATION FOR SEQ ID NO:172:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = 9-fluorenylmethoxycarbonyl (Fmoc) group
            attached to the alph-amino and
            5'-carboxytetramethylrhodamine attached to the
            epsilon-amino group of Lys"

(ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 14
        (D) OTHER INFORMATION: /product= "OTHER"
            /note= "Xaa = 5'-carboxytetramethylrhodamine attached to
            the epsilon-amino group of Lys"

(xi) SEQUENCE DESCRIPTION: SEQ ID NO:172:

Xaa Asp Xaa Gly Asp Glu Val Asp Gly Ile Asp Gly Pro Xaa Gly Tyr
1               5                   10                  15

(2) INFORMATION FOR SEQ ID NO:173:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = 9-fluorenylmethoxycarbonyl (Fmoc) group
            attached to the alpha-amino group and
            5'-carboxytetramethylrhodamine attached to the
            epsilon-amino group of Lys"

(ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 14
        (D) OTHER INFORMATION: /product= "Acp"

(ix) FEATURE:
        (A) NAME/KEY: Modified-site
        (B) LOCATION: 16
        (D) OTHER INFORMATION: /product= "OTHER"
            /note= "Xaa = 5'-carboxytetramethylrhodamine attached to
            the epsilon-amino group of Lys"

(xi) SEQUENCE DESCRIPTION: SEQ ID NO:173:

Xaa Asp Xaa Xaa Gly Asp Glu Val Asp Gly Ile Asp Gly Xaa Pro Xaa
1               5                   10                  15

Gly Tyr (2) INFORMATION FOR SEQ ID NO:174:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = benzyloxycarbonyl (Z) group attached to the
            alpha-amino group and 5'-carboxytetramethylrhodamine
            attached to the epsilon-amino group of Lys"

(ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 4
        (D) OTHER INFORMATION: /product= "Acp"

(ix) FEATURE:
        (A) NAME/KEY: Modified-site
        (B) LOCATION: 14
        (D) OTHER INFORMATION: /product= "Acp"

(ix) FEATURE:
        (A) NAME/KEY: Modified-site
        (B) LOCATION: 16
        (D) OTHER INFORMATION: /product= "OTHER"
            /note= "Xaa = 5'-carboxytetramethylrhodamine attached to
            the epsilon-amino group of Lys"

(xi) SEQUENCE DESCRIPTION: SEQ ID NO:174:

Xaa Asp Xaa Xaa Gly Asp Glu Val Asp Gly Ile Asp Gly Xaa Pro Xaa
1               5                   10                  15

Gly Tyr (2) INFORMATION FOR SEQ ID NO:175:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = 9-fluorenylmethoxycarbonyl (Fmoc) group
            attached to the alpha-amino group and
            5'-carboxytetramethylrhodamine attached to the
            epsilon-amino group of Lys"

(ix) FEATURE:
        (A) NAME/KEY: Modified-site
        (B) LOCATION: 4
        (D) OTHER INFORMATION: /product= "Aib"

(ix) FEATURE:
        (A) NAME/KEY: Modified-site
        (B) LOCATION: 11
        (D) OTHER INFORMATION: /product= "OTHER"
            /note= "Xaa = 5'-carboxytetramethylrhodamine attached to
            the epsilon-amino group of Lys"

(xi) SEQUENCE DESCRIPTION: SEQ ID NO:175:

Xaa Asp Tyr Xaa Ala Asp Gly Ile Asp Pro Xaa Gly Tyr
1               5                   10

(2) INFORMATION FOR SEQ ID NO:176:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = 5'-carboxytetramethylrhodamine attached to
            the epsilon-amino group of Lys"

(ix) FEATURE:
        (A) NAME/KEY: Modified-site
        (B) LOCATION: 3
        (D) OTHER INFORMATION: /product= "Aib"

(ix) FEATURE:
        (A) NAME/KEY: Modified-site
        (B) LOCATION: 11
        (D) OTHER INFORMATION: /product= "OTHER"
            /note= "Xaa = 5'-carboxytetramethylrhodamine attached to
            the epsilon-amino group of Lys"

(xi) SEQUENCE DESCRIPTION: SEQ ID NO:176:

Xaa Asp Xaa Glu Val Asp Gly Ile Asp Pro Xaa Gly Tyr
1               5                   10

(2) INFORMATION FOR SEQ ID NO:177:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /note= "Xaa = aminofluoromethyl coumarin (AFC) attached
            to Asp"

-continued (xi) SEQUENCE DESCRIPTION: SEQ ID NO:177:

Asp Glu Val Xaa
1

(2) INFORMATION FOR SEQ ID NO:178:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:178:

Gly Asp Glu Val Asp Gly Ile Asp
1               5

(2) INFORMATION FOR SEQ ID NO:179:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(xi) SEQUENCE DESCRIPTION: SEQ ID NO:179:

Lys Asp Xaa Gly
1

(2) INFORMATION FOR SEQ ID NO:180:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(ix) FEATURE:
            (A) NAME/KEY: Modified-site
            (B) LOCATION: 4
            (D) OTHER INFORMATION: /product= "Acp"

(xi) SEQUENCE DESCRIPTION: SEQ ID NO:180:

Lys Asp Xaa Xaa Gly
1               5

(2) INFORMATION FOR SEQ ID NO:181:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide

```
        (ix) FEATURE:
              (A) NAME/KEY: Modified-site
              (B) LOCATION: 2
              (D) OTHER INFORMATION: /product= "Acp"

(xi) SEQUENCE DESCRIPTION: SEQ ID NO:181:

Gly Xaa Pro Lys
1

(2) INFORMATION FOR SEQ ID NO:182:

(i) SEQUENCE CHARACTERISTICS:
              (A) LENGTH: 5 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:182:

Thr Gly Arg Thr Gly
1               5

(2) INFORMATION FOR SEQ ID NO:183:

(i) SEQUENCE CHARACTERISTICS:
              (A) LENGTH: 7 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:183:

Asp Glu Val Asp Gly Ile Asp
1               5

(2) INFORMATION FOR SEQ ID NO:184:

(i) SEQUENCE CHARACTERISTICS:
              (A) LENGTH: 7 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:184:

Asp Glu Val Asn Gly Ile Asp
1               5

(2) INFORMATION FOR SEQ ID NO:185:

(i) SEQUENCE CHARACTERISTICS:
              (A) LENGTH: 6 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:185:

Glu Val Asp Gly Ile Asp
1               5
```

```
(2) INFORMATION FOR SEQ ID NO:186:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:186:

Ala Asp Gly Ile Asp
1               5

(2) INFORMATION FOR SEQ ID NO:187:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:187:

Ala Ile Pro Met Ser Ile
1               5

(2) INFORMATION FOR SEQ ID NO:188:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:188:

Gly Asp Glu Val Asp Gly Ile Asn
1               5

(2) INFORMATION FOR SEQ ID NO:189:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:189:

Gly Asn Glu Val Asp Gly Ile Asp
1               5

(2) INFORMATION FOR SEQ ID NO:190:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:190:

Gly Asn Glu Val Asp Gly Ile Asn
1               5
```

(2) INFORMATION FOR SEQ ID NO:191:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = tetrahydroisoquinoline-3-carboxylic acid"

(xi) SEQUENCE DESCRIPTION: SEQ ID NO:191:

Xaa Asp Glu Val Asp Gly Ile Asp
1               5

(2) INFORMATION FOR SEQ ID NO:192:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:192:

Trp Asp Glu Val Asp Gly Ile Asp
1               5

(2) INFORMATION FOR SEQ ID NO:193:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:193:

Tyr Val Ala Asp Gly Ile Asp
1               5

(2) INFORMATION FOR SEQ ID NO:194:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:194:

Tyr Val Ala Asp Gly Ile Asn
1               5

(2) INFORMATION FOR SEQ ID NO:195:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:195:

Tyr Val Ala Asn Gly Ile Asn
1               5

(2) INFORMATION FOR SEQ ID NO:196:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:196:

Leu Val Glu Ile Asp Asn Gly
1               5

(2) INFORMATION FOR SEQ ID NO:197:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:197:

Leu Val Glu Ile Asn Asn Gly
1               5

(2) INFORMATION FOR SEQ ID NO:198:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:198:

Gly Ile Glu Thr Asp Ser Gly Val Asp Asp
1               5                   10

(2) INFORMATION FOR SEQ ID NO:199:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:199:

Gly Ile Glu Thr Asn Ser Gly Val Asp Asp
1               5                   10

(2) INFORMATION FOR SEQ ID NO:200:

(i) SEQUENCE CHARACTERISTICS:
            (A) LENGTH: 8 amino acids
            (B) TYPE: amino acid
            (C) STRANDEDNESS:
            (D) TOPOLOGY: linear

```
    (ii) MOLECULE TYPE: peptide (xi) SEQUENCE DESCRIPTION: SEQ ID NO:200:

Gly Ile Glu Thr Asn Ser Gly Val
1               5

(2) INFORMATION FOR SEQ ID NO:201:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:201:

Gly Ile Glu Thr Asp Ser Gly Val
1               5

(2) INFORMATION FOR SEQ ID NO:202:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:202:

Gly Ser Glu Ser Met Asp Ser Gly Ile Ser Leu Asp
1               5                   10

(2) INFORMATION FOR SEQ ID NO:203:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:203:

Gly Ser Glu Ser Met Asp Ser Gly
1               5

(2) INFORMATION FOR SEQ ID NO:204:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:204:

Asp Val Val Cys Asp Ser Met Ser
1               5

(2) INFORMATION FOR SEQ ID NO:205:

(i) SEQUENCE CHARACTERISTICS:
        (A) LENGTH: 7 amino acids
        (B) TYPE: amino acid
```

```
            (C) STRANDEDNESS:
            (D) TOPOLOGY: linear (ii) MOLECULE TYPE: peptide (xi) SEQUENCE DESCRIPTION: SEQ ID NO:205:

Glu Asp Val Val Cys Cys Ser
1               5

(2) INFORMATION FOR SEQ ID NO:206:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:206:

Asp Val Val Cys Cys Ser Met
1               5

(2) INFORMATION FOR SEQ ID NO:207:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:207:

Asp Val Val Cys Asp Ser Met
1               5

(2) INFORMATION FOR SEQ ID NO:208:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:208:

Val Cys Cys Ser Met
1               5

(2) INFORMATION FOR SEQ ID NO:209:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:209:

Val Cys Asp Ser Met
1               5
```

```
(2) INFORMATION FOR SEQ ID NO:210:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:210:

Asp Glu Met Glu Glu Cys Ser Gln His Leu
1               5                   10

(2) INFORMATION FOR SEQ ID NO:211:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:211:

Asp Glu Met Glu Glu Cys Pro Gln His Leu
1               5                   10

(2) INFORMATION FOR SEQ ID NO:212:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:212:

Glu Met Glu Glu Cys Ser Gln His Leu
1               5

(2) INFORMATION FOR SEQ ID NO:213:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:213:

Glu Met Glu Glu Cys Pro Gln His Leu
1               5

(2) INFORMATION FOR SEQ ID NO:214:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:214:

Glu Met Glu Glu Asp Ser Gln His Leu
1               5
```

(2) INFORMATION FOR SEQ ID NO:215:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:215:

Val Met Thr Gly Arg Thr Gly
1           5

(2) INFORMATION FOR SEQ ID NO:216:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:216:

Val Met Thr Gly Arg Gly
1           5

(2) INFORMATION FOR SEQ ID NO:217:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:217:

Val Met Thr Gly Arg Val Gly
1           5

(2) INFORMATION FOR SEQ ID NO:218:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:218:

Val Met Thr Gly Arg Ala Gly
1           5

(2) INFORMATION FOR SEQ ID NO:219:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:219:

Ser Glu Val Asn Leu Asp Ala Glu Phe
1           5

(2) INFORMATION FOR SEQ ID NO:220:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:220:

Ser Glu Val Lys Leu Asp Ala Glu Phe
1               5

(2) INFORMATION FOR SEQ ID NO:221:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:221:

Ser Glu Val Lys Met Asp Ala Glu Phe
1               5

(2) INFORMATION FOR SEQ ID NO:222:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:222:

Ser Glu Val Lys Met Asp Asp Glu Phe
1               5

(2) INFORMATION FOR SEQ ID NO:223:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:223:

Ser Glu Val Asn Leu Asp Asp Glu Phe
1               5

(2) INFORMATION FOR SEQ ID NO:224:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:224:

Gly Val Val Ile Ala Thr Val Ile Val Ile Thr
1               5                  10

(2) INFORMATION FOR SEQ ID NO:225:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:225:

Tyr Gly Val Val Ile Ala Thr Val Ile Val Ile Thr
1               5                  10

(2) INFORMATION FOR SEQ ID NO:226:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:226:

Val Ile Ala Thr Val Ile
1               5

(2) INFORMATION FOR SEQ ID NO:227:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:227:

Tyr Gly Val Val Ile Ala
1               5

(2) INFORMATION FOR SEQ ID NO:228:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:228:

Gln Gln Leu Leu Asn His
1               5

(2) INFORMATION FOR SEQ ID NO:229:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:229:

Ser Ile Gln Tyr Thr Tyr
1               5

(2) INFORMATION FOR SEQ ID NO:230:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:230:

Ser Ser Gln Tyr Ser Asn
1               5

(2) INFORMATION FOR SEQ ID NO:231:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:231:

Ser Ser Ile Tyr Ser Gln
1               5

FLUOROGENIC PEPTIDES FOR THE DETECTION OF PROTEASE ACTIVITY

CROSS-REFERENCE TO RELATED APPLICATIONS

[Not Applicable]

FIELD OF THE INVENTION

This invention pertains to a class of novel fluorogenic compositions whose fluorescence level increases in the presence active proteases. These fluorogenic protease indicators typically fluoresce at visible wavelengths and are thus highly useful for the detection and localization of protease activity in biological samples.

BACKGROUND OF THE INVENTION

Proteases represent a number of families of proteolytic enzymes that catalytically hydrolyze peptide bonds. Principal groups of proteases include metalloproteases, serine porteases, cysteine proteases and aspartic proteases. Proteases, in particular serine proteases, are involved in a number of physiological processes such as blood coagulation, fertilization, inflammation, hormone production, the immune response and fibrinolysis.

Numerous disease states are caused by and can be characterized by alterations in the activity of specific proteases and their inhibitors. For example emphysema, arthritis, thrombosis, cancer metastasis and some forms of hemophilia result from the lack of regulation of serine protease activities (see, for example, *Textbook of Biochemistry with Clinical Correlations*, John Wiley and Sons, Inc. N.Y. (1993)). In case of viral infection, the presence of viral proteases have been identified in infected cells. Such viral proteases include, for example, HIV protease associated with AIDS and NS3 protease associated with Hepatitis C. These viral proteases play a critical role in the virus life cycle.

Proteases have also been implicated in cancer metastasis. Increased synthesis of the protease urokinase has been correlated with an increased ability to metastasize in many cancers. Urokinase activates plasmin from plasminogen which is ubiquitously located in the extracellular space and its activation can cause the degradation of the proteins in the extracellular matrix through which the metastasizing tumor cells invade. Plasmin can also activate the collagenases thus promoting the degradation of the collagen in the basement membrane surrounding the capillaries and lymph system thereby allowing tumor cells to invade into the target tissues (Dano, et al. (1985) *Adv. Cancer. Res.*, 44: 139.

Clearly measurement of changes in the activity of specific proteases is clinically significant in the treatment and management of the underlying disease states. Proteases, however, are not easy to assay. Typical approaches include ELISA using antibodies that bind the protease or RIA using various labeled substrates. With their natural substrates assays are difficult to perform and expensive. With currently available synthetic substrates the assays are expensive, insensitive and nonselective. In addition, many "indicator" substrates require high quantities of protease which results, in part, in the self destruction of the protease.

Recent approaches to protease detection rely on a cleavage-induced spectroscopic change in a departing chromogen or fluorogen located in the P1' position (the amino acid position on the carboxyl side of the cleavable peptide bond) (see, for example U.S. Pat. Nos. 4,557,862 and 4,648,893). However, many proteases require two or four amino acid residues on either side of the scissile bond for recognition of the protease (a specific protease may require up to 6 amino acid residues) and thus, these approaches lack protease specificity.

Recently however, fluorogenic indicator compositions have been developed in which a "donor" fluorophore is joined to an "acceptor" chromophore by a short bridge containing a (7 amino acid) peptide that is the binding site for an HIV protease and linkers joining the fluorophore and chromophore to the peptide (Wang et al. (1990) *Tetra. Letts.* 45: 6493–6496). The signal of the donor fluorophore was quenched by the acceptor chromophore through a process believed to involve resonance energy transfer (RET). Cleavage of the peptide resulted in separation of the chromophore and fluorophore, removal of the quench and a subsequent signal was measured from the donor fluorophore.

Unfortunately, the design of the bridge between the donor and the acceptor led to relatively inefficient quenching limiting the sensitivity of the assay. In addition, the chromophore absorbed light in the ultraviolet range reducing the sensitivity for detection in biological samples which typically contain molecules that absorb strongly in the ultraviolet.

Clearly fluorogenic protease indicators that show a high signal level when cleaved, and a very low signal level when intact, that show a high degree of protease specificity, and that operate exclusively in the visible range thereby rendering them suitable for use in biological samples are desirable. The compositions of the present invention provide these and other benefits.

SUMMARY OF THE INVENTION

The present invention provides for novel reagents whose fluorescence increases in the presence of particular proteases. These fluorogenic protease indicators provide a high intensity fluorescent signal at a visible wavelength when they are digested by a protease. Because of their high fluorescence signal in the visible wavelengths, these protease indicators are particularly well suited for detection of protease activity in biological samples, in particular, in frozen tissue sections. The measurement can be carried out using a fluorescence microscope for histological samples and using a flow cytometer for cell suspension samples. Hence, the fluorogenic compositons of this invention allow detection of intracellular protease activity.

The fluorogenic protease indicators of the present invention are compositions suitable for detection of the activity of a protease. These compositions have the general formula:

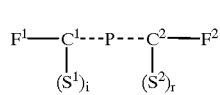

I in which P is a peptide comprising a protease binding site for said protease consisting of 2 to about 15, preferably 2 to about 12, preferably 2 to about 10, preferably 2 to about 8, 2 to about 6, or 2 to about 4 amino acids; $F^1$ and $F^2$ are fluorophores; $S^1$ and $S^2$ are peptide spacers ranging in length from 1 to about 50 amino acids; n and k are independently 0 or 1; and $C^1$ and $C^2$ are conformation determining regions comprising peptides ranging in length from 1 to about 8, amino acids, more preferably from 1 to about 6 amino acids. The conformation determining regions each introduce a bend into the composition or otherwise restrict the degrees of freedom of the peptide backbone, thereby juxtaposing the fluorophores with a separation of less than about 100 Å. When either of the spacers ($S^1$ and $S^2$) are present they are linked to the protease binding site by a peptide bond to the alpha carbon of the terminal amino acid. Thus, when i is 1, $S^1$ is joined to $C^1$ by a peptide bond through a terminal α-amino group of $C^1$, and when r is 1, $S^2$ is joined to $C^2$ by a peptide bond through a terminal alpha carboxyl group of $C^2$.

The amino acid residues comprising a protease binding site are, by convention, numbered relative to the peptide bond hydrolyzed by a particular protease. Thus the first amino acid residue on the amino side of the cleaved peptide bond is designated $P_1$ while the first amino acid residue on the carboxyl side of the cleaved peptide bond is designated $P_1'$. The numbering of the residues increases with distance away from the hydrolyzed peptide bond. Thus a four amino acid protease binding region would contain amino acids designated:

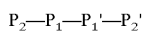

$$P_2-P_1-P_1'-P_2'$$

and the protease would cleave the binding region between $P_1$ and $P_1'$.

In particularly preferred embodiments, the fluorogenic compositions of this invention are compositions of Formula II and Formula V as described herein. Preferred fluorophores have conformation determining regions and, optionally, spacers as described herein. In a most preferred embodiment, the compositions bear a single species of fluorophore. Fluorophores suitable for these "homolabeled" compositions include fluorophores that form H-type dimers. Particularly preferred fluorphores have an excitation wavelength between about 315 nm and about 700 nm.

In another embodiment, this invention provides methods of detecting the activity of a protease. The methods involve contacting the protease with one or more of the protease indicators described herein. In a particularly preferred embodiment, the "contacting" is in a histological section or in a cell suspension or culture derived from a bioligical sample selected from the group consisting of a tissue, blood, urine, saliva, or other biofluid, lymph, biopsy. The detection method can include a method selected from the group consisting of fluorescence microscopy, fluorescence microplate reader, flow cytometry, fluorometry, absorption spectroscopy.

In the compositions $F^1$ may be 5- and/or 6-carboxytetramethylrhodamine; and $F^2$ may be rhodamine X acetamide. These compositions may be conjugated to a solid support or to a lipid including membrane lipids or liposomes.

In another embodiment, any of the compositions described above may be used in a method for detecting protease activity in a sample. The sample may be a sample of "stock" protease, such as is used in research or industry, or it may be a biological sample. Thus, this invention provides for a method of detecting protease activity in a sample by contacting the sample with any of the compositions described above and then detecting a change in fluorescence of the fluorogenic composition where an increase in fluorescence indicates protease activity. The sample is preferably a biological sample which may include biological fluids such as sputum or blood, tissue samples such as biopsies or sections, and cell samples either as biopsies or in culture. Particularly preferred are tissue sections, cultured cells, cultured tissues, and the like.

This invention also provides a method of detecting a change in conformation of a molecule. The method involves:

1) providing a first molecule having attached thereto a first fluorophore and a second fluorophore wherein the first fluorphore and second fluorophre are the same species of fluorophore, and the fluorophores are juxtaposed at a distance sufficient for the interaction of said fluorophores to detectably reduce the fluorescence intensity of each of said flurophores as compared to the fluoresence intensity of a single fluorophore attached to the molecule at the same location; and 2) detecting the change in fluorescence as the spacing between said fluorophores is increased by a change in conformation of the molecule. Alternatively the change in fluorescence as the relative orientation of the fluorophore is altered by a change in conformation of the molecule may be detected. Preferred fluorophores are capable of forming H-type dimers before the change in conformation. In a preferred embodiment the fluorophores are situated at a distance of less than about 10 angstroms from each other prior to the change in conformation. Particularly preferred fluorophores include the fluorophores described herein. In one embodiment, the change in conformation is cleavage of the molecule into two different molecules each bearing one of the fluorophores. In another embodiment the change in conformation is caused by binding of a target molecule to said first molecule. In one embodiment, the first molecule is a nucleic acid and the change in conformation is produced by hybridization of the nucleic acid to a second nucleic acid or by binding of the nucleic acid to a transcription factor. In another embodiment, the first molecule is a polysaccharide and the change in conformatio nis produced by bindign of an oligosaccharide bindng molecule, e.g., a lecithin binding protein. Preferred "backbone" molecules for this method include a nucleic acid, a polysaccharide, a peptide, a lipid, a protein, a phospholipid, a glycolipid, a glycoprotein, a steroid, or a polymer containign a pH or thiol-sensitive bond where the fluorophores attachment sites sadwich this bond. Where the backbone molecule is a nucleic acid, the change in conformation can be produced by hybridization of the nucleic acid to another nucleic acid or by cleavage of the nucleic acid (e.g., by a restriction endonuclease or a ribozyme). Also the change in conformation can be produced by formation of a complex between the labeled oligonucleotide and a nucleotide binding protein. Where the backbone molecule is a peptide, polysaccharide or a lipid, the change in conformation can be produced by cleavage of the backbone molecule or by complex formation between the backbone molecule and its bindign molecule such as an antibody, receptor, sugar bindign protein, or lipid binding protein.

This invention also provides a fluorogenic composition for the detection of a change in conformation of said composition. In one embodiment, the fluorogenic composition comprising a molecule having attached thereto a first fluorophore and a second fluorophore wherein said first fluorphore and said second fluorophre are the same species of fluorophore, and said fluorophores are juxtaposed at a distance sufficient for the interaction of said fluorophores to detectably reduce the fluorescence intensity of each of said flurophores as compared to the fluoresence intensity of each individual fluorophore attached to the molecule at the same location. The fluorophores are preferably fluorphores that form H-type dimers.

In still yet another embodiment, this invention provides a method of delivering a molecule into a cell. The method involves providing the molecule attached to at least two fluorophore molecules and a hydrophobic group; and contacting the cell with the molecule whereby the molecule enters the cell. In one embodiment, the method involves providign the molecuel attached to at least two largely flat hydrophobic fluorophore molecules and a hydrophobic group. Preferred molecules include a polypeptide, a nucleic acid, a lipid, an oligosaccharide. Suitable fluorophores and hydrophobic groups are described herein. Preferred cells include mammalian cells.

Definitions

The term "protease binding site" is used herein to refers to an amino acid sequence that is characteristically recognized and cleaved by a protease. The protease binding site contains a peptide bond that is hydrolyzed by the protease and the amino acid residues joined by this peptide bond are said to form the cleavage site. These amino acids are designated $P_1$ and $P_1'$ for the residues on the amino and carboxyl sides of the hydrolyzed bond respectively.

A fluorophore is a molecule that absorbs light at a characteristic wavelength and then re-emits the light most typically at a characteristic different wavelength. Fluorophores are well known to those of skill in the art and include, but are not limited to rhodamine and rhodamine derivatives, fluorescein and fluorescein derivatives, coumarins and chelators with the lanthanide ion series. A fluorophore is distinguished from a chromophore which absorbs, but does not characteristically re-emit light.

"Peptides" and "polypeptides" are chains of amino acids whose α carbons are linked through peptide bonds formed by a condensation reaction between the a carboxyl group of one amino acid and the amino group of another amino acid. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free a-amino group on an amino acid at the amino terminal of a peptide or to the a-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include peptide mimetics such as amino acids joined by an ether as opposed to an amide bond.

The polypeptides described herein are written with the amino terminus at the left and the carboxyl terminus at the right. The amino acids comprising the peptide components of this invention are numbered with respect to the protease cleavage site, with numbers increasing consecutively with distance in both the carboxyl and amino direction from the cleavage site. Residues on the carboxyl site are either notated with a "'" as in $P_1'$, or with a letter and superscript indicating the region in which they are located. The "'" indicates that residues are located on the carboxyl side of the cleavage site.

The term "residue" or "amino acid" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

The term "domain" or "region" refers to a characteristic region of a polypeptide. The domain may be characterized by a particular structural feature such as a β turn, an alpha helix, or a β pleated sheet, by characteristic constituent amino acids (e.g. predominantly hydrophobic or hydrophilic amino acids, or repeating amino acid sequences), or by its localization in a particular region of the folded three dimensional polypeptide. As used herein, a region or domain is composed of a series of contiguous amino acids.

The terms "protease activity" or "activity of a protease" refer to the cleavage of a peptide by a protease. Protease activity comprises the "digestion" of one or more peptides into a larger number of smaller peptide fragments. Protease activity of particular proteases may result in hydrolysis at particular peptide binding sites characteristically recognized by a particular protease. The particular protease may be characterized by the production of peptide fragments bearing particular terminal amino acid residues.

The amino acids referred to herein are described by shorthand designations as shown in Table 1.

TABLE 1

Amino acid nomenclature.

| Name | Abbreviation | |
|---|---|---|
| | 3 Letter | 1 Letter |
| Alanine | Ala | A |
| βAlanine (NH$_2$—CH$_2$—CH$_2$—COOH) | βAla | |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| episilon-aminocaproic acid (NH$^2$—(CH$_2$)$_5$—COOH) | Ahx | J |
| 4-aminobutanoic acid (NH$_2$—(CH$_2$)$_3$—COOH) | gAbu | |
| tetrahydroisoquinoline-3-carboxylic acid | | O |
| Lys(N(epsilon)-trifluoroacetyl) | | K[TFA] |
| α-aminoisobutyric acid | Aib | B |

Other abbreviations used herein include "Fm" for Fmoc (9-fluorenylmethyoxycarbonyl) group, "Ac" for N(alpha)-acetyl group, "daa" where "d" indicates the d isomer of the aa, and "Z" for benzyloxycarbonyl group.

BRIEF DESCRIPTION OF THE DRAWINGS

FIG. 1A: HPLC before the addition of elastase showing the late eluting peak representing the intact indicator molecule. FIG. 1B: HPLC after the addition of elastase with detection at 550 nm where both fluorophores absorb. FIG. 1C HPLC after the addition of elastase with detection at 580 nm where F$^2$ absorbs maximally.

FIG. 4A: The fluorogenic protease indicator of FIG. 1. FIG. 4B: The peptide backbone of the fluorogenic protease of FIG. 1 singly labeled with each of the two fluorophores. D-NorFES-A is the $F^1$-Asp-Ala-Ile-Pro-Nle-Ser-Ile-Pro-Cys-$F^2$ (SEQ ID NO:1) protease indicator where $F^1$ is a donor fluorophore (5'-carboxytetramethylrhodamine (C2211) and $F^2$ is an acceptor fluorophore (rhodamine X acetamide (R492). D-NorFES and A-NorFES each designate a molecule having the same peptide backbone, but bearing only one of the two fluorophores.

DETAILED DESCRIPTION

Fluorogenic Indicators of Protease Activity

Figure 1A:
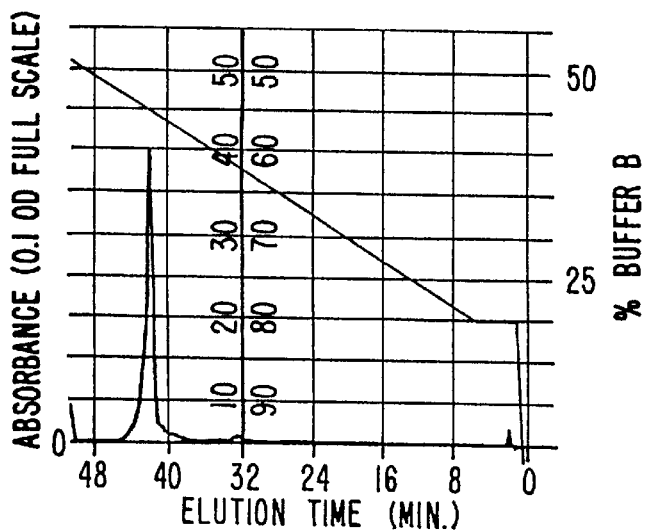
FIGS. 1A, 1B, and 1C show an HPLC analysis of the D-NorFES-A protease indicator (F$^1$-Asp-Ala-Ile-Pro-Nle-Ser-Ile-Pro-Cys-F$^2$) (SEQ ID NO:1) where F$^1$ is a donor (D) fluorophore (5'-carboxytetramethylrhodamine (C2211) and F$^2$ is an acceptor (A) fluorophore (rhodamine X acetamide (R492))) before and after the addition of elastase.

This invention provides for novel fluorogenic molecules useful for detecting protease activity in a sample. The fluorogenic protease indicators of the present invention generally comprise a fluorophore (donor) linked to an "acceptor" molecule by a peptide having an amino acid sequence that is recognized and cleaved by a particular protease. The donor fluorophore typically is excited by incident radiation at a particular wavelength which it then re-emits at a different (longer) wavelength. When the donor fluorophore is held in close proximity to the acceptor molecule, the acceptor absorbs the light re-emitted by the fluorophore thereby quenching the fluorescence signal of the donor molecule. The quench occurs whether the two fluorophores are different or the same species. Thus, in addition to peptides double labeled with two different fluorophores as shown in Example 1, peptides double labeled with the same fluorophore may also be used as protease indicators (see, e.g., Example 6). Cleavage of a well-designed (i.e. a peptide of this invention) joining the donor fluorophore and the acceptor results in separation of the two molecules, release of the quenching effect and increase in fluorescence.

In one basic application, the fluorogenic molecules of this invention may be used to assay the activity of purified protease made up as a reagent (e.g. in a buffer solution) for experimental or industrial use. Like many other enzymes, proteases may loose activity over time, especially when they are stored as their active forms. In addition, many proteases exist naturally in an inactive precursor form (e.g. a zymogen) which itself must be activated by hydrolysis of a particular peptide bond to produce the active form of the enzyme prior to use. Because the degree of activation is variable and because proteases may loose activity over time, it is often desirable to verify that the protease is active and to often quantify the activity before using a particular protease in a particular application.

Previous approaches to verifying or quantifying protease activity involve combining an aliquot of the protease with its substrate, allowing a period of time for digestion to occur and then measuring the amount of digested protein, most typically by HPLC. This approach is time consuming, utilizes expensive reagents, requires a number of steps and entails a considerable amount of labor. In contrast, the fluorogenic reagents of the present invention allow rapid determination of protease activity in a matter of minutes in a single-step procedure. An aliquot of the protease to be tested is simply added to, or contacted with, the fluorogenic reagents of this invention and the subsequent change in fluorescence is monitored (e.g., using a fluorimeter or a fluorescence microplate reader).

In addition to determining protease activity in "reagent" solutions, the fluorogenic compositions of the present invention may be utilized to detect protease activity in biological samples. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

Previously described fluorogenic protease indicators typically absorb light in the ultraviolet range (e.g., Wang et al., supra.). They are thus unsuitable for sensitive detection of protease activity in biological samples which typically contain constituents (e.g., proteins) that absorb in the ultraviolet range. In contrast, the fluorescent indicators of the present invention both absorb and emit in the visible range (400 nm to about 750 nm). These signals are therefore not readily quenched by, nor is activation of the fluorophores, that is, absorption of light, interfered with by background molecules; therefore they are easily detected in biological samples.

In addition, unlike previous fluorogenic protease indicators which often utilize a fluorophore and a quenching chromophore, the indicators of the present invention may utilize two fluorophores (i.e., fluorophore as both donor and acceptor) or the same two fluorophores effectively forming a ground-state dimer when joined by the one of the peptide backbones of this invention. Pairs of fluorophores may be selected that show a much higher degree of quenching than previously described chromophore/fluorophore combinations. In fact, previous compositions have been limited to relatively low efficiency fluorophores because of the small degree of quenching obtainable with the matching chromophore (Wang et al. supra.). In contrast, the fluorogenic protease indicators of this invention utilize high efficiency fluorophores and are able to achieve a high degree of quenching while providing a strong signal when the quench is released by cleavage of the peptide substrate. The high signal allows detection of very low levels of protease activity. Thus the fluorogenic protease indicators of this invention are particularly well suited for in situ detection of protease activity.

The fluorogenic protease indicators of the present have the general formula:

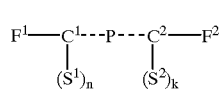

where P is a peptide comprising a protease binding site, $F^1$ and $F^2$ are fluorophores, $C^1$ and $C^2$ are conformation determining regions, and $S^1$ and $S^2$ are optional peptide spacers. $F^1$ may be the donor fluorophore while $F^2$ is the acceptor fluorophore, or conversely, $F^2$ may be the donor fluorophore while $F^1$ is the acceptor fluorophore, or $F^1$ and $F^2$ may be identical. The protease binding site provides an amino acid sequence (a peptide) that is recognized and cleaved by the protease whose activity the indicator is designed to reveal. The protease binding site is typically a peptide ranging in length from 2 amino acids to about 12 amino acids, 2 to about 10, 2 to about 8, 2 to about 6 or 2 to about 4 amino acids in length.

The conformation determining region is an amino acid sequence that introduces a bend into the molecule or otherwise restricts the degrees of freedom of the peptide backbone. The combined effect of the two conformation determining regions is to juxtapose the fluorophores attached to the amino and carboxyl termini of $C^1$ and $C^2$ respectively. The fluorophores are thus preferably positioned adjacent to each other at a distance less than about 100 angstroms. The fluorophores ($F^1$ and $F^2$) are typically conjugated directly to the conformation determining regions, although they may be joined by linkers. The optional spacers ($S^1$ and $S^2$) when present, are used to link the composition to a solid support or to anchor the composition to a component of a biological sample (e.g., to a cellular membrane).

The substantially conformation determining regions increases the protease specificity of the composition. The amino acid sequences comprising the conformation determining regions are typically less accessible to the enzyme due to steric hinderance with each other and with the attached fluorophores. Conversely, the protease binding site is relatively unobstructed by either the fluorophore or the conformational determining region and is thus readily accessible to the protease.

Protease Binding Site and Conformation Determining Regions

The protease binding site and conformation determining regions form a contiguous amino acid sequence (peptide). The protease binding site is an amino acid sequence that is recognized and cleaved by a particular protease. It is well known that various proteases cleave peptide bonds adjacent to particular amino acids. Thus, for example, trypsin cleaves peptide bonds following basic amino acids such as arginine and lysine and chymotrypsin cleaves peptide bonds following large hydrophobic amino acid residues such as tryptophan, phenylalanine, tyrosine and leucine. The serine protease elastase cleaves peptide bonds following small hydrophobic residues such as alanine.

A particular protease, however, will not cleave every bond in a protein that has the correct adjacent amino acid. Rather, the proteases are specific to particular amino acid sequences which serve as recognition domains for each particular protease. Without being bound by a particular theory, it is believed that a specific protease's preference for a particular cleavage site over many other potential sites in a folded globular protein may be largely determined by the potential cleavage sites' amino acid sequences and also their conformation and conformational flexibility.

Thus, for example, one obtains limited proteolysis products, e.g., ribonuclease-S (a noncovalent complex consisting of two polypeptide chains) from a single chain folded protein ribonuclease-A using a protease called subtilisin. Similarly, one obtains a two chain noncovalent complex, Staphylococal nuclease-T, from single chain Staphylococcal nuclease by trypsin digestion. Another example of a specific protease's preference for one substrate over others is the human fibroblast-type collagenase. This protease prefers type I over type III soluble collagen even though both substrates contain the same collagenase sensitive Gly-Ile or Gly-Leu bonds (see, e.g., Birkedal-Hansen et. al. (1993) *Crit. Rev. in Oral Biology and Medicine* 4:197–250).

Any amino acid sequence that comprises a recognition domain and can thus be recognized and cleaved by a protease is suitable for the "protease binding site" of the fluorogenic protease indicator compositions of this invention. Known protease substrate sequences and peptide inhibitors of proteases posses amino acid sequences that are recognized by the specific protease they are cleaved by or that they inhibit. Thus known substrate and inhibitor sequences provide the basic sequences suitable for use in the protease recognition region. A number of protease substrates and inhibitor sequences suitable for use as protease binding domains in the compositions of this invention are indicated in Table 2. One of skill will appreciate that this is not a complete list and that other protease substrates or inhibitor sequences may be used.

The amino acid residues comprising the protease binding site are, by convention, numbered relative to the peptide bond hydrolyzed by a particular protease. Thus the first amino acid residue on the amino side of the cleaved peptide bond is designated $P_1$ while the first amino acid residue on the carboxyl side of the cleaved peptide bond is designated $P_1'$. The numbering of the residues increases with distance away from the hydrolyzed peptide bond. Thus a four amino acid protease binding region would contain amino acids designated:

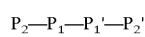

and the protease would cleave the binding region between $P_1$ and $P_1'$.

In a preferred embodiment, the protease binding region of the fluorogenic protease indicators of the present invention is selected to be symmetric about the cleavage site. Thus, for example, where a binding region is Ile-Pro-Met-Ser-Ile (SEQ ID NO:4)

(e.g. α-1 anti-trypsin) and the cleavage occurs between Met and Ser then a four amino acid residue binding region based on this sequence would be:

—P$_2$—P$_1$—P$_1$'—P$_2$'—

Pro-Met-Ser-Ile (SEQ ID NO:5)

Other examples of binding domains selected out of longer sequences are provided in Table 2. The remaining amino or carboxyl residues that are not within the protease binding domain may remain as part of the conformation determining regions subject to certain limitations as will be explained below. Thus, in the instant example, the amino terminal Ile may be incorporated into the C$^1$ conformation determining region.

Various amino acid substitutions may be made to the amino acids comprising the protease binding domain to increase binding specificity, to eliminate reactive side chains, or to reduce the conformational entropy (decrease degrees of freedom) of the molecule. Thus, for example, it is often desirable to substitute methionine (Met) residues, which bear a oxidizable sulfur, with norleucine. Thus, in the example given, a preferred protease binding region will have the sequence:

—P$_2$—P$_1$—P$_1$'—P$_2$'—

Pro-Met-Ser-Ile

Conformation Determining Regions

Conformation determining regions (C$^1$ and C$^2$) are peptide regions on either end of the protease cleavage region that both stiffen and introduce bends into the peptide backbone of the fluorogenic protease indicator molecules S of this invention. The combination of the two conformation determining regions and the relatively straight protease cleavage region produces a roughly U-shaped molecule with the cleavage site at the base (middle) of the "U". The term U-shaped is, of course, approximate, the point being that, as described below, the fluorophores are held relatively rigidly in close juxtaposition (e.g., less than about 100 angstroms).

In one preferred embodiment, amino acids such as proline (Pro) and a-aminoisobutyric acid (Aib) are selected both to introduce bends into the peptide molecule and to increase the rigidity of the peptide backbone. The C$^1$ and C$^2$ domains are selected such that the "arms" of the U are rigid and the attached fluorophores are localized adjacent to each other at a separation of less than about 100 angstroms. In order to maintain the requisite stiffness of the peptide backbone and placement of the fluorophores, the conformation determining regions are preferably 4 amino acids in length or less, or alternatively are greater than about 18 amino acids in length and form a stable alpha helix conformation or a β-pleated sheet.

A) Tetrapeptide binding site compositions.

In a preferred embodiment, the peptide backbone of the fluorogenic protease indicators of the present invention will comprise a tripeptide C$^1$ region, a tetrapeptide P region and a single amino acid or dipeptide C$^2$ region. These compounds may be represented by the formula:

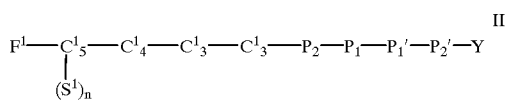

where Y is either

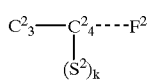

or

In these formulas the peptide binding region is designated —P$_2$—P$_1$—P$_1$'—P$_2$'—, while the amino acid residues of conformation determining regions C$^1$ and C$^2$ are designated —C$^1_5$—C$^1_4$—C$^1_3$— and —C$^2_3$—C$^2_4$— respectively. The C$^2$ region may either be an amino acid or a dipeptide. Whether the C$^2$ region is a dipeptide or an amino acid, the F$^2$ fluorophore and the S$^2$ spacer, when present, are always coupled to the carboxyl terminal residue of C$^2$. When a spacer is present on the C$^2$ region, it is attached the carboxyl terminal residue of C$^2$ by a peptide bond to the α carboxyl group.

As indicated above, the conformation determining regions typically contain amino acid residues such as a proline (Pro) that introduce a bend into the molecule and increase its stiffness. One of skill in the art will appreciate, however that where the terminal residues of the protease binding region (P) are themselves bend-creating residues such as proline, it is not necessary to locate a bend-creating residue at the position closest to P in the C region attached to that terminus. The conformation determining regions are thus designed by first determining the protease binding region, as described above, determining the "left-over" residues that would lie in the conformation determining regions, and if necessary, modifying those residues according to the following guidelines:

1. If the P$_2$' site is not a Pro then C$^2$ is a dipeptide (Formula III) Pro-Cys, Aib-Cys, Pro-Lys, or Aib-Lys, while conversely, if the P$_2$' site is a Pro then C$^2$ is a single amino acid residue (Formula IV) Cys or Lys.
2. If the P$_2$ site is not a Pro then C$^1$ is a tripeptide consisting of Asp-C$^1_4$-Pro, Asp-C$^1_4$-Aib, Asp-Aib-Pro, Asp-Pro-C$^1_3$, Asp-Aib-C$^1_3$, Asp-Pro-Aib, or Asp-Aib-Aib, while if the P$_2$ site is a Pro residue then group C$^1$ is a tripeptide consisting of Asp-C$^1_4$—C$^1_3$ or Asp-C$^1_4$-Aib.
3. If the P$_3$ (C$^1_3$) residue is a Pro then C$^1$ is a tripeptide consisting of Asp-C$^1_4$-Pro or Asp-Aib-Pro.
4. If the P$_4$ (C$^1_4$) residue is a Pro then C$^1$ is a tripeptide consisting of Asp-Pro-C$^1_3$ or Asp-Pro-Aib.
5. If P$_2$ and C$^1_3$ are both not prolines then C$^1$ is a tripeptide consisting of Asp-Pro-C$^1_3$, Asp-Aib-C$^1_3$, Asp-C$^1_4$-Pro, Asp-C$^1_4$-Aib, Asp-Pro-Aib, or Asp-Aib-Pro.

As indicated above, any methionine (Met) may be replaced with a norleucine (Nle). A number of suitable peptide backbones consisting of C$^1$, P and C$^2$ are provided in Table 2.

TABLE 2

Illustration of the design of the conformation determining regions and protease binding site based on known protease substrate and inhibitor sequences. Italics indicate residues that are added to create a bend and to increase rigidity of the conformation determining regions. Normal font indicates residues of the substrate or inhibitor that forms the protease binding site. The thick line indicates the location at which the protease binding site is cleaved.

| Substrate/ Inhibitor | CDR ($C^1$) | | | Protease Binding Site (P) | | | | CDR ($C^2$) | | SEQ ID NO: |
|---|---|---|---|---|---|---|---|---|---|---|
| | $C^1_5$ | $C^1_4$ | $C^1_3$ | $P_2$ | $P_1$ | $P_1'$ | $P_2'$ | $C^2_3$ | $C^2_4$ | |
| α-1 anti-trypsin | Asp | Ala | Ile | Pro | Met Nle | Ser | Ile | Pro Aib | Cys Lys | 7 |
| plasminogen activator inhibitor 2 | Asp | Met Aib Pro | Thr Aib Pro | Gly | Arg | Thr | Gly | Pro Aib | Cys Lys | 8 |
| neutrophil leukocyte elastase inhibitor | Asp | Ala Aib | Thr Aib Pro | Phe | Cys | Met Nle | Leu | Pro Aib | Cys Lys | 9 |
| anti-plasmin inhibitor | Asp | Aib | Ser Aib Pro | Arg | Met Nle | Ser | Leu | Pro Aib | Cys Lys | 10 |
| anti α-1 thrombin | Asp | Ile Aib | Ala Aib Pro | Gly | Arg | Ser | Leu | Pro Aib | Cys Lys | 11 |
| α-1 antichymotrypsin | Asp | Aib | Thr Aib Pro | Leu | Leu | Ser | Leu | Pro Aib | Cys Lys | 12 |
| interstitial type III (human liver) collagen | Asp | Gly Aib | Pro Aib | Leu | Gly | Ile | Ala | Pro Aib | Cys Lys | 13 |
| type I collagen for collagenase Bovine α 1 | Asp | Gly Aib Pro | Pro Aib | Gln | Gly | Ile | Leu | Pro Aib | Cys Lys | 14 |
| type I collagen chick α2 | Asp | Gly Aib Pro | Pro Aib | Gln | Gly | Leu | Leu | Pro Aib | Cys Lys | 15 |
| human α1 type II collagen | Asp | Gly Aib Pro | Pro Aib | Gln | Gly | Ile | Ala | Pro Aib | Cys Lys | 16 |
| type III collagen - AIA | Asp | Gly Aib Pro | Pro Aib | Gln | Ala | Ile | Ala | Pro Aib | Cys Lys | 17 |
| type III collagen (human skin) | Asp | Gly Aib Pro | Pro Aib | Gln | Gly | Ile | Ala | Pro Aib | Cys Lys | 18 |
| human α 2 macroglobulin | Asp | Gly Aib Pro | Pro Aib | Glu | Gly | Leu | Arg | Pro Aib | Cys Lys | 19 |
| stromelysin cleavage sites of stromelysin-1d | Asp | Asp Aib Pro | Val Aib Pro | Gly | His | Phe | Arg | Pro Aib | Cys Lys | 20 |
| stromelysin cleavage sites of stromelysin-1 | Asp | Asp Aib Pro | Thr Aib Pro | Leu | Glu | Val | Met Nle | Pro Aib | Cys Lys | 21 |
| stromelysin cleavage site of proteoglycan link protein | Asp | Arg Aib Pro | Ala Aib Pro | Ile | His | Ile | Gln | Pro Aib | Cys Lys | 22 |
| gelatinase type IV collagenase site of 72 K gelatinases | Asp | Asp Aib Pro | Val Aib Pro | Ala | Asn | Tyr | Asn | Pro Aib | Cys Lys | 23 |
| gelatinase type IV cleavage of gelatin | Asp | Gly Aib Pro | Pro Aib | Ala | Gly | Glu | Arg | Pro Aib | Cys Lys | 24 |
| gelatinase type IV cleavage of gelatin | Asp | Gly Aib Pro | Pro Aib | Ala | Gly | Phe | Ala | Pro Aib | Cys Lys | 25 |
| type III collagen (human skin) | Asp | Gly Aib Pro | Pro Aib | Gln | Gly | Leu | Ala | Pro Aib | Cys Lys | 26 |
| Human FIB-CL propeptide | Asp | Asp Aib Pro | Val Aib Pro | Ala | Gln | Phe | Val | Pro Aib | Cys Lys | 27 |
| Cathepsin D (Thyroglobulin Fragment Tg1) | Asp | Asp Aib Pro | Gly Pro Aib | His | Phe | Leu | Arg | Pro Aib | Cys Lys | 28 |

TABLE 2-continued

Illustration of the design of the conformation determining regions and protease binding site based on known protease substrate and inhibitor sequences. Italics indicate residues that are added to create a bend and to increase rigidity of the conformation determining regions. Normal font indicates residues of the substrate or inhibitor that forms the protease binding site. The thick line indicates the location at which the protease binding site is cleaved.

| Substrate/ Inhibitor | CDR ($C^1$) | | | Protease Binding Site (P) | | | | CDR ($C^2$) | | SEQ ID NO: |
|---|---|---|---|---|---|---|---|---|---|---|
| | $C^1_5$ | $C^1_4$ | $C^1_3$ | $P_2$ | $P_1$ | $P_1'$ | $P_2'$ | $C^2_3$ | $C^2_4$ | |
| Cathepsin D (Thyroglobulin Fragment Tg2) | Asp | Thr Aib Pro | Thr Pro Aib | Glu | Leu | Phe | Ser | Pro Aib | Cys Lys | 29 |
| Cathepsin D (Thyroglobulin Fragment Tg3) | Asp | Lys Aib Pro | Phe Pro Aib | leu | Ala | Phe | Leu | Pro Aib | Cys Lys | 30 |
| Cathepsin D (Thyroglobulin Fragment Tg4) | Asp | Phe Aib Pro | Ser Pro Aib | His | Phe | Val | Arg | Pro Aib | Cys Lys | 31 |
| Prostate Specific Antigen (PSA) (Seminolgelin, Sg) Sg1 | Asp | Gln Aib Pro | Gln Pro Aib | Leu | Leu | His | Asn | Pro Aib | Cys Lys | 32 |
| Prostate Specific Antigen (PSA) (Seminolgelin, Sg) Sg2 | Asp | Ser Aib Pro | Ile Pro Aib | Gln | Tyr | Thr | Tyr | Pro Aib | Cys Lys | 33 |
| Prostate Specific Antigen (PSA) (Seminolgelin, Sg) Sg3 | Asp | Ser Aib Pro | Ser Pro Aib | Gln | Tyr | Ser | Asn | Pro Aib | Cys Lys | 34 |
| Prostate Specific Antigen (PSA) (Seminolgelin, Sg) Sg4 | Asp | Ser Aib Pro | Ser Pro Aib | Ile | Tyr | Ser | Gln | Pro Aib | Cys Lys | 35 |
| Gelatin α1 (type 1) | Asp | Gly Aib Pro | Pro Aib | Ala | Gly | Val | Gln | Pro Aib | Cys Lys | 36 |

[1]In a preferred embodiment, the sequence may be followed by an $S_2$ spacer of Gly-Tyr. Thus, for example, where $C^2_4$ is Lys, $C^2_4$-$S_2$ is Lys-Gly-Tyr.

B) Indicators having other binding sites.

In another preferred embodiment, the binding site (P) ranges from 2 to about 12 amino acids in length. It was a discovery of this invention, that somewhat larger conformation determining regions can sufficiently restrict the degrees of freedom of the indicator molecule, that the fluorophores are suitably quenched regardless of the amino acid sequence of the binding (recognition) domain (P). In one preferred embodiment, these compositions are include the compounds represented by the Formula V:

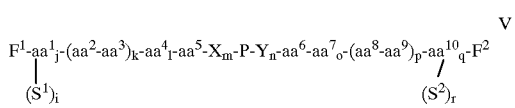

In this formula, P is a peptide comprising a protease binding site and consists of 2 to about 12 amino acids, $F^1$ and $F^2$ are fluorophores where Fl is attached to the amino terminal amino acid and $F^2$ is attached to the carboxyl terminal amino acid of the composition (excluding spacers). $S^1$ and $S^2$, when present, are peptide spacers ranging in length from 1 to about 50 amino acids and $S^1$, when present, is attached to the amino terminal amino acid, while $S^2$, when present, is attached to the carboxyl terminal amino acid. The subscripts i, j, k, I, m, n, o, p, q, and r are independently 0 or 1.

In a particularly preferred embodiment, $aa^1$ and $aa^{10}$ are independently selected from the group consisting of lysine, ornithine and cysteine; $aa^2$, $aa^3$, $aa^8$ and $aa^9$ are independently selected from the group consisting of an amino acid or a dipeptide consisting of Asp, Glu, Lys, Ornithine, Arg, Citulline, homocitrulline, Ser, homoserine, Thr, and Tyr; $aa^5$, $aa^4$, $aa^6$, and $aa^7$ are independently selected from the group consisting of proline, 3,4-dehydroproline, hydroxyproline, alpha aminoisobutyric acid and N-methyl alanine; X is selected from the group consisting of Gly, βAla, γAbu, Gly-Gly, Ahx, βAla-Gly, βAla-βAla, γAbu-Gly, βAla-γAbu, Gly-Gly-Gly, γAbu-γAbu, Ahx-Gly, βAla-Gly-Gly, Ahx-βAla, βAla-βAla-Gly, Gly-Gly-Gly-Gly (SEQ ID NO:37), Ahx-γAbu, βAla-βAla-βAla, γAbu-βAla-Gly, γAbu-γAbu-Gly, Ahx-Ahx, γAbu-γAbu-βAla, and Ahx-Ahx-Gly; Y is selected from the group consisting of Gly, βAla, γAbu, Gly-Gly, Ahx, Gly-βAla, βAla-βAla, Gly-γAbu, γAbu-βAla, Gly-Gly-Gly, γAbu-γAbu, Gly-Ahx, Gly-Gly-βAla,βAla-Ahx, Gly-βAla-βAla, Gly-Gly-Gly-Gly (SEQ ID NO:37), γAbu-Ahx, βAla-βAla-βAla, Gly-βAla-γAbu, Gly-γAbu-γAbu, Ahx-Ahx, βAla-γAbu-γAbu, and Gly-Ahx-Ahx.

When i is 1, $S^1$ is joined to $aa^1$ by a peptide bond through a terminal alpha amino group of $aa^1$; and when r is 1, $S^2$ is joined to $aa^{10}$ by a peptide bond through a terminal alpha carboxyl group of $aa^{10}$. It will be appreciated that amino acids 1–4 or 7–10 may be absent. When one or more of these amino acids are absent, the fluorophores are attached to the remaining terminal amino acids.

The amino acid backbones of such particularly preferred compositions are listed in Tables 3 and 4.

TABLE 3

Illustration of the design of the conformation determining regions and protease binding sites in molecules having P domains lar TABLE 4-continued Illustration of the design of the conformation determining regions and protease binding sites in molecules having P domains larger that 4 amino acids. The PI residue is underlined. Z is benzyloxycarbonyl group, K[TFA] means Lys(N(epsilon)trifluoroacetyl), Fm is Fmoc (preferably attached to the alpha amino group of the amino terminal residue e.g., Lysine (K). O indicates tetrahydroisoquinoline-3-carboxylic acid. Aib, designated as B, can be replaced by Pro. J is a C

| Substrate class | aa$^1$ | aa$^2$–aa$^3$ | aa$^4$ | aa$^5$ | X | P | Y | aa$^6$ | aa$^7$ | aa$^8$–aa$^9$ | aa$^{10}$ | S$^2$ | SEQ ID NO: |
|---|---|---|---|---|---|---|---|---|---|---|---|---|---|
| | K | D | | B | JG | DVVCDSdMS | GJ | P | | | K | GY | — |
| | K | D | | B | JG | DVVCCPdMS | GJ | P | | | K | GY | — |
| | K | D | | B | JG | EDVVCCS | GJ | P | | | K | GY | 87 |
| | K | D | | B | JG | EDVVCDS | GJ | P | | | K | GY | 88 |
| | K | D | | B | JG | EDdVVCCP | GJ | P | | | K | GY | — |
| | K | D | | B | JG | EDdVVCDP | GJ | P | | | K | GY | — |
| | K | D | | B | JG | DdVVCCSdMS | GJ | P | | | K | GY | — |
| | K | D | | B | JG | DVdVCDSdMS | GJ | P | | | K | GY | — |
| | K | D | | B | JG | DdVVCCPdMS | GJ | P | | | K | GY | — |
| | K | D | | B | JG | DVVCCSM | GJ | P | | | K | GY | 89 |
| | K | D | | B | JG | DWCDSM | GJ | P | | | K | GY | 90 |
| | K | D | | B | JG | VCCSM | GJ | P | | | K | GY | 91 |
| | K | D | | B | JG | VCDSM | GJ | P | | | K | GY | 92 |
| NS3 NS4A/4B | K | D | | B | JG | DEMEECSQHL | | P | | | K | GY | 93 |
| | K | D | | B | JG | DEMEECPQHL | | P | | | K | GY | 94 |
| | K | D | | B | JG | DEMEEDSQHL | | P | | | K | GY | 95 |
| | K | D | | B | JG | EMEECSQHL | | P | | | K | GY | 96 |
| | K | D | | B | JG | EMEECPQHL | | P | | | K | GY | 97 |
| | K | D | | B | JG | EMEEDSQHL | | P | | | K | GY | 98 |
| | K | D | | B | JG | EMEECSQHL | G | P | | | K | GY | 99 |
| | K | D | | B | JG | EMEECPQHL | G | P | | | K | GY | 100 |
| | K | D | | B | JG | EMEEDSQHL | G | P | | | K | GY | 101 |
| | K | D | | B | JG | EMEECSQHL | GJ | P | | | K | GY | 102 |
| | K | D | | B | JG | EMEEDSQHL | GJ | P | | | K | GY | 103 |
| | K | D | | B | JG | EMEEDSQHL | GJ | P | | | K | GY | 104 |
| Ext. PAI-2 | K | D | | B | JG | VMTGRTG | J | P | | | K | GY | 105 |
| | K | D | | B | JG | VdMTGRTG | J | P | | | K | GY | — |
| | K | D | | B | JG | VMTGRTG | J | P | | | K | GY | 106 |
| | K | D | | B | JG | VMTGRTG | J | P | | | K | GY | 106 |
| THROMB | K | D | | B | JG | VMTGRG | J | P | | | K | GY | 107 |
| | K | D | | B | JG | VMTGRG | GJ | P | | | K | GY | 108 |
| | K | D | | B | JG | VdmTGRG | GJ | P | | | K | GY | 109 |
| UROK | K | D | | B | JG | VMTGRVG | J | P | | | K | GY | 110 |
| | K | D | | B | JG | VdMTGRVG | J | P | | | K | GY | — |
| F12A | K | D | | B | JG | VMTGRAG | J | P | | | K | GY | 111 |
| | K | D | | B | JG | VdMTGRAG | J | P | | | K | GY | — |
| Swedish KM/NL | K | D | | B | JG | SEVNLDAEF | GJ | P | | | K | DDY | 112 |
| AMLOID | K | D | | B | JG | SEVKLDAEF | GJ | P | | | K | DDY | 113 |
| NATIVE AMYLOID | K | D | | B | JG | SEVKMDAEF | GJ | P | | | K | DDY | 114 |
| CATHESPSIN G | K | D | | B | JG | SEVKMDDEF | GJ | P | | | K | DDY | 115 |
| | K | D | | B | JG | SEVNLDDEF | GJ | P | | | K | DDY | 116 |
| APP[709–710] | K | D | | B | JG | GVVIATVIVIT | GJ | P | | | K | DDY | 117 |
| APP[708–719] | K | D | | B | JG | YGVVIATVIVIT | GJ | P | | | K | DDY | 118 |
| APP[711–716] | K | D | | B | JG | VIATVI | GJ | P | | | K | DDY | 119 |
| APP[708–713] | K | D | | B | JB | YGVVIA | GJ | P | | | K | DDY | 120 |
| PSA Sg1 | K | D | | B | JJ | QQLLHN | JJ | P | | | K | | 121 |
| | K | D | | B | JG | QQLLHN | GJ | P | | | K | | 122 |
| | K | D | | B | G | QQLLHN | G | P | | | K | | 123 |
| | K | D | | B | | QQLLHN | | P | | | K | | 124 |
| PSA Sg2 | K | D | | B | JJ | SIQYTY | JJ | P | | | K | | 125 |
| | K | D | | B | JG | SIQYTY | GJ | P | | | K | | 126 |
| | K | D | | B | G | SIQYTY | G | P | | | K | | 127 |
| | K | D | | B | | SIQYTY | | P | | | K | | 128 |
| PSASg3 | K | D | | B | JJ | SSQYSN | JJ | P | | | K | | 129 |
| | K | D | | B | JG | SSQYSN | GJ | P | | | K | | 130 |
| | K | D | | B | G | SSQYSN | G | P | | | K | | 131 |
| | K | D | | B | | SSQYSN | G | P | | | K | | 132 |
| PSA Sg4 | K | D | | B | JJ | SSIYSQ | JJ | P | | | K | | 133 |
| | K | D | | B | JG | SSIYSQ | GJ | P | | | K | | 134 |
| | K | D | | B | G | SSIYSQ | G | P | | | K | | 135 |
| | K | D | | B | | SSIYSQ | | P | | | K | | 136 |

"Donor" and "Acceptor" Fluorophores

A fluorophore excited by incident radiation absorbs light and then subsequently re-emits that light at a different (longer) wavelength. However, in the presence of a second class of molecules, known as "acceptors" the light emitted by a so-called donor fluorophore is absorbed by the acceptor thereby quenching the fluorescence signal of the donor. Thus, use of two fluorophores, as opposed to a fluorophore/chomophore pair, allows a clearer assessment of the overlap between the emission spectrum of the donor and the excitation spectrum of the acceptor. This facilitates the design of a peptide backbone that allows allowing optimization of the quenching. This results in a high efficiency donor/acceptor pair facilitating the detection of low concentrations of protease activity. Thus, although a fluorophorelchromophore combination may be suitable, in a preferred embodiment, the fluorogenic protease inhibitors of this invention will comprise two fluorophores.

The "donor" and "acceptor" molecules are typically selected as a matched pair such that the absorption spectra of the acceptor molecule overlaps the emission spectrum of the donor molecule as much as possible. In addition, the donor and acceptor fluorophores are preferably selected such that both the absorption and the emission spectrum of the donor molecule is in the visible range (400 nm to about 700 nm). The fluorophores thereby provide a signal that is detectable in a biological sample thus facilitating the detection of protease activity in biological fluids, tissue homogenates, in situ in tissue sections, and the like. The emission spectra, absorption spectra and chemical composition of many fluorophores are well known to those of skill in the art (see, for example, *Handbook of Fluorescent Probes and Research Chemicals*, R. P. Haugland, ed. which is incorporated herein by reference).

Preferred fluorophore pairs include the rhodamine derivatives. Thus, for example 5-carboxytetramethylrhodamine or the succinimidyl ester of 5- and/or 6-carboxytetramethylrhodamine (C2211 and C1171, respectively, available from Molecular Probes, Eugene, Oreg., USA) (Formula VI) is a particularly preferred donor molecule

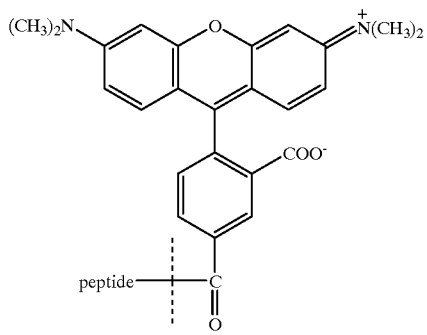

and rhodamine X acetamide (R 492 from Molecular Probes) (Formula VII)

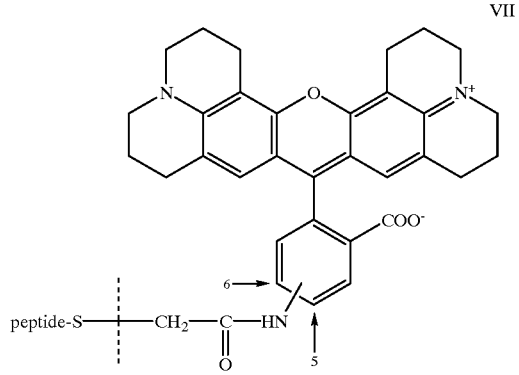

or the succinimidyl ester of 5- and/or 6-carboxy-X-rhodamine (C1309 from Molecular Probes) is a particularly preferred receptor molecule. These fluorophores are particularly preferred since the excitation and emission of both members of this donor/acceptor pair are in the visible wavelengths, the molecules have high extinction coefficients and the molecules have high fluorescence yields in solution. The extinction coefficient is a measure of the light absorbance at a particular wavelength by the chromophore and is therefore related to its ability to quench a signal, while the fluorescence yield is the ratio of light absorbed to light re-emitted and is a measure of the efficiency of the fluorophore and thus effects the sensitivity of the protease indicator.

Of course, while not most preferred, fluorophores that absorb and emit in the ultraviolet may also be used in the protease indicators of the present invention. One particularly preferred ultraviolet absorbing pair of fluorophores is 7-hydroxy-4-methylcoumarin-3-acetic acid as the donor molecule (Formula VII)

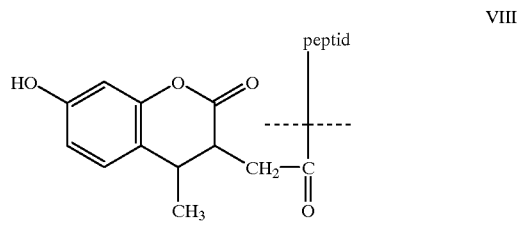

and 7-diethylamino-3-((4'-iodoacetyl)amino)phenyl )-4-methylcoumarin (Formula IX) as the acceptor molecule.

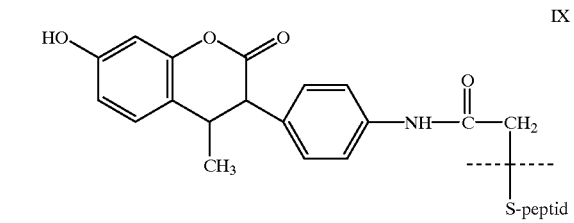

These and other fluorophores are commercially available from a large number of manufacturers such as Molecular Probes (Eugene, Oreg., USA).

It was a surprising discovery that fluorophores having matched absorption and emission spectra are not required in the practice of the present invention. In fact, a single species of fluorophore, when joined to the polypeptide backbones of this invention in the positions occupied by $F^1$ and $F^2$, is capable of quenching itself. Moreover, this quenching is fully released when the peptide backbone is cleaved.

Without being bound to a particular theory, it is believed that quenching is accomplished by the formation of ground state dimers wherein the electron orbitals of the two fluorophores interact resulting in reciprocal quenching. It is the limited conformational entropy of the peptide backbones of this invention that forces fluorophores into close enough proximity to effectively form a ground state dimer.

Particularly preferred molecules form H-type dimers. The formation of H-type dimers by fluorescent molecules is described by Packard et a. (1996) *Proc. Natl. Acad. Sci. USA*, 93: 11640–11645. The H-type dimer is characterized by exciton bands in the absorption spectra and fluorescence quenching (see, e.g., Valdes-Aguilera et al. (1989) *Acc. Chem. Res.*, 22: 171–177 and Packard et al. (1996) *Proc. Natl. Acad. Sci. USA*, 93: 11640–11645).

Thus, in a preferred embodiment, the protease indicators of this invention include only a single species of fluorophore, more preferably a fluorophore capable of forming H-type dimers. Particuarly preferred fluorophores include carboxytetramethylrhodamine, carboxyrhodamine-X, diethylaminocoumarin, and carbocyanine dyes. In this embodiment, there is no need to match emission or absorption spectra since only a single fluorophore is used. Thus a wide variety of fluorophores can be used effectively. In addition, the use of a single fluorophore greatly simplifies synthesis chemistry.

The use of homo-doubly labeled indicators (indicators labeled with a single species of fluorophore) of this invention also permits detection of enzymatic activity by absorbance measurements in addition to fluorescence measurements. Since blue-shifted exciton bands (or blue-shifted absorption maxima) in absorption spectra denote H-dimer formation and fluorescence quenching is concomitant with the latter, measurement of absorption spectra may be sufficient as a diagnostic tool in the proper setting. When a doubly labeled protease indicator is cleaved by a specific protease, the H-type dimer is disrupted. The blue shifted absorption maximum associated with the H-type dimer is then lost. Hence, if one measures the intensity of absorption at this blue shifted exciton band then as the H-type dimer is disrupted the absorption intensity is expected to decreased whereas the absorption intensity at the monomer maximum peak wavelength is expected to increase.

Preparation of Fluorogenic Protease Indicators

The fluorogenic protease indicators of the present invention are preferably prepared by first synthesizing the peptide backbone, ie. the protease cleavage site (P), the two conformation determining regions ($C^1$ and $C^2$), and the spacers ($S^1$ and $S^2$) if present. The fluorophores are then chemically conjugated to the peptide. The fluorophores are preferably conjugated directly to the peptide however, they may also be coupled to the peptide through a linker. Finally, where the fluorogenic protease indicator is to be bound to a solid support, it is then chemically conjugated to the solid support via the spacer ($S^1$ or $S^2$) either directly or through a linker.

Preparation of the peptide backbone

Solid phase peptide synthesis in which the C-erminal amino acid of the sequence is attached to an insoluble support followed by sequential addition of the remaining amino acids in the sequence is the preferred method for preparing the peptide backbone of the compounds of the present invention. Techniques for solid phase synthesis are described by Barany and Merrifield, *Solid-Phase Peptide Synthesis*; pp. 3–284 in *The Peptides: Analysis, Synthesis, Biology*. Vol. 2: *Special Methods in Peptide Synthesis*, Part A., Merrifield, et al. *J. Am. Chem. Soc.* 85, 2149–2156 (1963), and Gross and Meienhofer, eds. Academic press, N.Y., 1980 and Stewart et al., *Solid Phase Peptide Synthesis,* 2nd ed. Pierce Chem. Co., Rockford, Ill. (1984) which are incorporated herein by reference. Solid phase synthesis is most easily accomplished with commercially available peptide synthesizers utilizing FMOC or TBOC chemistry. The chemical synthesis of the peptide component of a fluorogenic protease indicator is described in detail in Examples 1 and 2.

In a particularly prefered embodiment, peptide synthesis is performed using Fmoc synthesis chemistry. The side chains of Asp, Ser, Thr and Tyr are preferably protected using t-Butyl and the side chain of Cys residue using S-trityl and S-t-butylthio, and Lys residues are preferably protected using t-Boc, Fmoc and 4-methyltrityl for lysine residues. Appropriately protected amino acid reagents are commercially available. The use of multiple protecting groups allows selective deblocking and coupling of a fluorophore to any particular desired side chain. Thus, for example, t-Boc deprotection is accomplished using TFA in dichloromethane, Fmoc deprotection is accomplished using 20% (v/v) piperidine in DMF or N-methylpyrolidone, and 4-methyltrityl deprotection is accomplished using 1 to 5% (v/v) TFA in water or 1% TFA and 5% truisopropylsilane in DCM, S-t-butylthio deprotection is accomplished in aqueous mercaptoethanol (10%), t-butyl and t-boc and S-trityl deprotection is accomplished using TFA:phenol:water:thioanisol:ethanedithiol (85:5:5:2.5:2.5), and t-butyl and t-Boc deprotection is accomplished using TFA:phenol:water (95:5:5). Detailed synthesis, deprotection and fluorophore coupling protocols are provided in Examples 1 and 2.

Alternatively, the peptide components of the fluorogenic protease indicators of the present invention may be synthesized utilizing recombinant DNA technology. Briefly, a DNA molecule encoding the desired amino acid sequence is synthesized chemically by a variety of methods known to those of skill in the art including the solid phase phosphoramidite method described by Beaucage and Carruthers, *Tetra. Letts.* 22: 1859–1862 (1981), the triester method according to Matteucci, et al., *J. Am. Chem. Soc.,* 103:3185 (1981), both incorporated herein by reference, or by other methods known to those of skill in the art. It is preferred that the DNA be synthesized using standard β-cyanoethyl phosphoramidites on a commercially available DNA synthesizer using standard protocols.

The oligonucleotides may be purified, if necessary, by techniques well known to those of skill in the art. Typical purification methods include, but are not limited to gel electrophoresis, anion exchange chromatography (e.g. Mono-Q column, Pharmacia-LKB, Piscataway, N.J., USA), or reverse phase high performance liquid chromatography (HPLC). Method of protein and peptide purification are well known to those of skill in the art. For a review of standard techniques see, *Methods in Enzymology* Volume 182: *Guide to Protein Purification*, M. Deutscher, ed. (1990), pages 619–626, which are incorporated herein by reference.

The oligonucleotides may be converted into double stranded DNA either by annealing with a complementary oligonucleotide or by polymerization with a DNA polymerase. The DNA may then be inserted into a vector under the control of a promoter and used to transform a host cell so that the cell expresses the encoded peptide sequence. Methods of cloning and expression of peptides are well known to those of skill in the art. See, for example, Sambrook, et al., *Molecular Cloning: A Laboratory Manual* (2nd Ed., Vols. 1–3, Cold Spring Harbor Laboratory (1989)), *Methods in Enzymology*, Vol. 152: *Guide to Molecular Cloning Techniques* (Berger and Kimmel (eds.), San Diego: Academic Press, Inc. (1987)), or *Current Protocols in Molecular Biology*, (Ausubel, et al. (eds.), Greene Publishing and Wiley-lnterscience, New York (1987), which are incorporated herein by reference.

Linkage of the fluorophores to the peptide backbone

The fluorophores are linked to the peptide backbone by any of a number of means well known to those of skill in the art. In a preferred embodiment, the fluorophore is linked directly from a reactive site on the fluorophore to a reactive group on the peptide such as a terminal amino or carboxyl group, or to a reactive group on an amino acid side chain such as a sulfur, an amino, a hydroxyl, or a carboxyl moiety. Many fluorophores normally contain suitable reactive sites. Alternatively, the fluorophores may be derivatized to provide reactive sites for linkage to another molecule. Fluorophores derivatized with functional groups for coupling to a second molecule are commercially available from a variety of manufacturers. The derivatization may be by a simple substitution of a group on the fluorophore itself, or may be by conjugation to a linker. Various linkers are well known to those of skill in the art and are discussed below.

As indicated above, in a preferred embodiment, the fluorophores are directly linked to the peptide backbone of the protease indicator. Thus, for example, the 5'-carboxytetramethylrhodamine (C2211) fluorophore may be linked to aspartic acid via the alpha amino group of the amino acid as shown in Formula V. The iodoacetamide group of rhodamine X acetamide (R492)) may be linked by reaction with the sulfhydryl group of a cysteine as indicated in formula VI. Means of performing such couplings are well known to those of skill in the art, and the details of one such coupling are provided in Example 1.

One of skill in the art will appreciate that when the peptide spacers ($S^1$ or $S^2$) are present (as is discussed below), the fluorophores are preferably linked to the conformation determining regions through a reactive group on the side chain of the terminal amino acid of $C^1$ or $C^2$ as the spacers themselves form a peptide linkage with the terminal amino and carboxyl groups of $C^1$ or $C^2$ respectively.

Selection of spacer peptides and linkage to a solid support

The fluorogenic protease indicators of the present invention may be obtained in solution or linked to a solid support. A "solid support" refers to any solid material that does not dissolve in or react with any of the components present in the solutions utilized for assaying for protease activity using the fluorogenic protease indicator molecules of the present invention and that provides a functional group for attachment of the fluorogenic molecule. Solid support materials are well known to those of skill in the art and include, but are not limited to silica, controlled pore glass (CPG), polystyrene, polystyrene/latex, carboxyl modified teflon, dextran, derivatized polysaccharaides such as agar bearing amino, carboxyl or sulfhydryl groups, various plastics such as polyethylene, acrylic, and the like. Also of use are "semi-solid" supports such as lipid membranes as found in cells and in liposomes. One of skill will appreciate that the solid supports may be derivatized with functional groups (e.g. hydroxyls, amines, carboxyls, esters, and sulfhydryls) to provide reactive sites for the attachment of linkers or the direct attachment of the peptide.

The fluorogenic protease indicators may be linked to a solid support directly through the fluorophores or through the peptide backbone comprising the indicator. Linkage through the peptide backbone is most preferred.

When it is desired to link the indicator to a solid support through the peptide backbone, the peptide backbone may comprise an additional peptide spacer (designated $S^1$ or $S^2$ in Formula I). The spacer may be present at either the amino or carboxyl terminus of the peptide backbone and may vary from about 1 to about 50 amino acids, more preferably from 1 to about 20 and most preferably from 1 to about 10 amino acids in length. Particularly preferred spacers include Asp-Gly-Ser-Gly-Gly-Gly-Glu-Asp-Glu-Lys (SEQ ID NO:137), Lys-Glu-Asp-Gly-Gly-Asp-Lys (SEQ ID NO:138), Asp-Gly-Ser-Gly-Glu-Asp-Glu-Lys (SEQ ID NO:139), and Lys-Glu-Asp-Glu-Gly-Ser-Gly-Asp-Lys (SEQ ID NO:140).

The amino acid composition of the peptide spacer is not critical as the spacer just serves to separate the active components of the molecule from the substrate thereby preventing undesired interactions. However, the amino acid composition of the spacer may be selected to provide amino acids (e.g. a cysteine or a lysine) having side chains to which a linker or the solid support itself, is easily coupled. Alternatively the linker or the solid support itself may be attached to the amino terminus of $S^1$ or the carboxyl terminus of $S^2$.

In a preferred embodiment, the peptide spacer is actually joined to the solid support by a linker. The term "linker", as used herein, refers to a molecule that may be used to link a peptide to another molecule, (e.g. a solid support, fluorophore, etc.). A linker is a hetero or homobifunctional molecule that provides a first reactive site capable of forming a covalent linkage with the peptide and a second reactive site capable of forming a covalent linkage with a reactive group on the solid support. The covalent linkage with the peptide (spacer) may be via either the terminal carboxyl or amino groups or with reactive groups on the amino acid side-chain (e.g. through a disulfide linkage to a cysteine).

Suitable linkers are well known to those of skill in the art and include, but are not limited to, straight or branched-chain carbon linkers, heterocyclic carbon linkers, or peptide linkers. As indicated above, the linkers may be joined to the carboxyl and amino terminal amino acids through their terminal carboxyl or amino groups or through their reactive side-chain groups.

Particularly preferred linkers are capable of forming covalent bonds to amino groups, carboxyl groups, or sulfhydryl. Amino-binding linkers include reactive groups such as carboxyl groups, isocyanates, isothiocyanates, esters, haloalkyls, and the like. Carboxyl-binding linkers are capable of forming include reactive groups such as various amines, hydroxyls and the like. Finally, sulfhydryl-binding linkers include reactive groups such as sulfhydryl groups, acrylates, isothiocyanates, isocyanates and the like. Particularly preferred linkers include sulfoMBS (m-maleimidobenzoyl-N-hydroxysulfosuccinimide ester) for linking amino groups (e.g. an amino group found on a lysine residue in the peptide) with sulfhydryl groups found on the solid support, or vice versa, for linking sulfhydryl groups (e.g. found on a cysteine residue of the peptide) with amino groups found on the solid support. Other particularly preferred linkers include EDC (1-ethyl-3-(3-dimethylaminopropryl)-carbodiimide) and bis-(sulfosuccinimidyl suberate). Other suitable linkers are well known to those of skill in the art.

The fluorogenic compounds of the present invention may be linked to the solid support through either the $S^1$ or the $S^2$ spacer such that the donor fluorophore is either retained on the solid support after cleavage of the molecule by a protease or such that the donor fluorophore goes into solution after cleavage. In the former case, the substrate is then assayed for fluorescence to detect protease activity, while in the later case the solution is assayed for fluorescence to detect protease activity.

Detection of Protease Activity

The present invention also provides methods for utilizing the fluorogenic protease indicators to detect protease activity in a variety of contexts. Thus, in one embodiment, the present invention provides for a method of using the fluorogenic indicators to verify or quantify the protease activity of a stock solution of a protease used for experimental or industrial purposes. Verification of protease activity of stock protease solutions before use is generally recommended as proteases often to loose activity over time (e.g. through self-hydrolysis) or to show varying degrees of activation when activated from zymogen precursors.

Assaying for protease activity of a stock solution simply requires adding a quantity of the stock solution to a fluorogenic protease indicator of the present invention and measuring the subsequent increase in fluorescence or decrease in exciton band in the absorption spectrum. The stock solution and the fluorogenic indicator may also be combined and assayed in a "digestion buffer" that optimizes activity of the protease. Buffers suitable for assaying protease activity are well known to those of skill in the art. In general, a buffer will be selected whose pH corresponds to the pH optimum of the particular protease. For example, a buffer particularly suitable for assaying elastase activity consists of 50 mM sodium phosphate, 1 mM EDTA at pH 8.9. The measurement is most easily made in a fluorometer, and instrument that provides an "excitation" light source for the fluorophore and then measures the light subsequently emitted at a particular wavelength. Comparison with a control indicator solution lacking the protease provides a measure of the protease activity. The activity level may be precisely quantified by generating a standard curve for the protease/indicator combination in which the rate of change in fluorescence produced by protease solutions of known activity is determined.

While detection of the fluorogenic compounds is preferably accomplished using a fluorometer, detection may by a variety of other methods well known to those of skill in the art. Thus for example, since the fluorophores of the present invention emit in the visible wavelengths, detection may be simply by visual inspection of fluorescence in response to excitation by a light source. Detection may also be by means of an image analysis system utilizing a video camera interfaced to an digitizer or other image acquisition system. Detection may also be by visualization through a filter as under a fluorescence microscope. The microscope may just provide a signal that is visualized by the operator. However the signal may be recorded on photographic film or using a video analysis system. The signal may also simply be quantified in realtime using either an image analysis system or simply a photometer.

Thus, for example, a basic assay for protease activity of a sample will involve suspending or dissolving the sample in a buffer (at the pH optima of the particular protease being assayed), adding to the buffer one of the fluorogenic protease indicators of the present invention, and monitoring the resulting change in fluorescence using a spectrofluorometer. The spectrofluorometer will be set to excite the donor fluorophore at the excitation wavelength of the donor fluorophore and to detect the resulting fluorescence at the emission wavelength of the donor fluorophore.

In another embodiment, the protease activity indicators of the present invention may be utilized for detection of protease activity in biological samples. Thus, in a preferred embodiment, this invention provides for methods of detecting protease activity in isolated biological samples such as sputum, blood, blood cells, tumor biopsies, and the like, or in situ, in cells or tissues in culture, or in section where the section is unimbedded and unfixed. The signal may be quantified using a fluorescence microscope, a fluorescence microplate reader, a fluorometer, or a flow cytometer.

Ex vivo assays of isolated biological samples

In one embodiment, the present invention provides for methods of detecting protease activity in an isolated biological sample. This may be determined by simply contacting the sample with a fluorogenic protease indicator of the present invention and monitoring the change in fluorescence of the indicator over time. The sample may be suspended in a "digestion buffer" as described above. The sample may also be cleared of cellular debris, e.g. by centrifugation before analysis.

Where the fluorogenic protease indicator is bound to a solid support the assay may involve contacting the solid support bearing the indicator to the sample solution. Where the indicator is joined to the solid support by the side of the molecule bearing the donor fluorophore, the fluorescence of the support resulting from digestion of the indicator will then be monitored over time by any of the means described above. Conversely, where the acceptor molecule fluorophore is bound to a solid support, the test solution may be passed over the solid support and then the resulting luminescence of the test solution (due to the cleaved fluorophore) is measured. This latter approach may be particularly suitable for high throughput automated assays.

In situ assays of histological sections.

In another embodiment, this invention provides for a method of detecting in situ protease activity in histological sections. This method of detecting protease activity in tissues offers significant advantages over prior art methods (e.g. specific stains, antibody labels, etc.) because, unlike simple labeling approaches, in situ assays using the protease indicators indicate actual activity rather than simple presence or absence of the protease. Proteases are often present in tissues in their inactive precursor (zymogen) forms which are capable of binding protease labels. Thus traditional labeling approaches provide no information regarding the physiological state, vis a vis protease activity, of the tissue.

The in situ assay method generally comprises providing a tissue section (preferably a frozen section), contacting the section with one of the fluorogenic protease indicators of the present invention, and visualizing the resulting fluorescence. Visualization is preferably accomplished utilizing a fluorescence microscope. The fluorescence microscope provides an "excitation" light source to induce fluorescence of the "donor" fluorophore. The microscope is typically equipped with filters to optimize detection of the resulting fluorescence. Thus, for example, for the fluorogenic protease indicators described in Example 1, a typical filter cube for a Nikon microscope would contain an excitation filter ($\lambda=550\pm12$ nm), a dichroic mirror ($\lambda=580$ nm) and an interference-emission filter ($\lambda=580\pm10$ nm). As indicated above, the microscope may be equipped with a camera, photometer, or image acquisition system.

The sections are preferably cut as frozen sections as fixation or embedding will destroy protease activity in the sample.

The fluorogenic indicator may be introduced to the sections in a number of ways. For example, the fluorogenic protease indicator may be provided in a buffer solution, as described above, which is applied to the tissue section. Alternatively, the fluorogenic protease indicator may be provided as a semi-solid medium such as a gel or agar which is spread over the tissue sample. The gel helps to hold moisture in the sample while providing a signal in response to protease activity. The fluorogenic protease indicator may also be provided conjugated to a polymer such as a plastic film which may be used in procedures similar to the development of Western Blots. The plastic film is placed over the tissue sample on the slide and the fluorescence resulting from cleaved indicator molecules is viewed in the sample tissue under a microscope.

Typically the tissue sample must be incubated for a period of time to allow the endogenous proteases to cleave the fluorogenic protease indicators. Incubation times will range from about 10 to 60 minutes at temperatures up to and including 37° C.

In situ Assays of cells in culture and Cell Suspensions Derived from Tissues and Biopsy Samples.

In yet another embodiment, this invention provides for a method of detecting in situ protease activity of cells in culture or cell suspensions derived from tissues, biopsy samples, or biological fluids (e.g., saliva, blood, urine, lymph, plasma, etc.). The cultured cells are grown either on chamber slides or in suspension and then transferred to histology slides by cytocentrifugation. Similarly, the cell suspensions are prepared according to standard methods and transferred to histology slides. The slide is washed with phosphate buffered saline and coated with a semi-solid polymer or a solution containing the fluorogenic protease indicator. The slide is incubated at 37° C. for the time necessary for the endogenous proteases to cleave the protease indicator. The slide is then examined under a fluorescence microscope equipped with the appropriate filters as described above.

Alternatively, the cells are incubated with the protease indications at 37° C., then washed with buffer and transferred to a glass capillary tube and examined under a fluorescence microscope. When a flow cytometer is used to quatitate the intracellular enzyme activity, the cells with the fluorogenic indicator is simply diluted with buffer after 37° C. incubation and analyzed.

Other Indicator Compositions.

As explained above, it was a discovery of this invention that fluorescent molecules covalently attached on opposite sides of a backbone (e.g., peptide cleavage site) can quench by self-interaction (e.g., through the formation of dimers). Thus, in one embodiment, indicator molecules can be made using a single fluorophore rather than a matched donor-acceptor pair. Also, as explained above, particularly preferred fluorophores are those that form H-type dimers (e.g., carboxytetramethylrhodamine, carboxyrhodamine-X, diethylaminocoumarin and carbocyanine dyes).

The use of single species labeled indicators, however, is not restricted to peptide-based compositions. To the contrary, "homo-double labeled" indicator molecules can utilize a variety of backbones including, but not limited to nucleic acid backbones, oligosaccharide backbones, lipid backbones, and the like. Methods of coupling fluorophores to such backbones are well known to those of skill in the art. For example, conjugation methods for atttaching fluorophores to amino acids, peptides, proteins, nucleic acids, oligonucleotides, sugars, polysaccharides, proteoglycans, lipids, glycolipids and lipopolysaccharides, are described by Hermanson, (1995) *Bioconjugate Techniques*, Academic Press New York, N.Y., Kay M. et al., (1995) *Biochemistry*, 34: 293–300, and by Stubbs, et al. (1996) *Biochemistry* 35: 937–947.

Nucleic acid indicators

Homo-doubly labeled nucleic acid backbones provide effective indicators for nucleic acid hybridizations and/or endonuclease activity. In this embodiment, a nucleic acid backbone is labeled with a self-quenching (e.g., H-type dimer-forming) fluorophore at the 3' and 5' end (either through a direct attachment or indirectly through (e.g., a peptide) linker). The nucleic acid backbone is selected to include self-complementary regions and thererby form a hairpin or other self-hybridized conformation that brings the fluorophores into proximity so that self-quenching occurs. When the indicator (probe) thus formed is hybridized to a complementary target nucleic acid, the self-hybridization is eliminated, the fluorophores are separated and the fluorescence signal produced by the molecule increases. Alternatively, the fluorescently labeled nucleic acid backbone can be used to assay for nuclease activity (e.g., restriction endonuclease or ribozyme activity). When the nucleic acid backbone is cleaved by a nuclease (e.g., by restriction endonuclease recognition of a target site in the backbone) the fluorophores are separated again increasing the fluorescence signal. Methods of selecting appropriate nucleic acid backbones are described by Tyagi and Kramer et al. (1996) *Nature Biotechnology*, 14: 303–308.

The homo-doubely labeled fluorescently DNA probes can be used for detection, localization, or quantification of target DNA sequences in a variety of contexts. Thus, for example, the nucleic acid indicators of this invention can be used for rapid detection of amplification products in nucleic acid amplification (e.g., PCR) reactions. Here the indicator is selected with a backbone complementary to a region of the amplification product. As amplification product is produced the indicator hybridizes to the product and the fluorescence signal activity of the PCR solution increases. The nucleic acid indicators can be used as hybridization or nuclease activity indicators in a variety of other contexts. For example, in in situ hybridization (e.g., FISH) mapping of genomic DNA sequences can be accomplished using fluorescent probes to target particular regions within chromosomes (see, e.g., Meyne(1 993) *Chromosome mapping by fluorescent in situ hybridization*, pp 263–268 In: *Methods in Nonradioactive Detection* G. C. Howard, ed., Appleton & Lange, Norwalk, Conn.; Morrison (1992) *Detection of energy transfer and fluorescence quenching*, pp. 311–352 In: *Nonisotopic DNA Probes Techniques* L. J. Kricka, ed. Academic Press, New York; and Varani (1995) *Annu. Rev. Biophys. Biomol. Struct.* 24: 379–404).

In another embodiment, the self-quenching fluorophores can be used to assay two molecule interactions (e.g., protein-protein, protein-nucleic acid, ligand-receptor, etc.). In this embodiment, one fluorophore is attached to one molecule (e.g., a protein) while the second fluorophore is attached to a second molecule (e.g., a second nucleic acid or a nucleic acid binding protein). When the two molecules bind, the flurophores are juxtaposed and quench each other (e.g., through the formation of H-type dimers). The use of donor-acceptor resonance energy transfer systems to measure two molecule interactions is described by Bannwarth et al., *Helvetica Chimica Acta*. (1991) 74: 1991–1999, Bannwarth et al. (1991), *Helvetica Chimica Acta*. 74: 2000–2007, and Bannwarth et al., European Patent Application No. 0439036A2.

Oligosaccharide Indicators

Homo-doubly labeled oligosaccharide backbone indicators permit the detection of glycosidase activity and lecithin binding protein identification. The fluorophores can be conjugated directly to an oligosaccharide or glycopeptide backbone or attached indirectly through (e.g., peptide) linkers. The oligosaccharides and/or glycopeptides can be chemically synthesized, recombinantly expressed, or isolated from natural sources such as fetuin and other glycoproteins by proteolytic fragmentation of the parent glycoproteins.

As in the case for oligonucleotides, an oligosaccharide specific structure may be selected for detection of a specific glycosidase, an enzyme that hydrolyzes bonds between two sugar molecules.

When a specific oligosaccharide or lecithin is selected to look for its lecithin binding protein, then the increased fluorescence indicates the complexation events that disrupt the H-type dimer, either by separating two dyes or distorting the relative orientation of two dyes. These effects result in increased fluorescence from the homo-double labeled probe.

Lipid Indicators

When a lipid, glycolipid or lipopolysaccharide are labeled with a self-quenching (e.g., H-type dimer forming) fluorophore and added to liposomes or other lipid (e.g., biological) membranes, a decrease in fluorescence will indicate H-type dimer formation and the degree of such fluorescence intensity will be an indication of the amount of H-type dimer formation. Because of the relative fluidity of a lipid membrane, the self-quenching flurophores are able to interact (e.g. approach to a spacing of about 6 to about 10 Å) a stable H-type dimer results. When a membrane active agent, for example, an agent that affects either membrane fluid dynamics or permeabilization to a test compound, is added, then the observed fluorescence intensity changes indicate the test compound's ability to modify membrane fluidity or permeabilization. Hence, such labeled lipids are useful in drug screening and in development of lipid-drug delivery vehicles.

Similarly, the lipid-based probes of this invention can be used to similarly investigate the degree of lipid/protein interaction.

Cellular Uptake of Polypeptides.

It was also a discovery of this invention that attachment of a hydrophobic protecting group to a polypeptide enhances uptake of that polypeptide by a cell. The effect is most pronounced when the polypeptide also bears a fluorophore, more preferably two fluorophores (see, Example 9). Preferred hydrophobic groups include, but are not limited to Fmoc, benzyloxycarbonyl, Xanthyl (Xan), Trityl (Trt), 4-methyltrityl (Mtt), 4-methoxytrityl (Mmt), 4-methoxy-2, 3,6-trimethyl-benzenesulphonyl (Mtr), Mesitylene-2-sulphonyl (Mts), 4,4'-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA).

This invention thus provides a method of delivering a polypeptide into a cell. The method involves providing the polypeptide having attached at least two fluorophore molecules and a hydrophobic group, more preferably an Fmoc group and then contacting the cell with the polypeptide.

It will be appreciated that where the peptide, oligonucleotide, oligosaccharide, or lipid is to be delivered in vivo for diagnostic end point or for therapeutic purposes, fluorophores and a hydrophobic group having reduced or no toxicity are preferred. Such potential molecules can be found among biological molecules such as steroids. The relatively flat and hydrophobic fluorophores that are known for H-type dimer formation can be replaced with similarly hydrophobic and structurally rigid and/or flat fused rings found, for example, in steroid molecules. A steroid derivative, e.g., a smaller than full steroid molecule, two to three fused six member ring molecules can be cross linked via usual cross linkers to provide a size and an over all hydrophobicity comparable to the Fmoc and other hydrophobic groups described herein. Since safe metabolic pathways exist for larger molecule consisting of these smaller building blocks, the toxicity of such hybrid molecules is expected to be small. In a preferred embodiment, the hydrophobic molecules are in a size range of about 17 by 12 Angstroms. It will be appreciated that where the peptide is to be delivered in vivo fluorophores of reduced or no toxicity are preferred. Toxicities of numerous fluorophores are well known to those of skill in the art (see, e.g., Haugland, *Handbook of Fluorescent Probes and Research Chemicals,* 6th Ed., Molecular Probes, Eugene, Oreg. (1996). In addition, toxicity (e.g., $LD_{50}$) can be readily determined according to standard methods well known to those of skill i nthe art.

Activity Detection Kits

The present invention also provides for kits for the detection of protease activity in samples. The kits comprise one or more containers containing the fluorogenic protease indicators of the present invention. The indicators may be provided in solution or bound to a solid support. Thus the kits may contain indicator solutions or indicator "dipsticks", blotters, culture media, and the like. The kits may also contain indicator cartridges (where the fluorogenic indicator is bound to the solid support by the "acceptor" fluorophore side) for use in automated protease activity detectors.

The kits additionally may include an instruction manual that teaches the method and describes use of the components of the kit. In addition, the kits may also include other reagents, buffers, various concentrations of protease inhibitors, stock proteases (for generation of standard curves, etc), culture media, disposable cuvettes and the like to aid the detection of protease activity utilizing the fluorogenic protease indicators of the present invention.

It will be appreciated that kits may additional or alternatively comprise any of the other indicators described herein (e.g., nucleic acid based indicators, oligosaccharide indicators, lipid indicators, etc ). In this instance the kit will facilitate detection of the particular activities/compounds/interactions for which the particular indicator backbone is a substrate or binding agent.

Protease Inhibitors

It was also a discovery of this invention that the protease indicators can also act as protease inhibitors. Protease inhibitors and protease substrates share several basic properties such as ability to bind to protease's catalytic substrate binding site, and form a relatively stable complex with a protease. Hence, many normal substrates or their fragments exhibit competitive substrate inhibition at higher concentrations. The inhibition is competitive since the inhibitor binds to the same substrate binding site of the protease whereby it competes with the native substrate in binding to the protease's catalytic domain.

This invention provides two novel approaces for protease inhibitor design. In the first approach, a normal substrate is redesigned such that it binds to protease well, but has a reduced (slow or non-existent) hydrolysis rate. The slow hydrolysis rate is achieved by introducing an altered (different) conformation and/or conformational flexibility into the protease recognition domain. After the (e.g., native) substrate binds to the protease's substrate binding site, the conformation of the peptide bond between $P_1$ and $P_1'$ is distorted into a transition conformation of a given protease's peptide bond hydrolysis reaction. If this peptide bond as well as adjacent peptide bonds are altered such that they are not distortable then the hydrolysis rate will be reduced as compared to a substrate whose cleavage site peptide bond is easily distorted into the desired transition conformation. This approach is illustrated in Example 16 which shows how one can vary the hydrolysis rate of a substrate without changing the protease recognition amino acid sequences.

In a second approach, the inhibitor is produced by replacing the critical $P_1$ or $P_1'$ residue which makes it difficult to distort the cleavage site peptide bond. Normally, the amino acid side chains of $P_1$ and $P_1'$ residues interact specifically with the side chains of the protease catalytic domain. These specific interaction facilitate coordination of the peptide bond distortion into a transition conformation of the hydrolysis reaction. Thus, for example, when the critical $P_1$ residue of aspartic acid residue in the CPP32 protease substrate is replaced with non-charged asparagine then normal interaction between the substrate and protease does not take place even though the modified substrate binds to the protease's substrate binding site. Again, this leads to a slower or zero hydrolysis rate. The example of this $P_1$ residue substitution effect in designing an inhibitor is illustrated by the properties of the DEVN (SEQ ID NO:3) peptide (see, e.g., FIG. 5 and Example 12). The biological conformation that the substrate DEVN (SEQ ID NO:3) is an inhibitor is demonstrated in Example 13. Additional evidence that the peptide DEVN (SEQ ID NO:3) does bind to protease is given in Example 15.

The $P_1'$ residue can be changed to introduce either charged amino acid side chains or a structurally rigid, e.g., proline, residue as illustrated in the Table 3, substrate sequences for Hepatitis C viral protease substrate NS3 NS5A/5B of DVVCCSMS (SE ID NO:141) (normal substrate) and DVVWCCPdMS (inhibitor). The underlined residues are the $P_1$ residues.

EXAMPLES

The invention is illustrated by the following examples. These examples are offered by way of illustration, not by way of limitation.

Example 1

Synthesis of Fluorogenic Molecule for Detecting Protease Activity a) Synthesis of the peptide backbone.

The amino acid sequences Asp-Ala-Ile-Pro-Nle-Ser-Ile-Pro-Cys (SEQ ID NO:142) (where $C^1$ is Asp-Ala-Ile, P is Pro-Nle-Ser-Ile (SEQ ID NO:6) and $C^2$ is Pro-Cys) and Asp-Ala-Ile-Pro-Met-Ser-Ile-Pro-Cys (SEQ ID NO:143) (where $C^1$ is Asp-Ala-Ile, P is Pro-Met-Ser-Ile (SEQ ID NO:5) and $C^2$ is Pro-Cys) were synthesized manually utilizing a t-Boc Cys-Pam resin and t-Boc chemistry using the protocol for a coupling cycle given below in Table 5. The synthesized peptides were deprotected by treatment with hydrofluoric acid for 60 minutes under anhydrous conditions at a temperature of 4° C.

TABLE 5

Reaction steps for one coupling cycle (addition of one amino acid) for the synthesis of the peptide backbone of the fluorogenic protease inhibitors.

| Step | Process | Time (min) | # Repeats |
|---|---|---|---|
| 1 | TFA/DCM Pre-wash 15 ml, 50% (v/v) or 35% (v/v) | 2.0 | 1 |
| 2 | TFA/DCM Main Wash 15 ml, 50% (v/v) or 35% (v/v) | 28.0 | 1 |
| 3 | DCM washes, 10 ml | <0.33 | 4 |
| 4 | DIEA/DCM, 10% (v/v), 10 ml | 2.0 | 1 |
| 5 | DIEA/DCM, 10% (v/v), 10 ml | 8.0 | 1 |
| 6 | DCM washes, 10 ml | <0.33 | 5 |
| 7 | Resin wash with NMP (or DMF) | <0.33 | 5 |
| 8 | 5-fold excess t-Boc-amino acid with HOBT and DIPC in NMP or DMF | 90 to 120 | 1 |
| 9 | DCM wash | <0.33 | 1 |
| 10 | MeOH wash | <0.33 | 1 |
| 11 | DCM washes | <0.33 | 2 |
| 12 | DIEA wash | <0.33 | 1 |
| 13 | DCM washes | <0.33 | 3 |
| 14 | Ninhydrin | 5.0 | 1 |
| 15 | 3-fold excess t-Boc-amino acid/DIPC/DCM | 30 | 1 |
| 16 | MeOH wash | <0.33 | 1 |
| 17 | DCM washes | <0.33 | 5 |
| 18 | Ninhydrin test | 5 | 1 |
| 19 | Go to step 1 to couple next amino acid | | |

Crude post-HF deprotected and cleaved peptides were purified by reverse phase HPLC using a preparative $C_{18}$ column (YMC, Inc., Charlestown, N.C., USA). The solvent system utilized was water and acetonitrile containing 0.1% (v/v) trifluoroacetic acid (TFA). HPLC was performed using the following gradient at a flow rate of 10 ml/minute:

TABLE 6

HPLC gradient for purification of the peptide backbone.

| Time (min) | % Solvent A ($H_2O$ with TFA (0.1%)) |
|---|---|
| 0 | 100 |
| 7 | 100 |
| 8 | 90 |
| 68 | 50 |
| 78 | 50 |

Purification of methionine-containing peptides required subjecting the peptide to reducing conditions, e.g., dithiothreitol (DTT) and heat, to reduce methionine oxide to methionine. This reductive treatment was carried out by dissolving the peptide in 150 mM sodium phosphate buffer with 1 mM DTT, pH 7.5 for 30 minutes at 60 to 80° C. The reduction could also have been carried out under a weak acidic pH with 0.03 N HCL but would have required a longer heating time. The subsequently HPLC purified methionine containing peptides were found to oxidize upon sitting either in aqueous solution or lyophilized form. The oxidized peptides were found to be reducible repeating the above reducing condition.

b) Derivatization of the peptide backbone with the fluorophore molecules.

The peptides were derivatized sequentially with donor and acceptor fluorophores. Specifically the donor fluorophore (5'-carboxytetramethylrhodamine (C2211), available from Molecular Probes, Inc. Eugene, Oreg., USA) was first covalently linked to the amino terminus of the peptide. The peptide and the probe, at a molar ratio of 3:1 peptide to probe, were dissolved in a minimal amount of solvent NMP (N-methyl pyrolidone), usually 20 to 60 µl. One molar equivalent of DIEA (diisopropyl ethyl amine) was also added to the reaction mixture. The reaction was then incubated at 37° C. with times ranging between 12 hours and 3 days. After two days an additional 1 molar equivalent of dye molecule was sometimes added. The derivatization reached nearly maximal yield by 3 days. The peptide bearing the single C2211 fluorophore was then HPLC purified as described below.

The second (acceptor) fluorophore (rhodamine X acetamide (R492)) was then coupled to the carboxyl cysteine of the peptide by a linkage between the iodoacetamide group of the fluorophore and the sulfhydryl group of the terminal cystein. This coupling was accomplished as described above for the first fluorophore.

The complete fluorogenic protease indicator was then purified by HPLC using an analytical reverse phase $C_3$ columns (2 ml void volume) from Waters Associates Inc. (Milford, Mass., USA) using the gradient shown in Table 6 running at 1 ml/minute.

TABLE 7

HPLC gradient for purification of the peptide bearing fluorophores.

| Time (min) | % Solvent A ($H_2O$ with TFA (0.1%)) |
|---|---|
| 0 | 100 |
| 1 | 100 |
| 2 | 80 |

TABLE 7-continued

HPLC gradient for purification of the peptide bearing fluorophores.

| Time (min) | % Solvent A (H$_2$O with TFA (0.1%)) |
|---|---|
| 6 | 80 |
| 66 | 50 |

The slow reactivity of both the amino and sulfhydryl groups in coupling the fluorophores appeared to be a function of the folded structure of the peptide backbone which sterically hindered access to the peptide's reactive groups. Control experiments using irrelevant linear peptides showed considerably faster linking. The folded structure is also supported by the results reported in Examples 2 and 3. A computer energy minimization model of the peptide also indicated possible preference for the peptide to assume a folded structure rather than an open extended structure. This is due largely to the presence of the conformation determining regions containing the two proline residues.

Example 2

Alternative Synthesis of Protease Activity Indicators a. Fmoc-protected peptide backbone synthesis The amino acid sequences listed in Table 8 were synthesized manually utilizing Fmoc chemistry and 2-chlorotritylchloride resin employing the protocol for a coupling cycle given below in Table 7.

TABLE 8

Protease indicator peptide backbones.

| | S$^1$ | C$^1$ | P | C$^2$ | S$^2$ | SEQ ID NO: |
|---|---|---|---|---|---|---|
| 1. | | Asp-Ala-Ile- | Pro-Nle-Ser-Ile- | Pro-Cys- | Gly-Tyr | 144 |
| 2. | | Asp-Ala-Ile- | Pro-Nle-Ser-Ile- | Pro-Lys- | Gly-Tyr | 145 |
| 3. | Lys- | Asp-Ala-Ile- | Pro-Nle-Ser-Ile- | Pro-Lys- | Gly-Tyr | 146 |
| 4. | | Asp-Aib-Thr- | Gly-Arg-Thr-Gly- | Pro-Lys- | Gly-Tyr | 147 |
| 5. | Lys- | Asp-Aib-Thr- | Gly-Arg-Thr-Gly- | Pro-Lys- | Gly-Tyr | 148 |

The synthesized peptides were cleaved from the 2-chlorotritylchloride resin with mild acid treatment (vol/vol ratio of 2:7:1 Acetic acid: Dichloromethane: Trifluoroethanol) at room temperature for 30 minutes. A 10 ml aliquot of this peptide resin cleavage solution was added to 0.1 gm of dried peptide resin. The following side chain protecting groups were used in the synthesis: t-butyl for Asp, Ser, Thr, and Tyr residues, S-trityl and S-t-butylthio for Cys residues, and t-Boc, Fmoc and 4-methyltrityl for lysine residues.

The side chain protecting groups as well as the Fmoc group on the alpha amino group of the synthesized peptide were not cleaved with this mild acid peptide resin cleavage reagent. The protected peptide containing solution was lyophilized. The lyophilized protected peptides were further treated by either 30% (v/v) TFA in dichloromethane for t-Boc deprotection, 20%(v/v) piperidine in DMF or N-methylpyrolidone for Fmoc deprotection, 1 to 5% (v/v) trifluoroacetic acid (TFA) in water, or 1% TFA/5% triisopropylsilane in DCM, for 4-methyltrityl deprotection, aqueous mercaptoethanol (10%) for S-t-Butylthio deprotection, TFA:phenol:water:thioanisol:ethanedithiol=85:5:5:2.5:2.5 for t-Butyl, t-Boc and S-Trityl deprotection, and TFA:phenol:water=90:5:5 for t-Butyl and t-Boc deprotection.

Fully or partially side-chain deprotected peptides were purified by reversed phase HPLC using a C18 column with a water/acetonitrile gradient containing 0.075% (v/v) TFA in each solvent.

b. Derivatization of the protected peptide backbone with fluorophores.

The fully purified protected peptide was further treated with the appropriate reagents for selective deprotection of the side chains of Cys or Lys residues. The use of three different protecting groups, i.e., t-Boc, Fmoc, and 4-methyltrityl group, for the epsilon ($\epsilon$) amino group protection of lysine, allowed selective deprotection, and thus, selective derivatization of a specific lysine residue.

For example, about 1 mg of protected peptide was dissolved in a minimal amount of N-Methylpyrolidone. The appropriate fluorophore derivatized with a succimidyl ester reactive functional group was added to the peptide solution at a 1.2 to 2 fold molar excess of reactive fluorophore over the peptide. A ten-fold mole excess of diisopropylethylamine (DIEA) was also added to the reaction mixture. The reaction was allowed to proceed at room temperature for 2 to 4 hours. The derivatized peptides were purified by reversed phase HPLC using a C18 or C4 column and 0.075% (v/v) TFA-containing water/acetonitrile solvent system.

The derivatization of the peptide with the first fluorophore was facilitated by the presence of at least one very hydrophoic group such as Fmoc. The presence of such a hydrophobic group on the peptide allowed elution (e.g. partitioning) of the derivatized peptide away from fluorophore contaminants and reaction by-products and degradation products that accumulate as the derivatization reaction is allowed to proceed.

Deprotection of the Fmoc group was then carried out after one amino group or sulfhydryl group was derivatized with the desired fluorophore. The fluorophores utilized for the amino group conjugation were C1171, 5-(and 6-)carboxytetramethylrhodamine succinimidyl ester, C1309, 5-(and 6-)carboxy-X-rhodamine succinimidyl ester, and fluororescein isothiocyanate. After deprotection, a second fluorophore was added in a manner identical to the addition of the first.

TABLE 9

Reaction steps for one coupling cycle (addition of one amino acid) for the synthesis of the peptide backbone of the fluorogenic protease substrates.

| Step | Process | Time (min) | # repeats |
|---|---|---|---|
| 1. | Wash resin with DCM. | 1 | 1 |
| 2. | Wash resin with DMF. | 1 | 2 |
| 3. | 20% piperidine in DMF. | 5 | 1 |
| 4. | 20% piperidine in DMF. | 15 | 1 |
| 5. | Wash resin with DCM. | 1 | 4 |
| 6. | Wash resin with NMP. | 1 | 2 |

TABLE 9-continued

Reaction steps for one coupling cycle (addition of one amino acid) for the synthesis of the peptide backbone of the fluorogenic protease substrates.

| Step | Process | Time (min) | # repeats |
|---|---|---|---|
| 7. | Preactivate 2 to 4 fold mole excess Fmoc-aa, PyBoP, HoBt, and N-methyl-morpholine in NMP. | 5 | 1 |
| 8. | Add the above pre-activated Fmoc-AA coupling mixture. | 45 | 1 |
| 9. | Wash resin with DCM. | 1 | 4 |
| 10. | Wash resin with methanol. | 1 | 1 | c. Molecular weight characterization of the derivatized peptides.

Since during, or after, the derivatization of the protected peptides a strong acid deprotection step was sometimes used to remove the remaining t-Butyl groups from the various amino acid side chains, there was a possibility that either aromatic amino acids or fluorophores might have been chemically modified. The molecular weights of the derivatized and purified peptides were therefore determined.

Molecular weights were measured using a matrix assisted laser desorption time of flight mass spectrometer, Kompact MADLI I by Kratos Analytical. The Mass spectometer was calibrated with Leucine-Enkaphelin (556.6 amu), Bradykinin (1061.2 amu), and Mellitin (2847.5 amu). The sample matrix used was α-cyano-4-hydroxycinnamic acid. Samples were applied to target and 1 ml 0.1% TFA in ethanol solution was added on the target and then dried down. Cumulative mass spectral data from 50 laser shots were collected and a peak corresponding to the parent mass peak plus 1 for each sample was determined. The results are summarized on Table 10.

The good agreement between the calculated and experimentally determined mass values indicates the absence of any side reaction products in the final purified fluorophore-conjugated peptides.

TABLE 10

Calculated and determined molecular mass of the derivatized peptide protease substrates. Ther vertical and horizontal line indicate the fluorophore's attachment site. The symbols FL, C1171 and C1309 denote fluorophores fluoroscein isothionate, 5-(and-6)-carboxytetramethylrhodamine succinimidyl ester, and 5-(and-6)-carboxy-X-rhodamine succinimidyl ester, respectively. ND denotes not determined.

| | Compound | Calculated Mass (amu) | Observed Mass (amu) | SEQ ID NO: |
|---|---|---|---|---|
| 1. | C1171-DAIP(Nle)SIPKGY with C1309 attached | 2101.2 | 2102.6 | 149 |
| 2. | C1309-DAIP(Nle)SIPKGY with C1171 attached | 2101.2 | 2097.8 | 150 |
| 3. | C1171-DAIP(Nle)SIPKGY with C1171 attached | 1997.0 | 1997.6 | 151 |
| 4. | DAIP(Nle)SIPKGY with C1309 attached | 1688.7 | 1685.9 | 152 |
| 5. | C1309-DAIP(Nle)SIPKGY | 1688.7 | 1688.1 | 153 |
| 6. | DAIP(Nle)SIPKGY with C1171 attached | 1585.5 | 1585.8 | 154 |
| 7. | C1171-DAIP(Nle)SIPKGY | 1585.5 | 1583.7 | 155 |
| 8. | Fl-DAIP(Nle)SIPKGY with Fl attached | | ND | 156 |
| 9. | C1309-DAIP(Nle)SIPKGY with C1309 attached | | ND | 157 |
| 10. | KDAIP(Nle)SIPKGY with C1171 and C1309 attached | | ND | 158 |

TABLE 10-continued

Calculated and determined molecular mass of the derivatized peptide protease substrates. Ther vertical and horizontal line indicate the fluorophore's attachment site. The symbols FL, C1171 and C1309 denote fluorophores fluoroscein isothionate, 5-(and-6)-carboxytetramethylrhodamine succinimidyl ester, and 5-(and-6)-carboxy-X-rhodamine succinimidyl ester, respectively. ND denotes not determined.

| | Compound | Calculated Mass (amu) | Observed Mass (amu) | SEQ ID NO: |
|---|---|---|---|---|
| 11. | KDAIP(Nle)SIPKGY<br>C1171⎯⎤          ⎦⎯C1171 | | ND | 159 |

Example 3

The Fluorogenic Protease Indicators Provide a Strong Signal When Digested

In order to demonstrate that the fluorogenic protease indicators of this invention are easily digested by a protease, the degree of cleavage was determined by assaying for the appearance of indicator cleavage products in the presence of a protease.

Approximately 1 microgram of protease indicator, having the formula $F^1$-Asp-Ala-Ile-Pro-Nle-Ser-Ile-Pro-Cys-$F^2$ where $F^1$ is a (SEQ ID NO:1) donor fluorophore (5'-carboxytetramethylrhodamine (C2211)) linked to aspartic acid via the alpha amino group and $F^2$ is an acceptor fluorophore (rhodamine X acetamide (R492)) linked via the sulfhydryl group of the cysteine was dissolved in a buffer consisting of 50 mM sodium phosphate, 1 mM EDTA at pH 8.9. To this solution was added 1 unit of elastase. The solution was analyzed by HPLC before and about 30 minutes after the addition of elastase. The digestion was carried out at 37° C. The HPLC separated components were monitored at a wavelength of 550 nm which allowed detection of both the C2211 fluorophore the R492 fluorophore and at 580 nm which allowed detection of the R492 fluorophore.

Figure 1B:
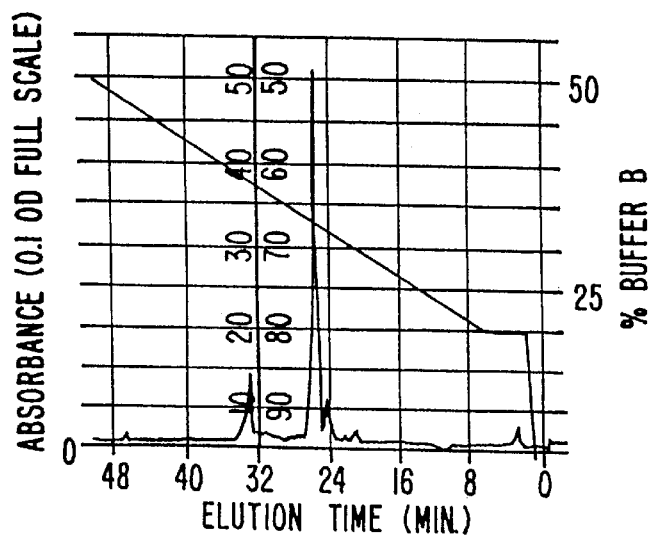
Figure 1C:
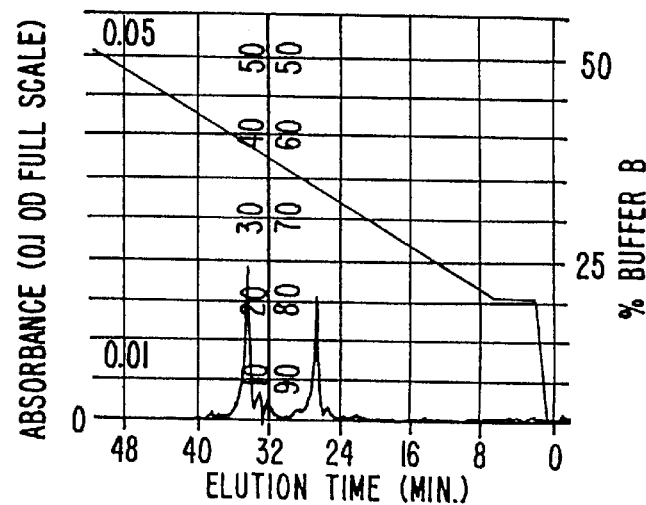

The results are indicated in FIG. 1 which shows the HPLC profiles of the fluorogenic protease indicator solution before and after addition of the protease elastase. FIG. 1(a) shows the HPLC before addition of the elastase showing a single peak representing the intact fluorogenic protease inhibitor. After addition of the elastase (FIGS. 1(b) and 1(c)) there was no trace of the late eluting single peak (FIG. 1(a)) indicating complete digestion of the fluorogenic protease indicator. In addition, the two predominant peaks in FIG. 1(b) and 1(c) indicate that the digestion occurred primarily at a single site. There are a few smaller peaks indicating a low degree of digestion at other sites within the peptide sequence, however, the striking predominance of only two digestion peaks suggests that these secondary sites were not readily accessible to the elastase.

Changes in the emission spectrum of the fluorogenic protease indicator after the addition of an elastase protease was monitored using an SLM spectrofluorometer model 48000 with slit widths set at 4 nm on both the excitation and emission sides. All measurements were carried out at 37° C.

Figure 2A:
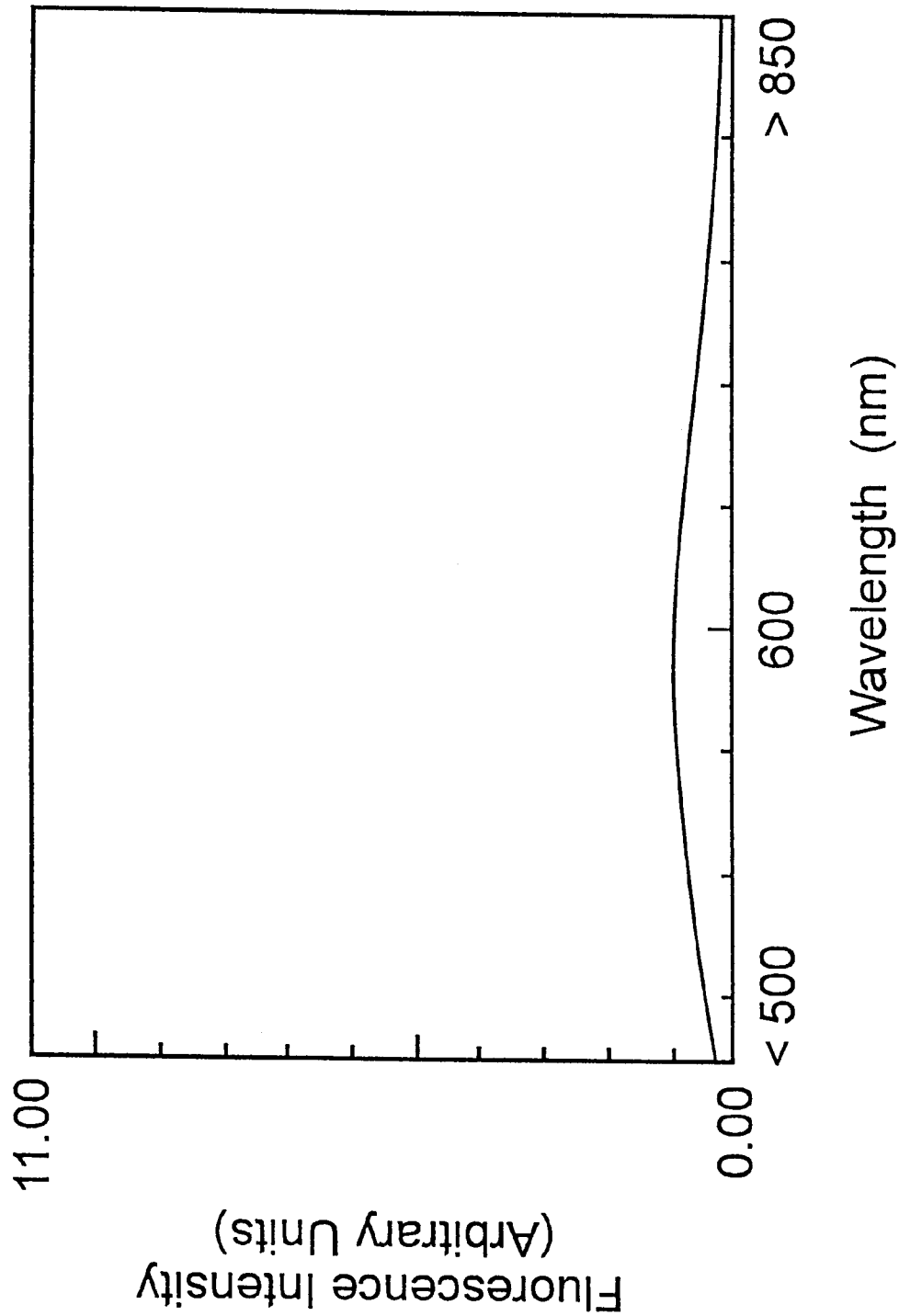
FIGS. 2A and 2B show the emission spectra of the D-NorFES-A fluorogenic protease indicator (FIG. 2A) before and (FIG. 2B) after the addition of elastase.
Figure 2B:
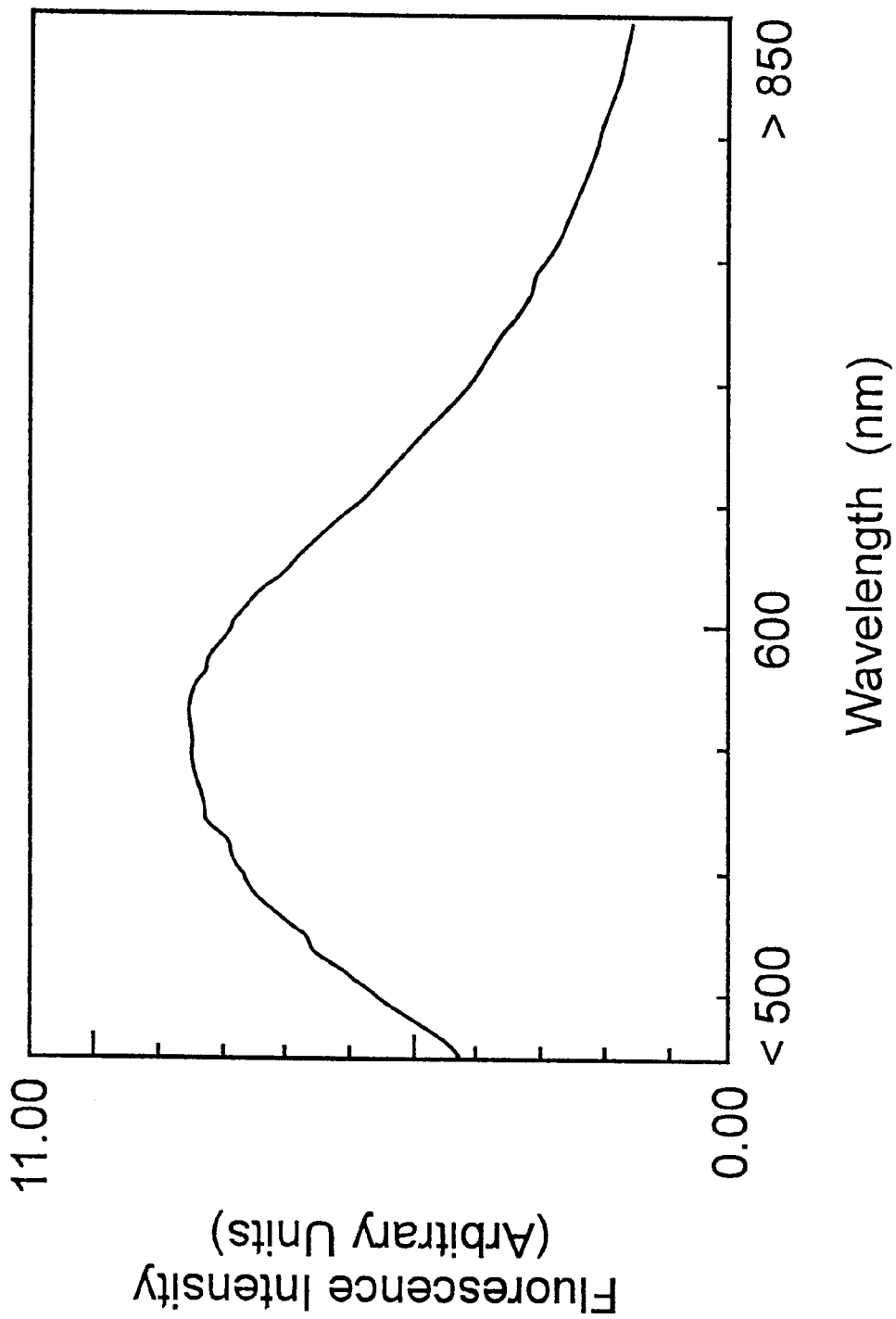
Figure 3:
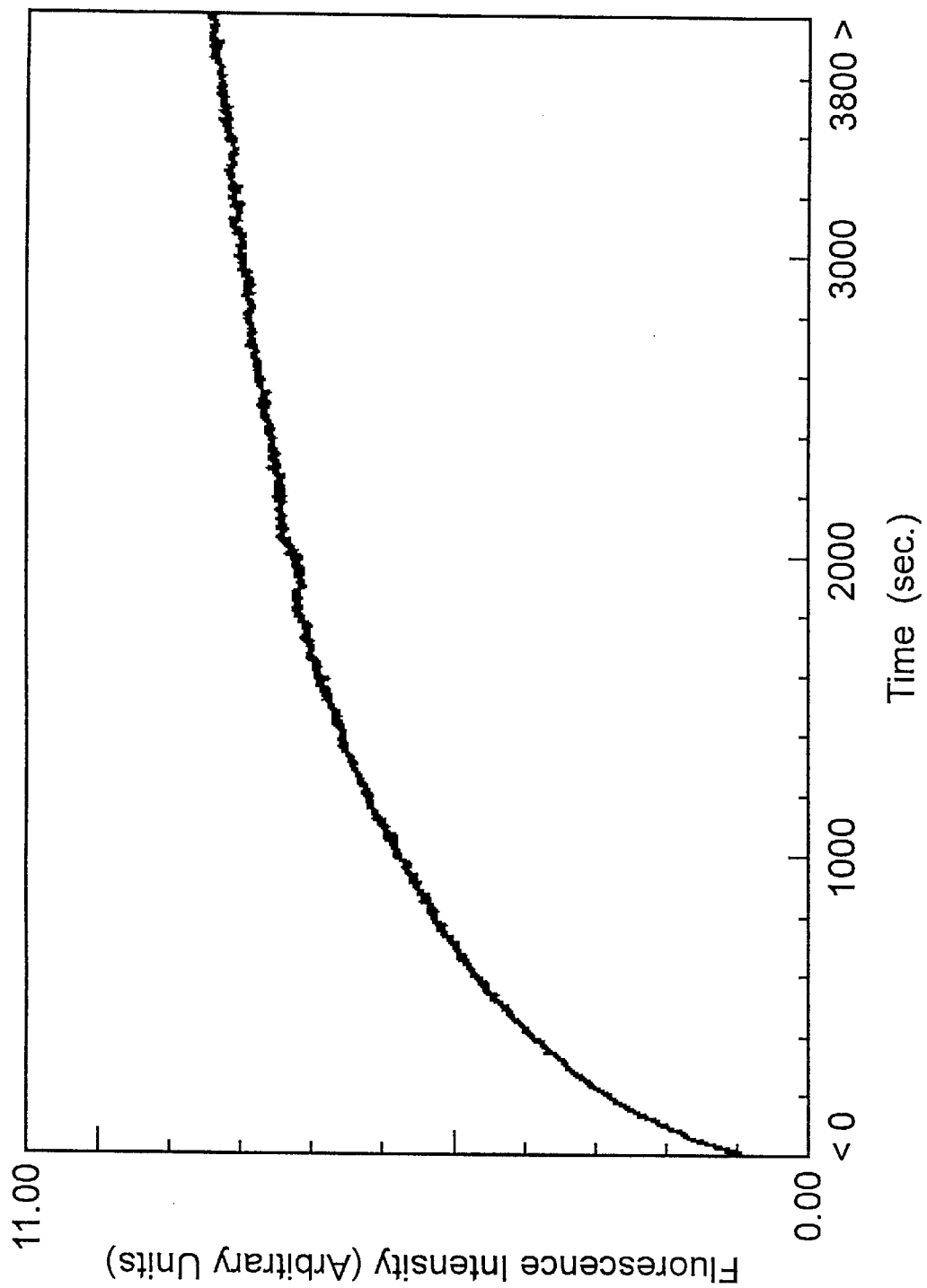
FIG. 3 shows the time-dependent increase of the fluorogenic protease indicator of FIG. 1, as a function of time after addition of 1 unit of elastase.

Spectra in FIG. 2 show emission of the fluorogenic protease indicator (a) before and (b) after addition of elastase, while the time dependent increase of the indicator's donor fluorophore emission intensity, after addition of elastase, is plotted in FIG. 3. The fluorogenic protease inhibitor showed more than a 10 fold increase in fluorescence at 589 nm after treatment with the elastase protease (FIG. 2(a) compared to FIG. 2(b)) with over a 5 fold increase in fluorescence occurring within the first 1000 seconds of exposure to the protease. The changes in intensity between treated and untreated indicators are, to some degree, a function of slit widths used, since they represent the signal integrated across the particular slit width. Thus, if wider slit widths were used (e.g. 8 or 16 nm slits) an even greater signal would be provided in response to digestion.

Example 4

The Fluorescence Signal Was Due to Intramolecular Energy Dequenching

In order to show that the fluorescence increase observed after protease treatment was due to intramolecular energy dequenching, the signal produced by elastase digestion of the fluorogenic protease indicator was compared to the signal produced by elastase treatment of the same peptide backbone coupled to either $F^1$ (C2211) or to $F^2$ (R492). The change in fluorescence intensity of the donor fluorophore after addition of 1 unit of elastase to equal concentrations of the double-fluorophore molecule and the two single-fluorophore molecules.

Figure 4B:
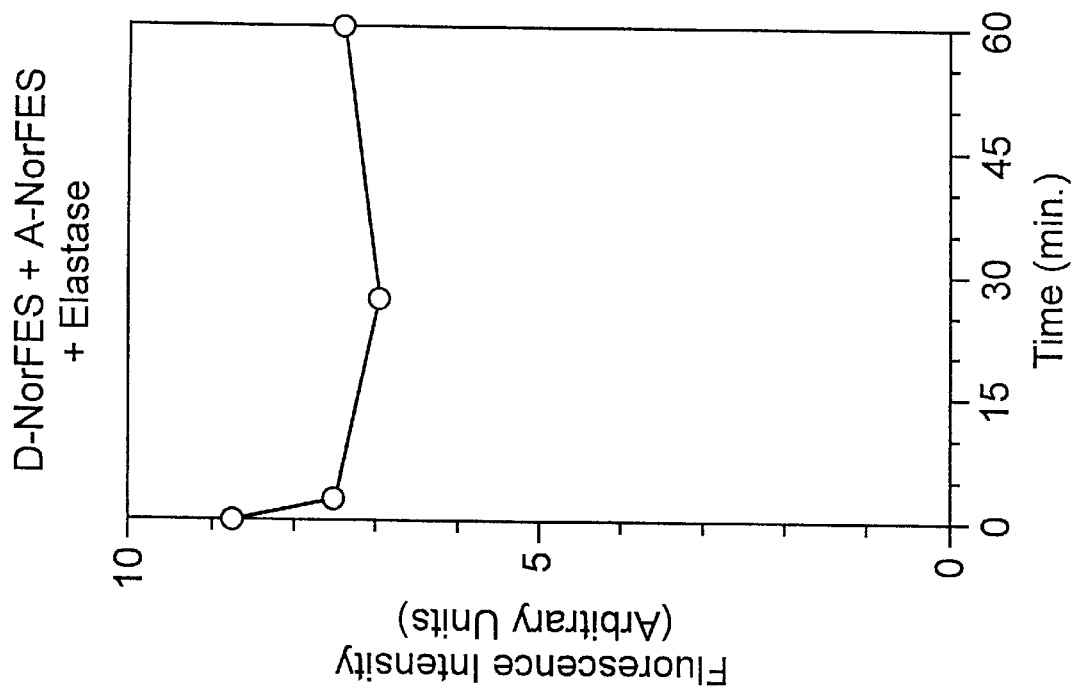
FIGS. 4A and 4B show the fluorescence intensity of the donor fluorophore as a function of time after addition of 1 unit of elastase.
Figure 4A:
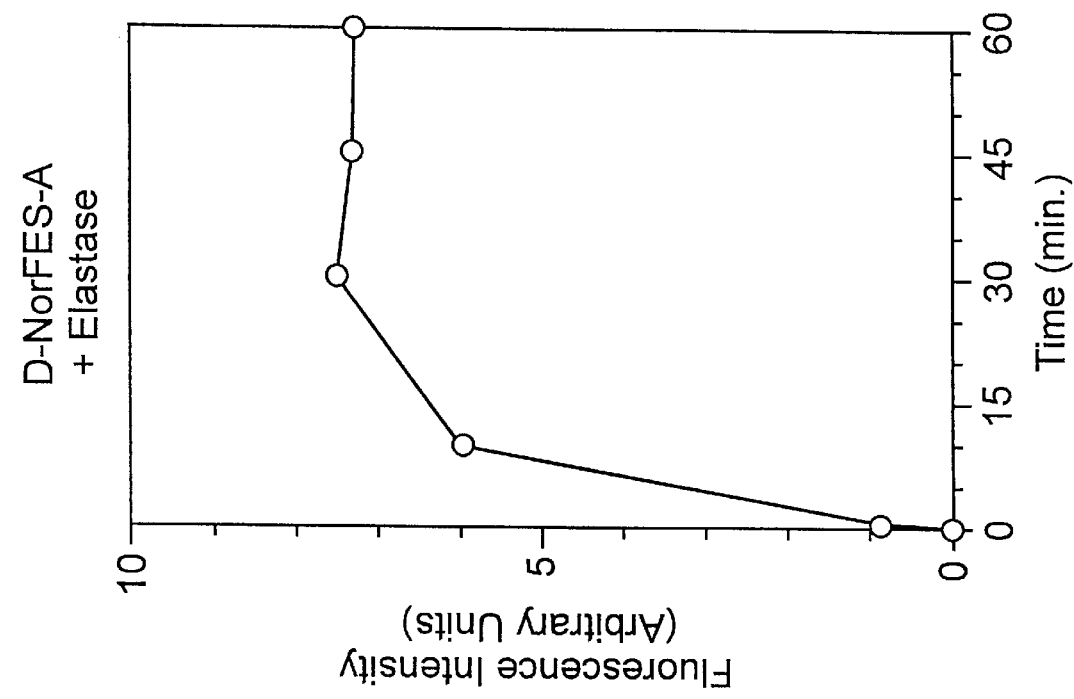

The results are illustrated in FIG. 4. The double-fluorophore molecule showed nearly complete quenching initially, followed by a dramatic increase in fluorescence after addition of the elastase which reached a constant value approximately 30 minutes after addition of the elastase (FIG. 4(a)). In contrast, the two single-fluorophore molecules showed virtually no initial quenching and no significant change in fluorescence after addition of the elastase. In fact, the fluorescence level was comparable to the fluorescence level of the fully digested double-fluorophore indicator molecule (FIG. 4(b)).

These results indicate that the increase in fluorescence intensity of the fluorogenic protease indicator is due to interruption of the resonance energy transferred intramolecularly from the donor fluorophore to the acceptor fluorophore and not to interaction between the fluorophore and the peptide backbone. This is significant since it is known that upon binding to a large protein or hydrophobic peptide the fluorescence of many hydrophobic fluorophores is quenched.

Example 5

Without being bound to a particular theory, it is believed that the fluorogenic protease indicators of the present invention achieve a high degree of protease specificity due to their folded structure, more particularly due to their relative rigid U-shaped conformation. The fluorescence obtained from the molecule reflects the average separation of two fluorophores. Thus, it was predicted that if the protease indicators existed in a relatively unfolded or flexible state, conditions that tend to cause unfolding (denaturation) would have little or no effect on the fluorescence of the molecule in the absence of a protease. Conversely, if the molecule is relatively rigid, then denaturing conditions would be expected to increase the fluorescence signal as the average separation of the fluorophores would be expected to increase thereby decreasing the quenching effect.

Thus, the effect of denaturing conditions on the fluorescence of the fluorogenic protease indicator in the absence of a protease was determined. First the change of fluorescence of the indicator of Example 1, as a function of added chaotropic reagent concentration (2M or 8M urea) was measured. When the fluroogenic protease indicator was denatured with a chaotropic reagent the fluorescence intensity increased with time to a plateau as the molecule denatured (unfolded).

These data indicate that the fluorogenic protease indicator normally exists in a stable folded conformation created by the conformation determining regions, as was predicted by a model based on an energy minimization algorithm. The plateau fluorescence level represents residual quenching of the fluorophores still joined by the fully denatured peptide backbone. Digestion of the extended (denatured) peptide results in greater than a 2 fold increase in fluorescence as the fluorophores are able to move farther away from each other.

Example 6

Quenching and Release of a Peptide Doubly-Labeled with One Fluorophore

It was a surprising discovery of this invention that the peptide backbones of this invention doubly labeled with one fluorophore still achieve fluorescence quenching thus suggesting quenching through another mechanism besides resonance energy transfer.

In order to assess the extent ground-state dimerization and collisional quenching contribute to the total observed quenching, the series of doubly-labeled peptides listed in Table 11 was synthesized.

In addition to comparing absorption spectra of the dyes alone with the NorFes peptides singly labeled with each dye, emission spectra taken before and after cleavage were compared to determine the percent of quenching and the existence of fluorescent signal quenching by means other than resonance energy transfer (RET).

Fluorophores were linked to the amino terminus via the a-amino group of Aspartic acid residue (D) and to the c-amino group of lysine (K). Labeling was accomplished by the displacement of a succinimidyl group linked to C1171 or C1309. The structure of the peptide, called NorFES-KGY is:

As determined from absorption spectroscopy, all doubly-labeled peptides, except fluorescein-NorFES-fluorescein, showed the existence of so called ground-state dimers. This was indicated by shift of absorption maxima to shorter wavelengths as well as a shape change of the absorption spectra as compared with the spectra for the enzyme digested doubly-labeled samples. Upon cleavage with elastase, the ground-state dimers were destroyed and the resulting spectra were the same as a solution containing equal concentrations of the respective singly labeled peptides.

Without being bound to a particular theory, it is believed that the ground-state dimer formation observed in the compounds designed and synthesized according to the present invention indicates that the U-shaped conformation of the peptide backbone brings the fluorophores into close spatial proximity thus allowing overlap of electron orbitals of the two fluorophores resulting in reciprocal quenching through ground-state dimerization. It was a surprising discovery that the polypeptides of this invention allowed the formation of ground-state dimers at a significantly lower dye concentration than previously observed. For example, ground-state dimerization of free fluorescein dye in solution was only observed at concentrations higher than than 0.74 M, ground-state dimerization of free Eosin dye in solution was only observed at concentrations higher than $2.8 \times 10^{-2}$ M (see, Forster and Konig (1957) *Zeitschrift fur Electrochemie*, 61: 344), and ground-state dimerization of Rhodamine B dye in solution was only observed at concentrations higher than $6 \times 10^{-4}$ M (see Arbeloa and Ojeda (1982) *Chemical Physics Letters*, 87: 556). In contrast, in the present invention, the effects are observed at $4.0 \times 10^{-7}$ M or about a 1000 fold lower concentration than the reported values.

The observation of the ground-state dimer for the compounds synthesized according to the present invention predicted a significant level of fluorescent quenching for doubly-labeled peptide with the same fluorophore as those compounds listed in Table 11. In fact this prediction was confirmed; a comparison of C1171-NorFES-KGY-C1309 with C1171-NorFES-KGY-C1171, i.e., the hetero doubly-labeled with the homo doubly-labeled peptides, indicates the degree of quenching is slightly higher in the hetero- vs. the homo-(94 vs. 90%). The fluorescein derivative, however, exhibited only 55% quenching. The symbols $I_0$ and $I_c$ for the percent fluorescent quenching (%Q) refer to the fluorescence intensity for the intact labeled peptide and the enzyme digested labeled peptide solution respectively.

TABLE 11

Cleavage rate (T½) and percentage of quenching (% Q) of hetero- and homo-labeled peptides. T½ is the time in seconds after addition of a protease (e.g. elastase) at which the fluorescence signal is ½ maximum. The symbols $I_0$ and $I_c$ refer to the fluorescence intensity (I) for the intact labeled peptide and the enzyme digested labeled peptide solution respectively.

| Compound | T½ | % Q-(1 − ($I_0/I_c$)) × 100 |
|---|---|---|
| C1171-NorFes-C1309 | 80 | 94 |
| C1171-NorFes-C1171 | 44 | 90 |
| C1171-NorFes-C1171 | 44 | 90 |
| C1309-NorFes-C1309 | 152 | 90 |
| Fl-NorFes-Fl | 18 | 55 |
| C1171-NorFes-C1309 | 80 | 94 |
| C1171-K-NorFes-C1309 | 125 | 97 |
| C1171-NorFes-C1171 | 44 | 90 |
| C1171-K-NorFes-C1171 | 84 | 92 |

The substrate sequence could be extended by one amino acid residue and the fluorophore could be attached through the episilon amino group on the lysine residue's side chain without major perturbation to the amount of observed quenching. Specifically, this addition (peptides designated K-NorFES-KGY) resulted in a slight decrese in cleavability rate and a very slight increase in the percent quenching for both the hetero- and homo-doubly-labeled peptide (in the K-NorFES-KGY peptides, N-terminal labeling was via the epsilon-amino group of lysine rather than the α-amino terminus).

Rates of cleavage ($T_{1/2}$) of these substrates by elastase were also measured by recording the time after addition of the protease at which the signal was one-half maximum (see, Table 11). A comparison of three homo-doubly-labeled peptides, i.e., NorFES-KGY labeled with two molecules of C1171, C1309, and fluorescein (FI), shows the order of cleavability to be: FI-NorFES-KGY-FI>C1171-NorFES-KGY-C1171>C1309-NorFES-KGY-C 1309.

Example 7

Use of Homo-Doubly Labeled Protease Indicators

In order to demonstrate the efficacy of the protease indicators of this invention in vitro, cells of the epidermal carcinoma cell line, A431, were grown to incomplete confluence in a Permanox tissue culture chamber slide (Nunc, Inc., Naperville, Illinois, USA) in Dulbecco's Minimal Essential Medium (DME) containing 5% fetal calf serum (FCS). After removal of the medium, 200 µl of a solution containing 20% ethanol was added to each chamber and incubation was carried out for two minutes. The ethanolic medium was then removed and the monolayers were washed twice with DME (minus the FCS).

A DME solution containing C1171-NorFes-C1171 at a concentration of $1\times10^{-7}$ M was then incubated with the monolayer for 10 minutes. The cells were then examined for fluorescence with a Nikon fluorescence microscope using a rhodamine filter cube. (An advantage of using peptides homo-doubly-labeled with a single fluorophore compared to those labeled with two different fluorophores (hetero-doubly-labeled) is that fluorescence microscopy using homo-doubly-labeled peptides only requires a cutoff filter (i.e., a filter that transmits all light above a defined wavelength) on the emission side of the dichroic mirror, whereas fluorescence microscopy using hetero-doubly-labeled peptides preferably uses an interference filter (i.e., a filter that transmits light in a defined wavelength range (x±y nm)).

Each cell was clearly defined by a diffuse red fluorescence (produced by the protease indicator cleaved by elastase) filling its entire cytoplasm. For cells at the edge of a confluent island, the black borders of the islands were clearly distinct from the red fluorescence in the cytoplasm of the cells indicating that the fluorescence was not due to background fluorescence or to cleavage of the protease indicator by the medium.

Example 8

In addition, we have synthesized and derivatized (homodoubly-labeled) PAI-2, CS-1 (a 31 residue long pepetide) and two DEVD (SEQ ID NO:2)-like peptides that did not allow the dye—dye dimer formation. The CS-1 peptide shows that in a significantly longer peptide the dye—dye dimer structure can be formed. Note this peptide contains four proline residues in the amino terminal site of the putative cleavage site Ile-Leu bond. There is one proline in the carboxyl domain also. The results from the CS-1 peptide support a potentially larger sequence between the two dyes (fluorophores). Two DEVD (SEQ ID NO:2)-like peptides' amino acid sequences that did not allow the formation of productive H-type dimers are $F_1$-DEVDGIDPK[$F_1$]GY (SEQ ID NO:161) and $F_{,1}$PDEVDGIDPK[$F_1$]GY (SEQ ID NO:162).

Example 9

Cellular Uptake of Substrates Examined by Flow Cytometric and Fluorescence Microscopic Analysis The compounds listed in Table 12 were synthesized and assayed for cellular uptake. Cellular internalization of the substrates was tested using Jurkat cells (a human acute T cell leukemic line), HL-60 cells (a human promyelocytic leukemic line), human lymphocyte lines, A1.1 cells (a murine T-cell line), and murine primary thymocytes. Procedures used. in determining substrate uptake by viable cells are provided in Example 6 (for the HPLC procecures), in Example 2 (for the fluorescence microscopic analysis), and in Example 3 (for the flow cytometric analysis). A summary of these analyses with respect to cellular uptake of substrates is presented in this example.

TABLE 12

Compounds assayed for cellular uptake. Abbreviations used in the following table are: $F^1$: carboxytetramethylrhodamine; Z: benzyloxycarbonyl group; Fm: Fmoc group; K[F1]: $F^1$ is covalently attached through the epsilon amino group of lysine (K). Single letter amino acid residues are used in the sequences except for Nlu for norleucine, B for aminoisobutyric acid and J for epsilon amino caproic acid residue. H: HPLC, FM: Fluorescence microscopy, FC: flow cytometry.

|    | Structure | Cellular uptake/ magnitude | Uptake checked by | SEQ ID NO: |
|----|-----------|---------------------------|-------------------|------------|
| 1  | Fm-K[F1]DAIPNluSIPK[F1]GY | Yes/high | FM | 163 |
| 2  | K[F1]DAlPNluSIPK[F1]GY | Yes/weak | FM | 164 |
| 3  | Fm-DAIPNluSIPK[F1]GY | No/ | FM | 165 |
| 4  | Fm-K[F1]DBDEVDGIDPK[F1]GY | Yes/high | FM & FC | 166 |
| 5  | K[F1]DBDEVDGIDPK[F1]GY | Yes/weak | FM | 167 |
| 6  | Fm-K[F1]DBDEVNGIDPK[F1]GY | Yes/high | FM | 168 |
| 7  | K[F1]DBDEVNGIDPK[F1]GY | Yes/weak | FM & H | 169 |
| 5  | Fm-K[F1]DBEVDGIDPK[F1]GY | Yes/high | FM & FC | 170 |
| 9  | K[F1]DYBADGIDPK[F1]GY | Yes/weak | FM | 171 |
| 10 | Fm-K[F1]DBGDEVDGIDGPK[F1]GY | Yes/high | H & FC | 172 |
| 11 | Fm-K[F1]DBJGDEVDGIDGJPK[F1]GY | Yes/high | FC | 173 |
| 12 | Z-K[F1]DBJGDEVDGIDGJPK[F1]GY | Yes/weak | FM | 174 |

TABLE 12-continued

Compounds assayed for cellular uptake. Abbreviations used in the following table are: F$^1$: carboxytetramethylrhodamine; Z: benzyloxycarbonyl group; Fm: Fmoc group; K[F1]: F$^1$ is covalently attached through the epsilon amino group of lysine (K). Single letter amino acid residues are used in the sequences except for Nlu for norleucine, B for aminoisobutyric acid and J for epsilon amino caproic acid residue. H: HPLC, FM: Fluorescence microscopy, FC: flow cytometry.

| | Structure | Cellular uptake/ magnitude | Uptake checked by | SEQ ID NO: |
|---|---|---|---|---|
| 13 | Fm-K[F1]DYBADGIDPK[F1]GY | Yes/high | FM | 175 |
| 14 | K[F1]DBEVDGIDPK[F1]GY | Yes/weak | FM | 176 |

The data listed in Table 12 indicate that: (1) the presence of two fluorophores alone is not optimum for cellular uptake as illustrated by structures 2, 5, 7, and 9; (2) addition of a 9-fluorenylmethoxycarbonyl (Fmoc) group at the alpha amino group plus attachment of only one fluorophore, does not result insignificant cellular uptake (e.g., compound 3); and (3) two fluorophores plus at least one Fmoc group allows efficient cellular uptake of the substrates (structures 1,4,6,8,10, 11, and 12).

Other experiments utilizing protease substrates of this invention labeled with two identical fluorophores and at least one additional hydrophobic group such as an Fmoc group fits this paradigm. Replacing this Fmoc group with the less hydrophobic and smaller benzyloxycarbonyl group resulted in lower levels of cellular uptake, but was significantly better than a compound without a hydrophobic group such as DEVD peptide compound structure 5.

These data indicate that Fmoc may be replaced with Benzyloxycarbonyl, Z, or other hydrophobic groups such as Xanthyl (Xan), Trityl (Trt), 4-methyltrityl (Mtt), 4-methoxytrityl (Mmt), 4-methoxy-2,3,6-trimethylbenzenesulphonyl (Mtr), Mesitylene-2-sulphonyl (Mts), 4,4'-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA).

When the acid groups on compound 5, DEVD (SEQ ID NO:2) peptide, were esterified with ethanol, this modified peptide did not show any enhanced cellular uptake by viable cells. Hence the importance of the Fmoc group and the two fluorophores forming H-type dimers are illustrated by this negative example.

Example 10

Fluorescence Microscopic Analysis of Cells Incubated with Elastase or Apoptosis-Related Protease Substrates The elastase substrate, Fm-K[F1]DAIPNluSIPK[F1]GY (SEQ ID NO:163), (where F1 was carboxytetramethylrhodamine, Fm was Fmoc, K[F1] was F1 covalently attached through the epsilon amino group of lysine (K), and Fm-K is the Fmoc group covalently attached at the alpha amino group of the amino terminal lysine residue) was used with HL-60 cells. Cells were incubated with various concentrations of elastase substrate ranging from 10 nM to 10 $\mu$M for 5 minutes to 60 minutes. Then the cells were diluted 5-fold with RPMI 1640 medium containing 5% serum or with phosphate buffered saline. The samples were centrifuged and washed once more with 1 ml of washing solution. After centrifugation and removal of the washing solution, cell pellets were loosened with about 25 ul of medium and these cells were transferred to a glass capillary. Capillary tubes were then placed on a glass microscope slide and examined under a fluorescence microscope using standard rhodamine filters.

For apoptosis-related protease activity determination, 10 $\mu$M concentration of the compounds listed in Example 9 (compound structures 2 through 13) were incubated with cells for 30 min. to 3 hours. The cells were then washed similarly twice. Using glass capillary tubes, the washed cells were transferred and examined under a fluorescence microscope.

Example 11

Flow Cytometric Analysis of Cells Incubated with Apoptosis-Related Protease Substrates The concentration of substrates used in flow cytometric analysis was 10 $\mu$M in RPM11640 medium containing 4 to 10% fetal calf serum. Cell densities during incubation with the chosen substrates ranged from 50,000 cells per ml to 4,000,000 per ml. Incubation times were from 30 min. to 3 hours at 37 degree C. and incubation volumes were 50 $\mu$l to 2 ml. After incubation with substrate for 30 to 60 min, cell suspensions were diluted 10 old with ice cold Hank's Buffered Saline Solution (HBSS) and then filtered through a nylon fabric sheet. This filtered cell suspension was then subjected to flow cytometric analysis using a 488 nm excitation source. Becton Dickenson, Inc.'s flow cytometer, FacSort, was used in the flow cytometric analysis. Typically, 10,000 to 30,000 events per sample were collected.

Control cells without substrate incubation and the sample with the greatest expected fluorescence signals were used to set the instrument detector parameters. For example after 15 minutes' incubation of Jurkat cells with substrate compound #11 Fm-CGD2D: Fm-K[F1]DBJGDEVDGIDGJPK[F1]GY (SEQ ID NO:173) (where F1 was carboxytetramethylrhodamine; Fm was Fmoc, K[F1] was F1 covalently attached through the epsilon amino group of lysine (K), Nlu was norleucine, B was aminoisobutyric acid, and J was epsilon-aminocaproic acid) an increase of about 10 channels indicating cellular uptake of the substrates was measured. Note substrate #11 was not completely quenched. Hence, a small amount of background fluorescence would be expected from the intact substrate. Signals from the cells that had been activated with 1 ug/ml of ant-Fas antibody, CH11 clone for 1 to 6 hours indicated an increase in peak channel number. As much as a ten-fold increase in fluorescence intensity was observed. When the cells were co-incubated with the CPP32 protease inhibitor ZVAD-fluoromethylketone at 50 $\mu$M along with an apoptosis inducing agent, e.g., anti-Fas antibody, this observed increase in fluorescence intensity was eliminated. This indicated that the signal from compound 11 was due to the CPP32 protease activity which was inhibitable by ZVAD-FMK. Hence, the observed fluorescence intensity in each cell as determined by flow cytometric analysis served as a direct measure of the intracellular CPP32 protease activity.

Example 12

Competitive Substrate Inhibitors Illustrated by Their Effects on Cell Lysate Hydrolysis of Apoptosis-related Protease Substrates The level of CPP32 protease activity in the 6 hr ant-Fas-stimulated Jurkat cell lysate was examined using the protease substrate, DEVD-AFC (SEQ ID NO:177) (where AFC is aminofluoromethyl coumarin) 50 $\mu$M substrate concentration at 37° C. The buffer used was 50 mM HEPES, pH7.5, 10%w/v sucrose, 0.1%w/v CHAPS.) Fluorescence intensity changes were monitored with an SLM 48000 spectrofluorometer. The hydrolysis rate of DEVD-AFC (SEQ ID NO:177) was found to depend upon the concentration of DEVD (SEQ ID NO:2), DEVN (SEQ ID NO:3), and ICE substrates (compounds 5, 7, and 9 in Table 12) present in the reaction mixtures. As the concentrations of DEVD (SEQ ID NO:2), DEVN (SEQ ID NO:3), and ICE were raised to 25 $\mu$M, the rate of DEVD-AFC (SEQ ID NO:177) hydrolysis was decreased. Hence, DEVD (SEQ ID NO:2), DEVN (SEQ ID NO:3) and ICE substrates do bind to the substrate binding site of target proteases such as CPP32 and act as competitive inhibitors since their hydrolysis rates are slower than that of DEVD-AFC (SEQ ID NO:177) substrate. It was surprising to find that the substrate control peptide with its $P_1$ residue mutated with a conservative uncharged residue Asn still retained the ability to bind to the protease substrate binding site and exhibit enzyme inhibition.

Example 13

Substrates Delay and Inhibit Apoptosis Stimuli in Whole Cells

Jurkat cells are normally grown in 10% fetal calf serum containing RPMI 1640, at 37° C. in a 5% $CO_2$ atmosphere. When the serum content was dropped to 4%, the Jurkat cell growth rate not only slowed down but also a significant number of cells died within 36 hours. The cell density used was about 400,000 cell per ml. After 36 hours, control wells contained about 50% dead cells (trypan blue-positive cells), whereas the wells containing 0.1 or 1.0 $\mu$M concentration of compound #11 (Table 12) "Fm-CGD2D" or Fm-K[F1] DBJGDEVDGIDGJPK[F1]GY showed only (SEQ ID NO:173) 10% or 8% nonviable cells. Hence, compound #11 which exhibits efficient cellular uptake slowed down apoptosis in these Jurkat cells where it acted as a CPP32 protease inhibitor or a CPP32 activating protease inhibitor.

Example 14

Isolation of Intact and Cleaved Substrate Fragments from Cells

Jurkat cells, which had been induced into apoptosis by the ant-Fas antibody (1 ug/ml for 2 hours at 37 degree C.) were incubated with 10 $\mu$M substrate compound #10 Fm-G2D2D. After one hour incubation with this substrate, the cells were washed with 4% serum containing RPMI 1640 medium (1 ml wash solution for every 100 $\mu$l of incubation medium). Cells were washed three times, then solubilized with cell lysis buffer containing Triton X-100. This cell lysate was then analyzed using a $C_4$ reverse phase chromatography column and a water/acetonitrile eluent system containing 0.075% trifluoroacetic acid throughout. Analysis showed the presence of intact substrate with two major new peaks that eluted earlier than the intact substrate. The two recovered major peaks showed rhodamine absorption spectra; hence, these correspond to two major substrate fragments that are generated upon protease cleavage of the substrate.

Example 15

Fluorescence Signal from Devn Substrates When Mixed with Target Enzyme Containing Solution DEVN (SEQ ID NO:3) (10 $\mu$M), a substrate control peptide, compound 7 of Table 12, was found to be resistant to protease digestion by an apoptosis-activated Jurkat cell lysate. Extensive digestion time did not result in any further increase in fluorescence intensity. HPLC reverse phase analysis of this reaction mixture confirmed the presence of a totally uncleaved substrate. Substitution of the $P_1$ residue, Asp, by a non-charged amino acid Asn resulted in converting a protease substrate into a protease non-substrate.

This control peptide exhibited competitive substrate inhibition in the experiment as described in Example 12. In addition, fluorescence intensity monitoring as a function of time after addition of cell lysate showed a significant increase in fluorescence intensity initially but after 15 minutes this initial intensity level stabilized. Recalling that there was no substrate cleavage by the proteases present in the cell lysate, the best explanation of this initial fluorescence intensity is due to the DEVN (SEQ ID NO:3) substrate binding to the protease and the substrate undergoing a conformational change. This conformational change involving the substrate's backbone also affects the conformation of two covalently attached fluorescent dye molecules with respect to each other in terms of mean distance and relative orientation. The degree of fluorescence quenching of these two fluorophores in the substrate structure has been found to be sensitive to their distance and the specific orientation with respect to their dipoles. Hence, any conformational change that affects these two aspects of the fluorescence reporting molecules would be expected to affect the fluorescence quenching as well. Thus, conformational changes induced by a substrate binding to a protease's substrate binding site is reflected in the observed initial fluorescence intensity changes, i.e., an increase in its fluorescence intensity. Since the substrate cannot be cleaved, the initial fluorescence intensity increase levels off. One can utilize this observed fluorescence intensity increase due to conformational change of the substrate rather than substrate cleavage as a new kind of readout such as degree of association between the substrate and its target binding molecule.

Example 16

Variation of Hydrolysis Rates Induced by Varying the Flexibility of the Protease Recognition Domain by Various Conformation Determining Domain (Cdr) Amino Acid Sequences Protease cleavage sites of physiologically relevant substrates for any give protease may be classified into two cases. One is the serine protease inhibitors such as neutrophil elastase inhibitor or alpha 1 antitrypsin where the elastase recognition sequence is rather rigidly held by the remaining inhibitor molecule. Upon cleavage by elastase, this protease reactive site and its newly formed terminal residues undergoes significant conformational change as evidenced by high resolution crytallographic structural analyses of reactive and cleaved inhibitor structures. In the second class of protease cleavage sites the cleavage sequences are in domains where conformations are not well defined or there is a significant amount of flexibility, as much as in free linear peptides. It is said that some degree of defined conformation or a less than maximally available backbone flexibility difference between two potential substrates results in a given protease's preference for one substrate over another.

Compounds 4 (Fm-DEVD), 10 (Fm-G2D2D), and 11 (Fm-CGD2D) illustrate how one can introduce varying amount of constrained conformational space or flexibility into a given substrate with the same protease recognition domain but with different conformation determining domains or regions (CDRs) while retaining the bent forming function of the CDRs. This example illustrates how one can vary relative rigidity or flexibility of the central protease recognition domain by changing the CDR's conformational flexibility or rigidity.

The parent compound Fm-DEVD has the following composition: Fmoc-K[F1]DB<u>DEVDGID</u>PK[F1]GY (SEQ ID NO:166). The bold face underlined letters are the protease recognition sequence consisting of 7 amino acid residues. Compound #10 contains two glycine extensions at both ends of this protease recognition sequence. The central protease recognition domain now is 8 residue long GDEVDGID (SEQ ID NO:178), since the glycine residue at the amino terminus is a part of native sequence. The two glycine residues which are inherently more flexible than other amino acids, e.g., alanine, provide less conformational constraint or, conversely, more flexibility than compound 4 (Table 12) and thereby permit greater flexion when combined with Aib or Pro residues. Additional insertion of amino caproic acid at both termini with five methylene groups in addition to the one present in glycine provides further relaxation of the constrained conformation and, thus, greater flexibility for the protease recognition domain, GDEVDGID (SEQ ID NO:178). This progression of flexibility resulted in an increased hydrolysis rate with the CPP32 protease since CPP32 recognizes a more flexible protease recognition domain than does elastase. Support for this statement is that the CPP32 protease cleavage site in the proform of its physiological substrate, poly(ADP-ribose) polymerase, PARP, is located between two well-folded domains. Hence, it is expected that such a protease cleavage site would not be rigidly held or its conformation would be expected to be less defined than the remaining molecule. Hence, in order to provide these structural features to the substrate, introduction of flexible residues such as glycine, epsilon amino caproic acid, beta alanine, and amino butyric acid would be expected to play important roles in regulating the backbone flexibility of the substrate's central protease recognition domain. These additional preferred residues for the conformation determining domain are also expected to provide the needed bend-inducing influence.

The observed varied hydrolysis rates for these three substrates point to success in regulating the flexibilities of the protease recognition domains. This, is reflected in the observed difference in proteolysis rates while maintaining the appropriate orientation for the two fluorophores to interact with each other through space. The importance of this conformation determining domain in providing a means to regulate flexibility as well as allowing the amino and carboxyl termini to orient in space appropriately close is examplified by these compounds (4, 10, and 11).

These examples provide a tetrapeptide and a pentapeptide comprising Lys-Asp-Aib-Gly (SEQ ID NO:179) or Lys-Asp-Aib-Ahx-Gly (SEQ ID NO:180) where Ahx is episilon amino caproic acid (i.e. $NH_2$—$(CH_2)_5$—COOH). The fluorophore is attached to episilon amino group of the lysine residue. The carboxyl terminal CDR domain is defined as a tripeptide Gly-Pro-Lys and a tetrapeptide Gly-Ahx-Pro-Lys (SEQ ID NO:181). The hydrolysis rate was increased by 3-fold between compounds 4 (Fm-DEVD: Fm-K[F1] DBDEVDGIDPK[F1]GY; SEQ ID NO:166) and 10 (Fm-G2D2D: Fm-K[F1]DBGDEVDGIDGPK[F1]GY]; SEQ ID NO:172)

Figure 5:
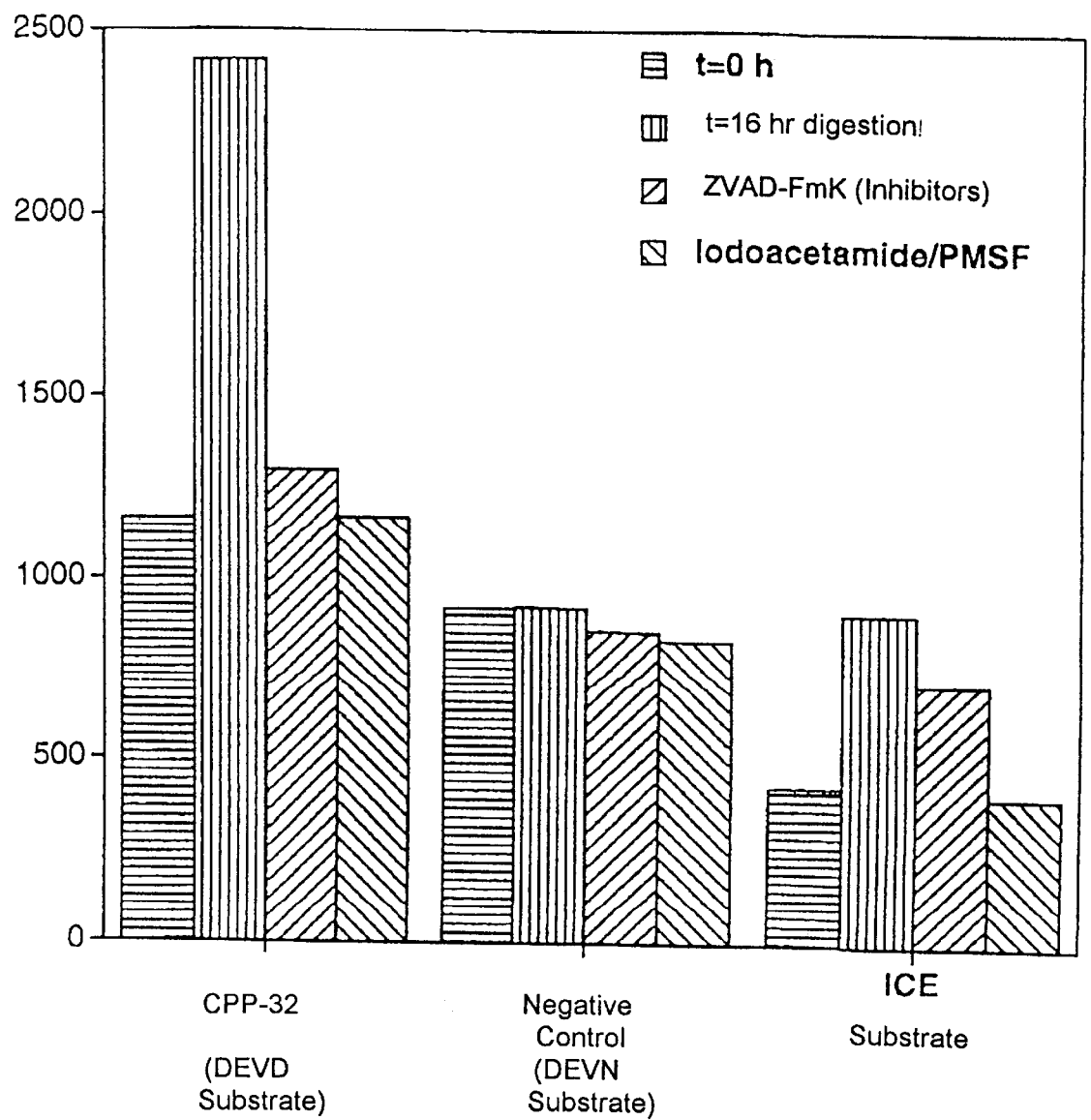
FIG. 5 illustrates fluorescence of a DEVD (SEQ ID NO:2), a DEVN (SEQ ID NO:3), and an ICE substrate. To one hundred µl of assay buffer (50 mM HEPES buffer pH 7.5, 10% (w/v) sucrose and 0.1% (w/v) CHAPS) containing 1 µM of substrate DEVD (SEQ ID NO:2) (compound 2 of Example 8), DEVN (SEQ ID NO:3) (compound 3 of Example 8) and ICE (compound 5 of Example 8) 10 µl of Jurkat cell lysate was added and incubated for 16 hours at 37° C. The Jurkat cells' lysate was prepared from the cells that had been stimulated by antiFas antibody at 1 µg/ml concentration for 6 hours. The fluorescence intensity for the substrate solution alone is indicated in FIG. 5 as a horizontal lined bar marked as t=0 hr and the fluorescence intensity of the lysate and substrate solution mixture after 16 hr is indicated by vertical line bar and is marked as t=16 hr digestion. 10 µl cell lysate was priincubated with 50µm ZVAD-FMK (benzyoxycarbonyl valanyl alanyl aspartyl-fluoromethylketone) at 37 degree C. for 30 min. then added to the substrate solution. The fluorescence intensity after 16 hours for this mixture is indicated by the bar marked as ZVAD-FMK (inhibitor). Lastly, preincubated cell lysate with iodoacetamide( alkylating agent for sulfhydryl group) and PMSF ( for inhibiting serine proteases) was added to the substrate solution. The fluorescence intensity after 16 hours at 37° C. is indicated by bar marked as lodoacetamide/PMSF. The DEVN (SEQ ID NO:3) substrate is a negative control substrate where the P1, Asp, residue is replaced by Asn. The CPP32 protease requires the P1 residue to be aspartic acid residue. The four bar graphs for the DEVN (SEQ ID NO:3) substrate (FIG. 5) clearly indicate that the activated cell lysate do not contain any other protease that digest the DEVD (SEQ ID NO:2) substrate, since the intensity for 16 hour digestion is the same as the substrate alone. The bar graphs for the DEVD (SEQ ID NO:2) substrate indicate that the activate cell lysate do contain CPP32 protease and this protease activities are inhibited by ZVAD-FMK, known CPP32 protease inhibitor. The contribution of any other proteases in digesting DEVD (SEQ ID NO:2) substrate is very small as indicated by the difference between the intensities of ZVAD-FMK bar to lodoacetamide/PMSF bar.

As illustrated in FIG. 5, the hydrolysis rate was further increased by ca. 3-fold over the above glycine residue insertion with the amino caproic amino acid (Ahx) addition, compound 11 (Fm-CGD2D: Fm-K[F1]DB Ahx GDEVDG-IDG Ahx PK[F1]GY; SEQ ID NO:173). Hence, overall at least a 9-fold increase in substrate hydrolysis rate was accomplished (compounds 4 and 11, Table 12).

Example 18

Structural Characteristics of Fluorophores Which Form Intramolecular H-type Dimers in a Protease Substrate The strongest correlations between H-dimer formation and structural elements of various potential fluorophores for use in the homo-doubly labeled fluorgenic compositions of this invention are in order: delocalized charge, symmetry, and transition dipole magnitude. Hydrophobicity was not observed to be a major determinant in this type of dimerization.

In the experiments described herein, a new class of profluorescent protease substrate was designed and synthesized. These new fluorogenic indic ators have spectral properties that fit the exciton model; More specifically, spectra of these polypeptides which were doubly labeled with rhodamines showed a blue-shifted absorption peak and fluorescence quenching, both indicators of H-dimer formation.

For example, NoreFes, an undecapeptide which is cleaved by the serine protease elastase, was homodoubly labeled on opposite sides of its cleavage site with six fluorophores in order to identify structural elements of dyes which influence intramolecular H-type dimer formation. Absorption and fluorescence spectra of these six substrate obtained before and after enzymatic cleavage suggest that the presence of a delocalized charge followed by symmetry and then magnitude of the lowest energy electronic transition dipole are important factors in dimer formation. Surprisingly, there was no evidence that hydrophobic interactions were important in the fluorophores used in this study.

The six flurophores used in this study were rhodamine-X, tetramethylrhodamine, fluorescein, diethylaminocoumarin, hydroxycoumarin and pyrene.

While the xanthene components of these two rhodamines (rhodamine-X, tetramethylrhodamine) have the same charge and symmetric structure, the distinguishing characteristics between them are a higher transition dipole magnitude and lower hydrophobicity of the tetramethylrhodamine. One notes that the spectrum of the intact tetramethylrhodamine-derivatized substrate shows a more prominent change than that of rhodamine-X when comparing the absorption spectra of the two doublylabeled intact peptides with those from the respective cleaved solution.

As noted above, in contrast to the two rhodamine derivatives where a charge of +1 is localized over each of the xanthene structure, the three conjugated ring component of the fluorescein was uncharged at pH 9. The lack of any significant shape changes in the absorption spectra after separation of the dyes (fluorescein ) by cleavage of the peptide suggests a role for charge in H-dimer formation. The less pronounced, but neverthless finite quenching observed with this derivative points toward a diminished but finite degree of interaction between two fluoresceins compared with interactions between either of the two rhodamines is consistent with previous studies of xanthenes in solution where the association constant for dimer formation for fluorescein is four order of magnitude lower than that for rhodamines.

The influence of dye symmetry was next examined using two coumarins, i.e. diethylaminocoumarin and hydroxycoumarin. This class of molecules contains no symmetrical elements. The diethylaminocoumarin bears a positive charge delocalized over its two conjugated rings, similar to the rhodamines and the hydroxycoumarine is neutral at pH 9, similar to fluorescein. The spectrum of diethylaminocoumarin-labeled NorFes exhibits a blue shift of 11 nm while that of hydroxycoumarin-labeled NorFes shows just a slight blue shoulder. The respective degree of quenching, 76% and 28% of the intact peptides relative to the cleaved solutions is consistent with the importance of delocalized charge. Comparing the less pronounced spectral changes of the diethylaminocoumarin-derivatized peptide with those of the xanthenes gives support to the role of symmetry as an important element in H-dimer formation.

Finally, the role of hydrophobicity was studied using pyrene, a fluorophore with S2 symmetry containing only carbons and hydrogens. No spectral changes were observed in either the absorption or the fluorescence mode and the magnitude of the transition dipole is extremely small. These results provide evidence against a dominant role for hydrophobicity in H-dimer formation.

In summary, the strongest correlations between H-dimer formation and structural elements are in order: delocalized charge, symmetry, and transition dipole magnitude. Hydrophobicity was not observed to be a major determinant in this type of dimerization.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A fluorogenic composition for the detection of the activity of a protease, said composition having the formula:

$$F^1\text{-}aa^1_j\text{-}(aa^2\text{-}aa^3)_k\text{-}aa^4_l\text{-}aa^5\text{-}X_m\text{-}P\text{-}Y_n\text{-}aa^6\text{-}aa^7_o\text{-}(aa^8\text{-}aa^9)_p\text{-}aa^{10}_q\text{-}F^2$$
$$\quad\quad\quad|\quad\quad\quad\quad\quad\quad\quad\quad\quad\quad\quad\quad\quad\quad\quad\quad\quad\quad\quad\quad\quad\quad\quad|$$
$$\quad\quad\quad(S^1)_i\quad\quad\quad\quad\quad\quad\quad\quad\quad\quad\quad\quad\quad\quad\quad\quad\quad\quad\quad(S^2)_r$$

wherein, P is a peptide comprising a protease binding site for said protease, said binding site consisting of about 2 to about 8 amino acids;

$F^1$ and $F^2$ are fluorophores and $F^1$ is attached to the amino terminal amino acid and F2 is attached to the carboxyl terminal amino acid;

$S^1$ and $S^2$, when present, are peptide spacers ranging in length from 1 to about 50 amino acids and $S^1$, when present, is attached to the amino terminal amino acid and $S^2$, when present, is attached to the carboxyl terminal amino acid;

i, j, k, l, m, n, o, p, q, and r are independently 0 or 1;

$aa^1$ and $aa^{10}$ are independently selected from the group consisting of lysine, ornithine and cysteine;

$aa^2$, $aa^3$, $aa^8$, and $aa^9$ are independently selected from the group consisting of Asp, Glu, Lys, Ornithine, Arg, Citulline, homocitrulline, Ser, homoserine, Thr, and Tyr;

$aa^5$, $aa^4$, $aa^6$, and $aa^7$ are independently selected from the group consisting of proline, 3,4-dehydroproline, hydroxyproline, alpha aminoisobutyric acid and N-methyl alanine;

X is selected from the group consisting of Gly, βAla, γAbu ,Gly-Gly, Ahx, βAla-Gly, βAla-βAla, γAbu-Gly, βAla-γAbu, Gly-Gly-Gly (SEQ ID NO:37), γAbu-γAbu, Ahx-Gly, βAla-Gly-Gly, Ahx-βAla, βAla-βAla-Gly, Gly-Gly-Gly-Gly, Ahx-γAbu, βAla-βAla-βAla, γAbu-βAla-Gly, γAbu-γAbu-Gly, Ahx-Ahx, γAbu-γAbu-βAla, and Ahx-Ahx-Gly;

Y is selected from the group consisting of Gly, βAla, γAbu, Gly-Gly, Ahx, Gly-βAla, βAla-βAla, Gly-γAbu, γAbu-βAla, Gly-Gly-Gly, γAbu-γAbu, Gly-Ahx, Gly-Gly-βAla,βAla-Ahx, Gly-βAla-βAla, Gly-Gly-Gly-Gly (SEQ ID NO:37), γAbu-Ahx, βAla-βAla-βAla, Gly-βAla-γAbu, Gly-γAbu-γAbu, Ahx-Ahx, βAla-γAbu-γAbu, and Gly-Ahx-Ahx;

when i is 1, $S^1$ is joined to $aa^1$ by a peptide bond through a terminal alpha amino group of $aa^1$; and when r is 1, $S^2$ is joined to $aa^{10}$ by a peptide bond through a terminal alpha carboxyl group of $aa^{10}$.

2. The composition of claim 1, wherein P is selected from the group consisting of TGRTG (SEQ ID NO:182), DEVDGID (SEQ ID NO:183), DEVNGID (SEQ ID NO:184), DEVNGIN (SEQ ID NO:58), EVDGID (SEQ ID NO:185), ADGID (SEQ ID NO:186), AIPMSI (SEQ ID NO:187), GDEVDGID (SEQ ID NO:179), GDEVDGIN (SEQ ID NO:188), GNEVDGID (SEQ ID NO:189), GNEVDGIN (SEQ ID NO:190), ODEVDGID (SEQ ID NO:191), dODEVDGID, WDEVDGID (SEQ ID NO:192), dWDEVDGID, dOdODEVDGID, dWdWDEVDGID, YVADGID (SEQ ID NO:193), YVADGIN (SEQ ID NO:194), YVANGIN (SEQ ID NO:195), and dYVADGIN.

3. The composition of claim 1, wherein P is selected from the group consisting of LVEIDNG (SEQ ID NO:196), LVEINNG (SEQ ID NO:197), GIETDSGVDD (SEQ ID NO:198), GIETNSGVDD (SEQ ID NO:199), GIETNSGV (SEQ ID NO:200), GIETDSGV (SEQ ID NO:201), GSESMDSGISLD (SEQ ID NO:202), GSESMDSG (SEQ OD NO:203), DVVCCSMS (SEQ ID NO:141), DVVCDSMS (SEQ ID NO:204), DVVCSdMS, DVVCCPdMS, EDVVCCS (SEQ ID NO:205), EDdVVCCP, EDdVVCDP, DdVVCCSdMS, DVdVCDSdMS, DdVVCCPdMS, DVVCCSM (SEQ ID NO:206), DVVCDSM (SEQ ID NO:207), VCCSM (SEQ ID NO:208), and VCDSM (SEQ ID NO:209).

4. The composition of claim 1, wherein P is selected from the group consisting of DEMEECSQHL (SEQ ID NO:210), DEMEECPQHL (SEQ ID NO:211), EMEECSQHL (SEQ ID NO:212), EMEECPQHL (SEQ ID NO:213), EMEEDSQHL (SEQ ID NO:214), VMTGRTG (SEQ ID NO:215), VdMTGRTG, VMTGRG (SEQ ID NO:216), VdMTGRG, VMTGRVG (SEQ ID NO:217), VdMTGRVG, VMTGRAG (SEQ ID NO:218), VdMTGRAG, SEVNLDAEF (SEQ ID NO:219), SEVKLDAEF (SEQ ID NO:220), SEVKMDAEF (SEQ ID NO:221), SEVKMDDEF (SEQ ID NO:222), SEVNLDDEF (SEQ ID NO:223), GVVIATVIVIT (SEQ ID NO:224), YGVVIATVIVIT (SEQ ID NO:225), VIATVI (SEQ ID NO:226), YGVVIA (SEQ ID NO:227), QQLLNH (SEQ ID NO:228), SIQYTY (SEQ ID NO:229), SSQYSN (SEQ ID NO:230), and SSIYSQ (SEQ ID NO:231).

5. The composition of claim 1, wherein $F^1$ and $F^2$ are the same fluorophore.

6. The composition of claim 5, wherein said $F^1$ and $F^2$ have an excitation wavelength between about 315nm and about 700 nm.

7. The composition of claim 1, wherein the $F^1$ molecule is attached through either an a amino group of the $aa^1$ amino acid or through a side chain amino group of the $aa^1$ amino acid, or through a sulfhydryl group of a side chain of the $aa^1$ amino acid.

8. The composition of claim 1, wherein the $F^2$ molecule is attached either through a side chain amino group of the $aa^{10}$ amino acid, through a carboxyl group of the $aa^{10}$ amino acid, or through a sulfhydryl group of a side chain of the $aa^{10}$ amino acid.

9. The composition of claim 1, wherein said fluorophore is selected from the group consisting of carboxytetramethylrhodamine, carboxyrhodamine-X and diethylaminocoumarin.

10. The composition of claim 1, wherein said composition bears a hydrophobic group.

11. The composition of claim 10, wherein said hydrophobic group is selected from the group consisting of: Fmoc, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4'-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA).

12. The composition of claim 11, wherein said hydrophobic group is Fmoc.

13. The composition of claim 11, wherein said hydrophobic group is attached to the amino terminus of the molecule.

14. The composition of claim 1, wherein said composition has an amino acid sequence selected from the group consisting of KDBTGRTGPKGY (SEQ ID NO: 38), KDBDEVDGIDPKGY (SEQ ID NO: 40), KDBDEVNGIDPKGY (SEQ ID NO: 41), KDBEVDGIDPKGY (SEQ ID NO: 42), KDYBADGIDPKGY (SEQ ID NO: 43), Fmoc-KDBDEVDGIDPKGY (SEQ ID NO: 44), Fm-KDBDEVNGIDPKGY (SEQ ID NO: 45), Fmoc-KDBEVDGIDPKGY (SEQ ID NO: 46, Fmoc-KDAIPMSIPKGY (SEQ ID NO: 47), Fmoc-KDBGDEVDGIDGPKGY (SEQ ID NO: 48), Fmoc-KDBJGDEVDGIDGJPKGY (SEQ ID NO: 49), Z-KDBGDEVDGIDGJPKGY (SEQ ID NO: 50), Fmoc-KDYBADGIDPKGY (SEQ ID NO: 51).

15. The composition of claim 2, having the sequence Fmoc-KDP JG DEVDGIN GJ PKGY (SEQ ID NO: 54 where Xaa at position 3 is the amino acid proline).

16. The composition of claim 2, having the sequence Fmoc-KDP JG DEVNGIN GJ PKGY (SEQ ID NO: 56 where Xaa at position 3 is the amino acid proline).

17. The composition of claim 2, having the sequence Fmoc-KDP JG ODEVDGID GJ PKGY (SEQ ID NO: 58 where Xaa at position 3 is the amino acid proline).

18. The composition of claim 2, having the sequence Fmoc-KDP JG WDEVDGID GJ PKGY (SEQ ID NO: 59 where Xaa at position 3 is the amino acid proline).

19. The composition of claim 2, having the sequence Fmoc-KDP JG dWDEVDGID GJ PKGY.

20. The composition of claim 2, having the sequence Fmoc-KDP JG YVADGIN GJ PKGY (SEQ ID NO: 61 where Xaa at position 3 is the amino acid proline).

21. The composition of claim 2, having the sequence Fmoc-KDP JG YVANGIN GJ PKGY (SEQ ID NO: 62 where Xaa at position 3 is the amino acid proline).

22. The composition of claim 2, having the sequence Fmoc-KDP JG LVEIDNG GJ PKGY (SEQ ID NO: 70 where Xaa at position 3 is the amino acid proline).

23. The composition of claim 2, having the sequence Fmoc-KDP JG LVEINNG GJ PKGY (SEQ ID NO: 73 where Xaa at position 3 is the amino acid proline).

24. The composition of claim 2, having the sequence Fmoc-KDP JG GIETDSGV GJ PKGY (SEQ ID NO: 78 where Xaa at position 3 is the amino acid proline).

25. The composition of claim 2, having the sequence Fmoc-KDP JG GIETNSGV GJ PKGY (SEQ ID NO: 77 where Xaa at position 3 is the amino acid proline).

26. The composition of claim 2, having the sequence Fmoc-KDP JG GSESMDSG GJ PKGY (SEQ ID NO: 84 where Xaa at position 3 is the amino acid proline).

27. The composition of claim 2, having the sequence KDP JG VMTGRT GJ PKGY (SEQ ID NO: 105 where Xaa at position 3 is the amino acid proline).

28. The composition of claim 2, having the sequence KDP JG VMTGR GJ PKGY (SEQ ID NO: 107 where Xaa at position 3 is the amino acid proline).

29. The composition of claim 2, having the sequence KDP JG VMTGRV GJ PKGY (SEQ ID NO: 10 where Xaa at position 3 is the amino acid proline).

30. The composition of claim 2, having the sequence KDP JG SEVKLDAEF GJ PK DDY (SEQ ID NO: 113 where Xaa at position 3 is the amino acid proline).

31. The composition of claim 2, having the sequence KDP JG SEVKMDAEF GJ PK DDY (SEQ ID NO: 114 where Xaa at position 3 is the amino acid proline).

32. The composition of claim 2, having the sequence KDP JG SEVNLDAEF GJ PK DDY (SEQ ID NO: 112 where Xaa at position 3 is the amino acid proline).

33. The composition of claim 2, having the sequence KDP JG SEVKMDDEF GJ PK DDY (SEQ ID NO: 115 where Xaa at position 3 is the amino acid proline).

34. The composition of claim 2, having the sequence KDP JG SEVNLDDEF GJ PK DDY (SEQ ID NO: 116 where Xaa at position 3 is the amino acid proline).

35. A method of detecting the activity of a protease, said method comprising;
   (i) contacting said protease with a composition of claim 1;
   (ii) detecting a change in fluorescence or absorption in said composition whereby an increase in fluorescence or a shange in the absorbance spectrum of said composition indicates activity of said protease.

36. The method of claim 35, wherein said contacting is in a histological section.

37. The method of claim 35, wherein said contacting is in a cell suspension derived from a bioligical sample selected from the group consisting of a tissue, blood, urine, saliva, lymph, biopsy.

38. The method of claim 35, wherein said detecting is by a method selected from the group consisting of fluorescence microscopy, fluorescence microplate reader, flow cytometry, fluorometry, and absorption spectroscopy.

* * * * *